US010913777B2

(12) United States Patent
Hagen et al.

(10) Patent No.: US 10,913,777 B2
(45) Date of Patent: Feb. 9, 2021

(54) IN VITRO ASSEMBLY OF BACTERIAL MICROCOMPARTMENTS

(71) Applicant: The Regents of the University of California, Oakland, CA (US)

(72) Inventors: Andrew Ronald Hagen, Oakland, CA (US); Cheryl A. Kerfeld, Walnut Creek, CA (US); Markus Sutter, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 76 days.

(21) Appl. No.: 15/985,218

(22) Filed: May 21, 2018

(65) Prior Publication Data

US 2018/0334482 A1 Nov. 22, 2018

Related U.S. Application Data

(60) Provisional application No. 62/509,553, filed on May 22, 2017.

(51) Int. Cl.
| | | |
|---|---|---|
| *C07K 14/195* | (2006.01) | |
| *C07K 14/245* | (2006.01) | |
| *C07K 14/47* | (2006.01) | |
| *C12P 21/06* | (2006.01) | |
| *C12P 21/02* | (2006.01) | |
| *C12N 15/62* | (2006.01) | |
| *C12N 11/04* | (2006.01) | |

(52) U.S. Cl.
CPC .......... *C07K 14/195* (2013.01); *C07K 14/245* (2013.01); *C07K 14/47* (2013.01); *C12N 11/04* (2013.01); *C12N 15/62* (2013.01); *C12P 21/02* (2013.01); *C12P 21/06* (2013.01); *C07K 2319/00* (2013.01); *C07K 2319/21* (2013.01); *C07K 2319/24* (2013.01); *C07K 2319/50* (2013.01)

(58) Field of Classification Search
None
See application file for complete search history.

(56) References Cited

U.S. PATENT DOCUMENTS

| | | |
|---|---|---|
| 5,643,758 A | 7/1997 | Guan et al. |
| 6,872,551 B2 | 3/2005 | Lima et al. |
| 2012/0210459 A1 | 8/2012 | Kerfeld et al. |
| 2015/0026840 A1 | 1/2015 | Kerfeld et al. |
| 2017/0107523 A1 | 4/2017 | Kerfeld et al. |

OTHER PUBLICATIONS

Fan et al 2010 PNAS, vol. 107 ,No. 16 , 7509-7514 (Year: 2010).*
PNAS vol. 107 ,No. 16 Supporting information pp. 1-4. (Year: 2010).*
Batzer et al., Nucleic Acid Res. 19:5081 (1991).
Ohtsuka et al., J. Biol. Chem., 260:2605-2608 (1985).
Rossolini et al., Mol. Cell. Probes, 8:91-98 (1994).
Su et al. (2004) Biotechnol Bioeng 85:610-9 and Fetter et al. (2004).
Fetter et al. (2004) Plant Cell 16:215-28).
Bolte et al. (2004) *J. Cell Science* 117:943-54.
Kato et al. (2002) ant Physiol 129:913-42.
Axen SD, Erbilgin O, Kerfeld CA. PLoS Comput Biol. 2014; 10:e1003898.
Lassila, et al., Assembly of Robust Bacterial Microcompartment Shells using Building Blocks from an Organelle of Unknown Function. Journal of Molecular Biology, vol. 426, issue 11, May 29, 2014, pp. 2217-2228.
Shively JM, Ball F, Brown DH, Saunders RE. Science. 1973; 182:584-586. [PubMed: 4355679].
Kerfeld CA, et al al. Science. 2005; 309:936-938. [PubMed: 16081736].
Klein MG, et al. J Mol Biol. 2009; 392:319-333. [PubMed: 19328811].
Cai F, et al. J Biol Chem. 2013; 288:16055-16063. [PubMed: 23572529].
Tanaka S, et al. Science. 2008; 319:1083-1086. [PubMed: 18292340].
Sutter M, et al. Nano Letters. 2016; 16:1590-1595. [PubMed: 26617073].
Aussignargues C, et al. J Am Chem Soc. 2016; 138:5262-5270. [PubMed: 26704697].
Tsai Y, et al. PLoS Biol. 2007; 5:e144. [PubMed: 17518518].
Locher KP, Lee AT, Rees DC. Science. 2002; 296:1091-1098. [PubMed: 12004122].
Tanaka S, Sawaya MR, Yeates TO. Science. 2010; 327:81-84. [PubMed: 20044574].
Mallette E, Kimber MS. J Biol Chem. 2017; 292:1197-1210. [PubMed: 27927988].
Erbilgin O, McDonald KL, Kerfeld CA. Appl Environ Microbiol. 2014; 80:2193-2205. [PubMed: 24487526].
Liberton M, Austin JR 2nd, Berg RH, Pakrasi HB. Plant Physiol. 2011; 155:1656-1666. [PubMed: 21173021].
Aussignargues C, et al. Commun Integr Biol. 2015; 8:e1039755. [PubMed: 26478774].
Burgess RR. Methods Enzymol. 2009; 463:259-282. [PubMed: 19892177].

(Continued)

*Primary Examiner* — Padmavathi Baskar
(74) *Attorney, Agent, or Firm* — Knobbe, Martens, Olson & Bear, LLP

(57) ABSTRACT

The present disclosure is related to a BMC fusion protein that is capable of in vitro assembly, comprising a constituent BMC shell protein subunit and a sterically hindering protein domain that is cleavable. The BMC fusion protein is capable of in vitro assembly triggered by removal of the fused sterically hindering domain. The present disclosure is also related to a means to produce BMC shells in vitro, triggered by removal of a fused sterically hindering domain from one or more constituent BMC shell protein subunits. The BMC fusion protein enables encapsulation of broad classes of materials and biophysical studies of shell assembly, encapsulation, and permeability that would otherwise be unavailable from BMCs assembled in vivo.

6 Claims, 33 Drawing Sheets

Specification includes a Sequence Listing.

(56) References Cited

OTHER PUBLICATIONS

Kabsch W. Acta Cryst D. 2010; 66:125-132. [PubMed: 20124692].
Winn MD, et al. Acta Cryst D. 2011; 67:235-242. [PubMed: 21460441].
Emsley P, Cowtan K. Acta Cryst D. 2004; 60:2126-2132. [PubMed: 15572765].
Afonine PV, et al. Acta Cryst D. 2012; 68:352-367. [PubMed: 22505256].
Suloway C, et al. J Struct Biol. 2005; 151:41-60. [PubMed: 15890530].
Lander GC, et al. J Struct Biol. 2009; 166:95-102. [PubMed: 19263523].
Rohou A, Grigorieff N. J Struct Biol. 2015; 192:216-221. [PubMed: 26278980].
Scheres SHW. J Struct Biol. 2012; 180:519-530. [PubMed: 23000701].
Voss NR, et al. J Struct Biol. 2009; 166:205-213. [PubMed: 19374019].
Okamoto K, et al. Sci Rep. 2016; 6:33170. [PubMed: 27616740].
Scheres SHW, Chen S. Nat Meth. 2012; 9:853-854.
Rosenthal PB, Henderson R. J Mol Biol. 2003; 333:721-745. [PubMed: 14568533].
Pettersen EF, et al. J Comput Chem. 2004; 25:1605-1612. [PubMed: 15264254].
Larkin MA, et al. Bioinformatics. 2007; 23:2947-2948. [PubMed: 17846036].
Guindon S, et al. Syst Biol. 2010; 59:307-321. [PubMed: 20525638].
Han MV, Zmasek CM. BMC Bioinformatics. 2009; 10:356. [PubMed: 19860910].

\* cited by examiner

FIG. 1A
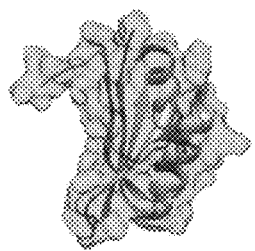
Single subunit of hexamer shell protein
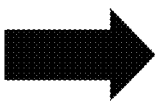
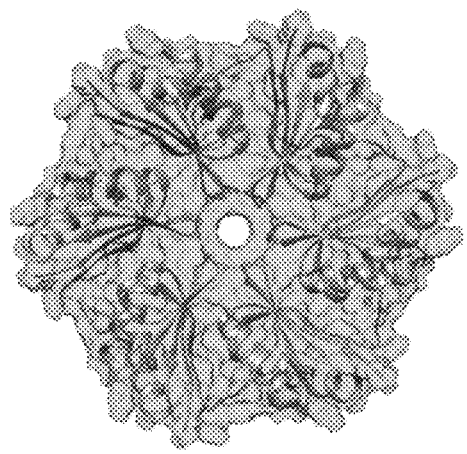
Assembly of subunits into hexamer Shell formation Nanorod formation

FIG. 2

Single subunit of fusion shell protein

Assembly of fusion subunits into hexamer

Short Ubiquitin-related MOdifier / Ulp protease

FIG. 16A  FIG. 16B
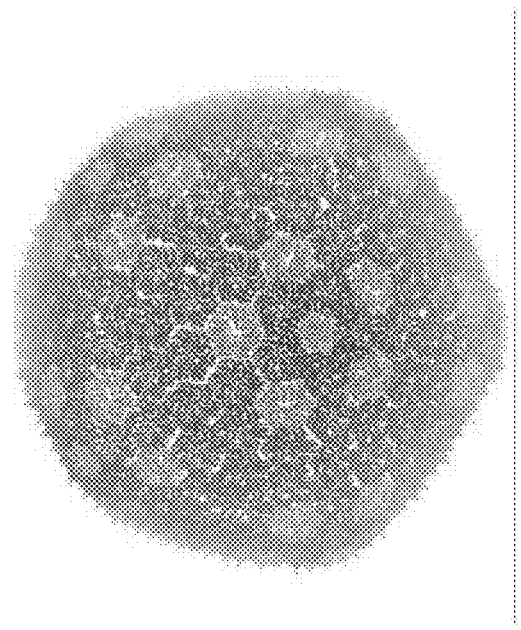
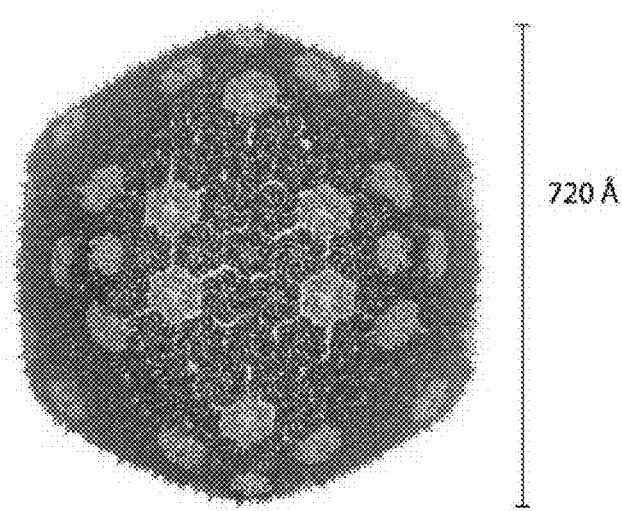
720 Å

FIG. 17
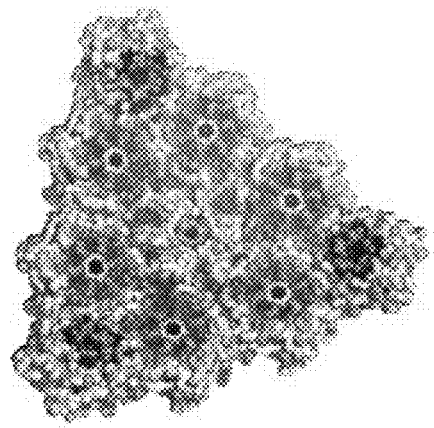
BMC-T1
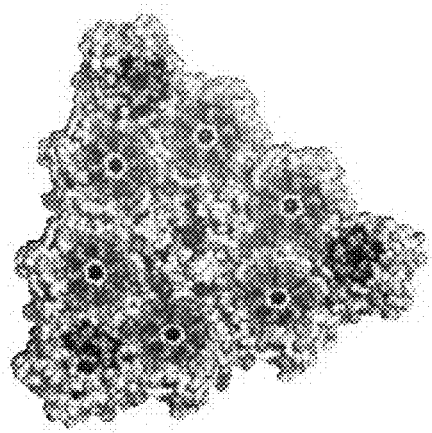
BMC-T2
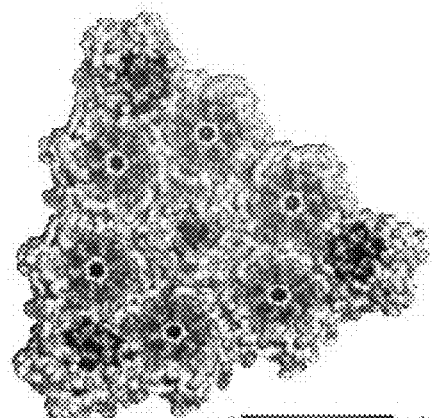
BMC-T3
-4 ▬▬▬ +4 kT/e

IN VITRO ASSEMBLY OF BACTERIAL MICROCOMPARTMENTS

CROSS-REFERENCE TO RELATED APPLICATIONS

This application claims the benefit of U.S. Provisional Application No. 62/509,553, filed May 22, 2017. The content of the aforementioned application is expressly incorporated herein by reference in its entirety.

STATEMENT OF GOVERNMENTAL SUPPORT

This invention was made with government support under Contract No. DE-AC02-05CH11231 awarded by the U.S. Department of Energy, under Grant No. 1R01AI114975-01 NIAID awarded by the U.S. National Institutes of Health, and under Contract No. DE-FG02-91ER20021 awarded by the U.S. Department of Energy, Basic Energy Sciences. The government has certain rights in the invention.

REFERENCE TO SEQUENCE LISTING

The present application is being filed along with a Sequence Listing in electronic format. The Sequence Listing is provided as a file entitled 2018-05-08 Sequence listing—LBNL.097A, created on Feb. 8, 2018, which is 29,549 bytes in size. The information in the electronic format of the Sequence Listing is incorporated herein by reference in its entirety.

BACKGROUND

Field

The present disclosure relates to synthetic biology, especially initiating and controlling in vitro assembly of bacterial microcompartments and integrating molecules into bacterial microcompartments.

Related Art

Bacterial microcompartments (BMCs) encapsulate enzymes, metabolic pathways, and functionally related reactions. BMCs serve to partition the cell's interior into unique microenvironments that endow their hosts with particular metabolic capabilities. BMC shell proteins and the components they encapsulate are typically found in gene clusters (putative operons). The shells of BMCs are generally comprised of multiple paralogs of proteins containing the BMC domain (e.g., Pfam00936) and presumably a relatively small number of proteins containing the Pfam03319 domain. Three types of shell proteins have been identified: single pfam00936 domains ("hexamer"), fusion proteins composed of two pfam00936 domains ("tandem domain"), and single pfam03319 domains ("pentamer"). Hexamer and tandem domain proteins are the major components of known microcompartment shells, while pentamer proteins are minor components. Natural BMC gene clusters vary widely in composition and gene arrangement and are defined by genes that encode shell proteins.

BRIEF SUMMARY

The present disclosure is related to in vitro assembly of bacterial microcompartments. One aspect relates to a fusion protein comprising (1) a BMC shell protein comprising one or more subunits and (2) one or more sterically hindering protein domains that are operably linked to the one or more subunits of the BMC shell protein, wherein the one or more sterically hindering protein domains are removable from the one or more subunits of the BMC shell protein; and wherein the BMC shell protein is capable of assembling in vitro when the one or more sterically hindering protein domains are removed from the one or more subunits of the BMC shell protein. In some embodiments, the BMC shell protein can assemble in vitro into a nanorod or another structure.

In some implementations, at least one of the one or more subunits of the BMC shell protein is one of Hoch_5815 (SEQ ID NO: 1), Hoch_5812 (SEQ ID NO: 3), Hoch_3341 (SEQ ID NO: 5), Hoch_5816 (SEQ ID NO: 7), Hoch_4425 (SEQ ID NO: 9), Hoch_4426 (SEQ ID NO: 11), Hoch_5814 (SEQ ID NO: 13), PduA (SEQ ID NO: 15), YP_884690 (SEQ ID NO: 17), EutN (SEQ ID NO: 19), CcmK2 (SEQ ID NO: 21), CcmO (SEQ ID NO: 23), and CcmL (SEQ ID NO: 25).

In some implementations, the one or more sterically hindering protein domains are one of Maltose Binding Protein (MBP), Short Ubiquitin-related Modifier (SUMO) protein, and their orthologs. In some implementations, the sterically hindering protein is removable from the BMC shell protein by a protease. In some implementations, the protease is one of TEV protease, Ulp protease, and the fragments thereof. Some implementations further comprise a linker polypeptide operably linking between the BMC shell protein and the sterically hindering protein. In some implementations, the linker polypeptide is specifically cleavable by a protease.

Another aspect relates to a polynucleotide encoding a heterologous fusion protein in a host organism, comprising: a first nucleotide sequence that encodes a BMC shell protein subunit or fragment thereof; a second nucleotide sequence that encodes a sterically hindering protein domain or fragment thereof; and a promoter sequence operably linked to the first nucleotide sequence and the second nucleotide sequence, the promoter sequence configured to drive expression in the host organism; wherein the sterically hindering protein domain is removable from the BMC shell protein subunit; and wherein the BMC shell protein subunit is capable of assembling in vitro when the sterically hindering protein domain is removed from the BMC shell protein subunit.

In some implementations, the host organism is *E. coli, B. subtilis, S. cerevisiae*, cyanobacteria, plants, or algae. In some implementations, the BMC shell protein subunit is one of Hoch_5815 (SEQ ID NO: 1), Hoch_5812 (SEQ ID NO: 3), Hoch_3341 (SEQ ID NO: 5), Hoch_5816 (SEQ ID NO: 7), Hoch_4425 (SEQ ID NO: 9), Hoch_4426 (SEQ ID NO: 11), Hoch_5814 (SEQ ID NO: 13), PduA (SEQ ID NO: 15), YP_884690 (SEQ ID NO: 17), EutN (SEQ ID NO: 19), CcmK2 (SEQ ID NO: 21), CcmO (SEQ ID NO: 23), and CcmL (SEQ ID NO: 25). Some implementations further comprise a ribosome binding site sequence that controls expression efficiency in the host organism. In some implementations, the ribosomal binding site sequence is derived from *Escherichia coli* or *Halothiobacillus neapolitanus*.

Some implementations further comprise an affinity tag linked to the first nucleotide sequence or the second nucleotide sequence. In some implementations, the affinity tag is polyhistidine. In some implementations, the first nucleotide sequence and the second nucleotide sequence are joined to one another through a linker sequence that encodes a linker polypeptide. In some implementations, the linker polypeptide is specifically cleavable by a protease. In some implementations, the promoter sequence is an inducible promoter sequence. Some implementations further comprise a selectable marker gene. In some implementations, the selectable marker gene is one of an antibiotic resistance gene, a β-galactosidase gene, and a fluorescent protein.

Any feature, structure, or step disclosed herein can be replaced with or combined with any other feature, structure, or step disclosed herein, or omitted. Further, for purposes of summarizing the disclosure, certain aspects, advantages, and features of the embodiments have been described herein. It is to be understood that not necessarily any or all such advantages are achieved in accordance with any particular embodiment disclosed herein. No individual aspects of this disclosure are essential or indispensable. Further features and advantages of the embodiments will become apparent to those of skill in the art in view of the Detailed Description which follows when considered together with the attached drawings and claims.

BRIEF DESCRIPTION OF THE DRAWINGS

FIG. 1A shows the structure of an example of a single subunit of a BMC-H protein (hexamer shell protein) that can form into a hexamer assembly of BMC-H subunits.

FIG. 2 shows the structure of a single subunit of a fusion shell protein and a hexamer assembly of the fusion subunits.

FIG. 6A is collection of images that show surface representations and dimensions of a side view (top row) and of the concave face (bottom row) of the structures of hexameric BMC-H (dark grey), trimeric BMC-T (light grey) and pentameric BMC-P proteins (light grey) that constitute the example shell. The BMC-T2 and BMC-T3 proteins each include two closely appressed pseudohexamers. The BMC-P structure was extracted from the whole shell structure, BMC-H and BMC-T1 from previously determined crystal structures (PDB IDs 5DJB and 5DIH, respectively) and BMC-T2 and BMC-T3 are crystal structures determined as described below. FIG. 6B shows a SDS-PAGE analysis of purified H. ochraceum BMC shells. FIG. 6C is an image overview of the 8.7 Å cryo electron microscopy structure shaded by shell protein. FIG. 6D depicts a surface representation of the crystal structure with a color gradient by distance from center (light to dark from inside to outside) (left) and cross-section through the center (right). FIG. 6E depicts a close-up of the icosahedral asymmetric unit (dashed line) with symmetry axes indicated with solid symbols, pseudo threefold symmetry with open triangles. Only one stack shown for the BMC-T.

FIG. 7A depicts a coplanar hexamer-hexamer interface connecting two pentamer vertices. FIG. 7B depicts a hexamer-hexamer interface as observed surrounding the pentamer. FIG. 7C depicts a hexamer-pentamer interface. FIG. 7D depicts a hexamer-pseudohexamer interface.

FIG. 9A depicts a pentamer-hexamer interface. The pentamer is shown in a slightly lighter shade of grey than other parts. Hexamer residues are shown in a slightly darker shade of grey with conservation indicated with asterisk(s). Different chains are indicated by color shading, dashed lines indicate hydrogen bonds. FIG. 9B depicts an angled hexamer-hexamer interface. FIG. 9C depicts a coplanar hexamer-hexamer interface.

FIG. 10A depicts a sample 2Fo-Fc density contoured at 1.0 sigma of a hexamer-pentamer interface. FIG. 10B depicts a 2Fo-Fc electron density of "inserting" arginine of PRPH motif contoured at 1.2 sigma.

FIG. 11A depicts an alignment of BMC-H representatives show a high structural conservation, shaded from darkest to lightest: *H. neapolitanus* CsoS1A, PDB ID 2EWH; *Synechocystis* sp 6803 CcmK2, PDB ID 2A1B; *M. smegmatis* MSM_0272, PDB ID 5L38; *E. coli* EutM, PDB ID 3I6P; *S. enterica* PduA, PDB ID 3NGK; and *H. ochraceum* BMC-H, PDB ID 5DJB. FIG. 11B depicts a structural alignment of, shaded from darkest to lightest: *H. neapolitanus* CsoS4A, PDB ID 2RCF; BMC-P representatives, *Synechocystis* sp 6803 CcmL, PDB ID 2QW7; *M. smegmatis* MSM_0273, PDB ID 5L37; *E. coli* EutN, PDB ID 2Z9H (only one chain shown, forms hexamers in crystal); and *H. ochraceum* BMC-P, from shell structure. FIG. 11C depicts an alignment of the *H. ochraceum* BMC-H in the shell structure (dark grey) with the crystal structure of the isolated protein (lighter grey, PDB ID 5DJB). FIG. 11D depicts a structural alignment of the *H. ochraceum* hexamer (grey) with the BMC-T proteins (BMC-T1 (light grey) and BMC-T2 (dark grey—only slightly darker than the *H. ochraceum* hexamer). For the superposition, only one chain of the BMC-T was chosen to minimize deviation instead of an overall alignment.

FIG. 14A depicts a detailed view of the two different interfaces of the BMC-T2:BMC-H contacts. FIG. 14B depicts a structure based sequence alignment of the three BMC-T proteins present in the *H. ochraceum* shell. KAA and PRPH motif equivalent positions are highlighted in FIG. 14A and FIG. 14B separate shading. BMC-T2 and BMC-T3 are circularly permuted with regards to the standard BMC motif so that the C-terminal part of each BMC-T1 is moved to the N-terminus; the initiating methionine is highlighted with a circle. Numbering follows BMC-T2 and corresponds to the structure in FIG. 14A.

FIG. 15A shows a single stacking PduT/BMC-T1 type. FIG. 15B shows amdouble stacking CcmP/CsoS1D/BMC-T2 or BMC-T3 type. Regions corresponding to the PRPH and KAA motifs are highlighted with boxes. Positions of the *H. ochraceum* shell proteins BMC-T1, BMC-T2 and BMC-T3 on the trees are indicated.

FIGS. 16A and 16B are images, each showing separate views of a model of a T=36 icosahedral BMC shell with 290 BMC-H hexamers, 60 BMC-T pseudohexamers and 12 BMC-P pentamers constructed from the proteins and interactions observed in the *H. ochraceum* model. The resulting shell is 720 Å in diameter and approximately 22 MDa in mass.

FIG. 17 is a set of three images that shows an influence of BMC-T type on inside surface properties. The images include electrostatic surface views of the inside facets with different BMC-T proteins modelled in the centers. The three different BMC-T proteins show distinct surface shape and charge distribution. Color gradient from −4 kT/e (gray) to +4 kT/e (dark grey).

FIG. 18A is a sample electron micrograph. *H. ochraceum* shells are clearly visible as near-spherical particles. FIG. 18B graphically depicts a FSC curve of the final reconstruction of the shell, indicating a resolution of 8.7 Å according to the FSC=0.143 criterion. FIG. 18C depicts a data processing and classification strategy used for reconstruction of the *H. ochraceum* shell structure. The reconstructions are shaded using a gradient based on radius, revealing that the concave surface of the BMC-H subunits is exposed and highlighting the protruding BMC-T subunits (dark grey). The final reconstruction was sharpened for visualization using a b-factor of −1256, as determined by the post-processing function of RELION.

DETAILED DESCRIPTION

Figure 1B:
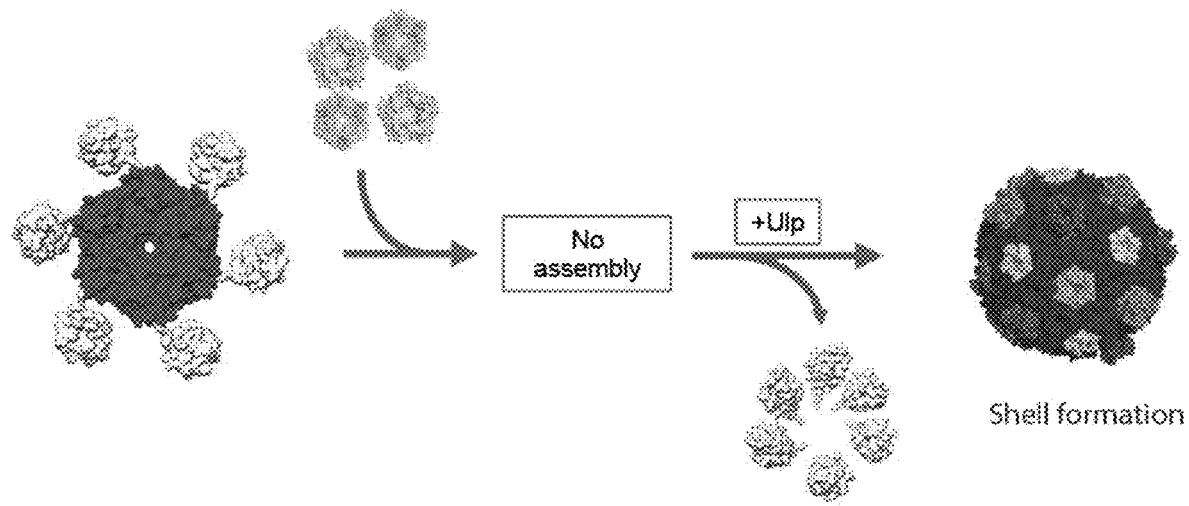
FIG. 1B is a depiction of BMC-H forming a shell structure.

Some embodiments of the invention relate to bacterial microcompartments (BMCs) that are used to encapsulate functionally related proteins. The bacterial microcompartment shell may be composed of multiple paralogs of proteins containing the BMC domain (Pfam00936) and presumably a relatively small number of proteins containing the Pfam03319 domain. There is recognizable sequence homology among the >2000 BMC domains in the sequence databases, suggesting that despite functional diversity and some differences in the morphology of a specific bacterial microcompartment type, there are conserved structural determinants for targeting and binding of the enzymes and auxiliary proteins that are encapsulated in BMCs.

In some embodiments, BMC proteins or BMC fusion proteins assemble into shells, nanoshells, rods, nanorods, or other structures. Some embodiments relate to the formation of shells in vitro, although other embodiments relate to BMC formation in vivo.

BMC shell proteins and the components they encapsulate are typically found in gene clusters (putative operons). Embodiments relate to the discovery of a common region of primary structure on a subset of the proteins presumed to be encapsulated in functionally diverse BMCs. In some embodiments, the common region is ~20 amino acids long and is located at either the N- or the C-terminus of encapsulated proteins, and in a few cases, in between domains of a single protein. This peptide may be separated from the rest of the protein by a poorly conserved linker region that is rich in small amino acids. The peptide and linker are present on numerous proteins presumed to be targeted to the interiors of 11 of the 15 types of BMCs; for the remaining 4 types of BMCs, the identity of the encapsulated proteins remains unknown, however a subset of these proteins are expected to contain a similar peptide for targeting.

One embodiment relates to systems and methods for producing BMC shells in vitro. This in vitro production of shells may be triggered by removal of a fused domain that comprises a sterically hindering domain that otherwise hinders the formation of shells in vitro. Once the sterically hindering domain is cleaved from fused BMC shell proteins, it can lead to assembly of the constituent BMC shell proteins. Embodiments of the invention relate to a BMC fusion protein that is capable of in vitro assembly triggered by removal of the fused, sterically hindering domain, and a system for in vitro assembly of BMC shells triggered by removal of the sterically hindering domain. The BMC fusion protein and the system enable encapsulation of broad classes of materials and biophysical studies of shell assembly, encapsulation, and permeability that would otherwise be unavailable from BMCs assembled in vivo.

Definitions

The term "amphipathic alpha helix" or "amphipathic α helix" refers to a polypeptide sequence that can adopt a secondary structure that is helical with one surface, i.e., face, being polar and comprised primarily of hydrophilic amino acids (e.g., Asp, Glu, Lys, Arg, His, Gly, Ser, Thr, Cys, Tyr, Asn and Gln), and the other surface being a nonpolar face that comprises primarily hydrophobic amino acids (e.g., Leu, Ala, Val, Ile, Pro, Phe, Trp and Met) (see, e.g., Kaiser and Kezdy, *Ann. Rev. Biophys. Chem.* 16: 561 (1987) and *Science* 223:249 (1984)).

The term "bacterial microcompartment" as used herein is intended to describe and include genes with sequence or structural homology to the conserved bacterial microcompartment domains pfam00936 and/or pfam03319 along with any other genes that are associated or identifiable as in a gene cluster with these pfam00936 and/or pfam03319 homologs or are implicated microcompartment proteins by co-regulation with microcompartment genes and may encode proteins and/or enzymes having metabolizing activity. The term "gene cluster" or "cluster" or "cluster or genes" as used herein is intended to describe and include genes which are contiguous and generally not separated by more than about 300 bp from one another, but may include some genes which are distal in a genome but co-regulated or co-expressed with the genes found in the gene cluster. While many of the bacterial microcompartments are found in contiguous gene clusters, it is recognized that there may be multiple clusters within a genome, or alternatively, or in addition, many organisms having gene clusters may also have scattered isolated genes that may also be co-regulated and can be incorporated into the bacterial microcompartment. The scattered genes may have been more recently acquired as it may be that once a bacterium acquires a BMC gene cluster, it can readily pick up and retain genes that could be co-expressed in the microcompartment although the gene may physically reside elsewhere in the genome.

In one embodiment, the cluster of genes containing one or more occurrences of Pfam00936 and/or Pfam03319 wherein all contiguous genes are not greater than about 300 bp from one another or are distal in the genome (including in plasmids), but co-regulated/expressed with bacterial microcompartment genes. Thus, in another embodiment, an expression cassette comprising a nucleic acid molecule comprising a cluster of bacterial compartment genes. The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Amino acid polymers may comprise entirely L-amino acids, entirely D-amino acids, or a mixture of L and D amino acids. The use of the term "peptide or peptidomimetic" in the current application merely emphasizes that peptides comprising naturally occurring amino acids as well as modified amino acids are contemplated. Polypeptides of some embodiments can be produced either from a nucleic acid disclosed herein, or by the use of standard molecular biology techniques. For example, a truncated protein of some embodiments can be produced by expression of a recombinant nucleic acid of some embodiments in an appropriate host cell, or alternatively by a combination of ex vivo procedures, such as protease digestion and purification, or in-vitro peptide synthesis. Generally an enzyme includes a protein having or exhibiting some metabolizing or catalytic activity.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In some embodiments, the term "purified" denotes that a nucleic acid or protein gives rise to essentially one band in an electrophoretic gel.

The terms "identical" or percent "identity," in the context of two or more polypeptide sequences (or two or more nucleic acids), refer to two or more sequences or subsequences that are the same or have a specified percentage of amino acid residues or nucleotides that are the same e.g., 60%, 65%, 70%, 75%, 80%, 85%, 90%, 91%, 92%, 93%, 94%, 95%, 96%, 97%, 98%, 99% or 100% identity over a specified region, when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are typically used.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, polypeptide-nucleic acids (PNAs). Unless otherwise indicated, a particular nucleic acid sequence also encompasses "conservatively modified variants" thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., *J. Biol. Chem.*, 260:2605-2608 (1985); Rossolini et al., *Mol. Cell. Probes*, 8:91-98 (1994)). The term "nucleic acid" can be used interchangeably with "gene," "cDNA," "mRNA," "oligonucleotide," and "polynucleotide."

An "expression vector" or "expression cassette" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

By "host cell" is meant a cell that contains an expression vector (e.g., plasmid) and supports the replication or expression of the expression vector. Host cells may be prokaryotic cells including but not limited to, *E. coli, B. subtilis, S. cerevisiae*, cyanobacteria including but not limited to, *Synechococcus elongatus*, or eukaryotic cells including but not limited to, yeast, plant, algae, insect, amphibian, or mammalian cells such as CHO, HeLa and the like, e.g., cultured cells, explants, and cells in vivo.

A "label" or "detectable label" is a composition detectable by spectroscopic, photochemical, biochemical, immunochemical, or chemical means. For example, useful labels include radioisotopes (e.g., $^3$H, $^{35}$S, $^{32}$P, $^{51}$Cr, or $^{125}$I), fluorescent dyes, electron-dense reagents, enzymes (e.g., alkaline phosphatase, horseradish peroxidase, or others commonly used in an ELISA), biotin, digoxigenin, or haptens and proteins for which antisera or monoclonal antibodies are available (e.g., a polypeptide can be made detectable, e.g., by incorporating a radiolabel into the polypeptide, and used to detect antibodies specifically reactive with the polypeptide).

"Pfam00936 domains" and "Pfam03319 domains" as used herein refer to proteins that are recognized as members of the protein families of those names in the pfam database (Website pfam.sanger.ac.uk). A "hexamer(s)" as used herein is a protein that contains a single pfam00936 domain. "Tandem domains" as used herein is a protein that contains two pfam00936 domains. A "pentamer" as used herein is a protein that contains a pfam03319 domain.

Any "gene" is meant to refer to the polynucleotide sequence that encodes a protein, i.e., after transcription and translation of the gene a protein is expressed. As understood in the art, there are naturally occurring polymorphisms for many gene sequences. Genes that are naturally occurring allelic variations for the purposes of this disclosure are those genes encoded by the same genetic locus. Thus, any "bacterial microcompartment gene", "microcompartment gene" as referred to herein is meant to include any polynucleotide that encodes a pfam00936 domain or Pfam03319 domain protein or variants thereof.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel.

As used herein in the specification and in the claims section that follows, the term "nucleic acid molecule" includes polynucleotides, constructs and vectors. The terms "construct" and "vector" may be used herein interchangeably.

Descriptions of Various Embodiments

Native BMC shell proteins (e.g., BMC shell proteins from a microbe such as *Haliangium ochraceum, Mycobacterium smegmatis*, and *Thermosynechococcus elongatus*), when present at sufficient concentrations, spontaneously assemble into high order assemblies and, subsequently, shells, tubes, layers, three-dimensional lattices and protein swiss rolls, among other architectures constructed from BMC shell proteins. This process is described in U.S. patent application Ser. No. 14/214,172, filed on Mar. 14, 2014, published as U.S. Patent Application Publication No. 2015/0026840 on Jan. 22, 2015 and U.S. patent application Ser. No. 15/367,089, filed Dec. 1, 2016, which are incorporated by reference in their entirety for all purposes.

A BMC fusion protein may comprises a fusion shell protein and additionally a sterically hindering protein domain. The fusion shell proteins may be from a microbe such as *Haliangium ochraceum, Halothiobacillus neapolitanus, Mycobacterium smegmatis, Thermosynechococcus elongates, Anabaena variabalis, Alkaliphilus metalliredigens, Bacteroides capillosus, Blastopirellula marina, Chloroherpeton thalassium, Clostridium kluveryi, Clostridium phytofermentans, Desulfatibacillum alkenivorans, Desulfotalea psychrophila, Desulfovibrio desulfuricans, Escherichia coli, Leptotrichia buccalis, Methylibium petroleiphilum, Opitutus terrae, Planctomyces limnophilus, Prochlorococcus marinus, Rhodopseudomonas palustris, Ruminococcus obeum, Salmonalla enterica, Salmonella typhimurium, Sebaldella termatidis, Shewanella putrefaciens, Synechocystis* sp. and *Thiomicrospira crunogena, Trichodesmium erythraeum*. The fusion shell proteins may be derived from natural BMC systems such as carboxysomes, propanediol utilization (pdu) compartments, which are involved in coenzyme B12-dependent degradation of 1,2-propanediol, and ethanolamine utilization (eut) compartments, which are involved in the cobalamin-dependent degradation of ethanolamine.

The fusion shell protein may be a pentamer, hexamer, or heptamer of identical subunits, depending on the type of BMC shell protein domain in the fusion shell protein. The fusion shell proteins may be one of the following proteins or protein domains: BMC-H, BMC-T, BMC-O, BMC-P, one or more pfam00936 domains, one or more pfam03319 domains, Ho-H (Hoch-H), Ho-T (Hoch-T), Ho-P (Hoch-P), Hoch_5815, Hoch_5812, Hoch_3341, Hoch_5816, Hoch_4425, Hoch_4426, Hoch_5814, CcmK, CcmK1, CcmK2, CcmK4, CcmL, CcmM, CcmN, CcmO, CcmP, CsoS1A, CsoS1C, CsoS1D, CsoS4A (OrfA), CsoS4B (OrfB), EutA, EutB, EutC, EutD, EutE, EutG, EutH, EutJ, EutK, EutL, EutN, EutP, EutQ, EutR, EutS, EutT, GRE, PduB, PduC, PduD, PduE, PduF, PduG, PduH, PduL, PduM, PduN, PduO, PduP, PduQ, PduS, PduT, PduU, PduV, PduW, PduX, PvmD, PvmE, PvmF, PvmH, PvmK, and PvmM. U.S. patent application Ser. No. 13/367,260, filed on Feb. 6, 2012, published as U.S. Patent Application Publication No. 2012/

0210459 on Aug. 16, 2012, which is incorporated by reference in its entirety for all purposes, describes native BMC shell proteins and DNA sequence encoding those proteins.

In one example, sequences of some *H. ochraceum* BMC shell proteins are listed below. All nucleic acid sequences provided herein are shown in the 5' to 3' direction.

```
YP_003270184 Protein (Hexamer; Hoch_5815; SEQ ID NO: 1)
MADALGMIEVRGFVGMVEAADAMVKAAKVELIGYEKTGGGYVTAVVRGDVA

AVKAATEAGQRAAERVGEVVAVHV1PRPHVNVDAALPLGRTPGMDKSA

YP_003270184 Gene (BMC-H; Hoch_5815; SEQ ID NO: 2)
ATGGCGGACGCACTGGGTATGATTGAAGTTCGTGGTTTTGTTGGTATGGTGGAAGCG

GCGGATGCTATGGTGAAAGCGGCTAAAGTTGAACTGATTGGTTATGAAAAAACCGG

CGGTGGCTACGTGACGGCAGTGGTTCGTGGTGATGTCGCAGCAGTTAAGGCAGCTA

CCGAAGCCGGTCAGCGTGCAGCAGAACGTGTTGGTGAAGTCGTGGCAGTTCATGTC

ATCCCGCGTCCGCACGTGAACGTTGATGCAGCTCTGCCGCTGGGTCGTACGCCGGGT

ATGGACAAAAGCGCGTAA

YP_003270181 Protein (BMC-T; Hoch_5812; SEQ ID NO: 3)
MDHAPERFDATPPAGEPDRPALGVLELTSIARGITVADAALKRAPSLLLMSRPVSSGKHL

LMMRGQVAEVEESMIAAREIAGAGSGALLDELELPYAHEQLWRFLDAPVVADAWEED

TESVIIVETATVCAAIDSADAALKTAPVVLRDMRLAIGIAGKAFFTLTGELADVEAAAEV

VRERCGARLLELACIARPVDELRGRLFF

YP_003270181 Gene (BMC-T; Hoch_5812; SEQ ID NO: 4)
ATGGACCACGCTCCGGAACGCTTTGATGCGACCCCGCCGGCAGGTGAACCGGACCG

CCCGGCACTGGGTGTGCTGGAACTGACCTCAATTGCTCGTGGTATCACCGTTGCGGA

TGCGGCCCTGAAACGTGCACCGAGTCTGCTGCTGATGTCCCGCCCGGTCAGCTCTGG

CAAGCATCTGCTGATGATGCGTGGCCAGGTGGCAGAAGTTGAAGAATCAATGATTG

CAGCTCGCGAAATCGCTGGTGCAGGTTCGGGTGCTCTGCTGGATGAACTGGAACTGC

CGTATGCGCACGAACAACTGTGGCGCTTTCTGGACGCACCGGTGGTTGCAGATGCAT

GGGAAGAAGACACCGAAAGCGTCATTATCGTGGAAACCGCGACGGTGTGCGCGGCC

ATTGATAGTGCCGACGCAGCTCTGAAAACGGCACCGGTCGTGCTGCGTGATATGCGC

CTGGCCATTGGTATCGCTGGCAAGGCGTTTTTCACCCTGACGGGTGAACTGGCAGAC

GTGGAAGCGGCCGCAGAAGTTGTCCGTGAACGTTGCGGTGCACGTCTGCTGGAACT

GGCATGTATCGCACGCCCGGTTGATGAACTGCGTGGCCGCCTGTTTTTCTAA

YP_003267736 Protein (BMC-T; Hoch_3341; SEQ ID NO: 5)
MELRAYTVLDALQPQLVAFLQTVSTGFMPMEQQASVLVEIAPGIAVNQLTDAALKATR

CQPGLQIVERAYGLIEMHDDDQGQVRAAGDAMLAHLGAREADRLAPRVVSSQIITGIDG

HQSQLINRMRHGDMIQAGQTLYILEVHPAGYAALAANEAEKAAPIKLLEVVTFGAFGRL

WLGGGEAEIAEAARAAEGALAGLSGRDNRG

YP_003267736 Gene (BMC-T; Hoch_3341; SEQ ID NO: 6)
ATGGAACTGCGTGCTTATACGGTCCTGGATGCCCTGCAGCCGCAACTGGTCGCCTTT

CTGCAAACGGTGTCAACGGGTTTCATGCCGATGGAACAGCAAGCGAGCGTTCTGGT

CGAAATTGCACCGGGTATCGCTGTCAACCAGCTGACCGACGCAGCACTGAAAGCAA

CGCGTTGCCAGCCGGGTCTGCAAATTGTGGAACGTGCGTATGGCCTGATCGAAATGC

ATGATGACGATCAGGGTCAAGTTCGTGCAGCTGGTGACGCAATGCTGGCACACCTG

GGTGCACGTGAAGCTGATCGTCTGGCACCGCGTGTGGTTAGCTCTCAGATTATCACC

GGTATTGACGGCCATCAGAGTCAACTGATCAACCGTATGCGCCACGGTGATATGATT

CAGGCAGGCCAAACGCTGTATATCCTGGAAGTTCATCCGGCAGGTTACGCAGCACT
```

```
GGCAGCTAATGAAGCCGAAAAAGCGGCCCCGATTAAGCTGCTGGAAGTCGTGACCT

TTGGTGCATTCGGTCGTCTGTGGCTGGGTGGTGGTGAAGCAGAAATCGCAGAAGCA

GCTCGTGCGGCAGAAGGTGCACTGGCTGGTCTGTCCGGCCGTGATAATCGCGGCTAA
```

YP_003270185 Protein (BMC-T; Hoch_5816; SEQ ID NO: 7)
```
MSITLRTYIFLDALQPQLATFIGKTARGFLPVPGQASLWVEIAPGIAINRVTDAALKATKV

QPAVQVVERAYGLLEVHHFDQGEVLAAGSTILDKLEVREEGRLKPQVMTHQIIRAVEA

YQTQIINRNSQGMMILPGESLFILETQPAGYAVLAANEAEKAANVHLVNVTPYGAFGRL

YLAGSEAEIDAAAEAAEAAIRSVSGVAQESFRDR
```

YP_003270185 Gene(BMC-T; Hoch_5816; SEQ ID NO: 8)
```
ATGTCAATCACCCTGCGCACCTATATCTTTCTGGACGCCCTGCAACCGCAACTGGCA

ACCTTCATCGGCAAAACGGCTCGTGGCTTCCTGCCGGTCCCGGGTCAGGCAAGCCTG

TGGGTGGAAATTGCTCCGGGTATTGCGATCAACCGTGTGACCGATGCGGCCCTGAAA

GCTACGAAGGTGCAGCCGGCGGTTCAAGTGGTTGAACGCGCGTATGGCCTGCTGGA

AGTTCATCACTTCGATCAGGGCGAAGTCCTGGCAGCTGGTAGTACCATCCTGGACAA

ACTGGAAGTTCGTGAAGAAGGTCGCCTGAAGCCGCAGGTGATGACCCATCAAATTA

TCCGTGCTGTTGAAGCGTATCAGACGCAAATTATCAACCGCAATAGTCAGGGCATGA

TGATTCTGCCGGGTGAATCCCTGTTTATCCTGGAAACCCAACCGGCAGGTTACGCAG

TCCTGGCAGCCAATGAAGCCGAAAAAGCAGCTAACGTTCACCTGGTCAATGTGACG

CCGTATGGCGCATTCGGTCGTCTGTACCTGGCCGGCTCAGAAGCAGAAATTGATGCG

GCCGCAGAAGCTGCGGAAGCCGCAATCCGCAGCGTTTCTGGTGTCGCGCAGGAATC

GTTTCGTGACCGCTAA
```

YP_003268812 Protein (BMC-P; Hoch_4425; SEQ ID NO: 9)
```
MYLGRVIGTVVAERKVAGLEGAKLLLVQPLDDALSPVGGVQAAVDTVQAGPDDLVYL

VGSREAALALTPSFVPVDAAIVGIVDDVHAPERAS
```

YP_003268812 Gene (BMC-P; Hoch_4425; SEQ ID NO: 10)
```
ATGTATCTGGGTCGTGTGATTGGTACCGTGGTGGCTGAACGCAAAGTGGCGGGTCTG

GAAGGCGCAAAACTGCTGCTGGTGCAACCGCTGGATGACGCACTGAGTCCGGTCGG

TGGTGTGCAGGCAGCAGTTGATACCGTCCAAGCAGGTCCGGATGACCTGGTGTATCT

GGTTGGTAGCCGTGAAGCAGCTCTGGCGCTGACGCCGTCTTTTGTGCCGGTTGATGC

GGCCATTGTCGGCATCGTTGATGACGTGCATGCACCGGAACGCGCTAGCTAA
```

YP_003268813 Protein (BMC-P; Hoch_4426; SEQ ID NO: 11)
```
MRLCRVLGSVVATVKHPVYNGLPLMIVQPLDDAGRDAGASFLAVDNVQSGPGDRVLV

LTEGGGVRQILALGDQVPIRSLIVGVVDAVDGVAATGVDDAGGAADSAAAAKSVRADE

LPADASAAGRGE
```

YP_003268813 Gene (BMC-P; Hoch_4426; SEQ ID NO: 12)
```
ATGCGTCTGTGTCGTGTTCTGGGCTCCGTCGTCGCCACCGTCAAGCACCCGGTCTAC

AATGG

TCTGCCGCTGATGATCGTTCAACCGCTGGATGACGCAGGTCGTGATGCAGGCGCTAG

TTTTCTGGCTGTTGATAACGTCCAGTCCGGTCCGGGTGACCGTGTCCTGGTGCTGACC

GAAGGTGGTGGTGTGCGTCAGATTCTGGCACTGGGTGATCAAGTCCCGATTCGCAGC

CTGATCGTGGGCGTGGTTGATGCAGTGGACGGTGTTGCAGCAACGGGTGTTGATGAC

GCAGGTGGTGCAGCTGATAGCGCAGCAGCAGCTAAATCTGTCCGTGCAGATGAACT

GCCGGCAGACGCAAGCGCGGCCGGTCGCGGCGAATAA
```

-continued

YP_003270183 Protein (BMC-P; Hoch_5814; SEQ ID NO: 13)
MVLGKVVGTVVASRKEPRIEGLSLLLVRACDPDGTPTGGAVVCADAVGAGVGEVVLY

ASGSSARQTEVTNNRPVDATIMAIVDLVEMGGDVRFRKD

YP_003270183 Gene (Pentamer; Hoch_5814; SEQ ID NO: 14)
ATGGTCCTGGGTAAAGTCGTGGGTACGGTGGTGGCGAGCCGCAAAGAACCGCGCAT

TGAAGGTCTGAGCCTGCTGCTGGTCCGTGCCTGCGATCCGGACGGTACCCCGACGGG

TGGTGCAGTGGTTTGTGCAGATGCAGTGGGTGCAGGTGTTGGTGAAGTCGTGCTGTA

TGCGAGTGGCAGCTCTGCCCGTCAGACCGAAGTCACGAACAATCGCCCGGTTGATG

CAACCATTATGGCTATCGTTGACCTGGTCGAAATGGGCGGTGATGTGCGTTTTCGCA

AAGACTAA

In another example, sequences of some *M. smegmatis* BMC shell proteins are listed below.

YP_884687 (PduA)
Protein sequence:
(SEQ ID NO: 15)
MSSNAIGLIETKGYVAALAAADAMVKAANVTITDRQQVGDGLVAVIVTG

EVGAVKAATEAGAETASQVGELVSVHVIPRPHSELGAHFSVSSK

DNA sequence:
(SEQ ID NO: 16)
ATGAGCAGCAATGCAATCGGTCTGATCGAAACGAAAGGCTATGTGGCGG

CACTGGCAGCGGCGGATGCAATGGTGAAGGCAGCAAATGTCACCATTAC

GGATCGTCAGCAAGTTGGCGACGGTCTGGTGGCGGTTATCGTCACCGGC

GAAGTGGGTGCCGTTAAAGCGGCCACCGAAGCAGGCGCTGAAACGGCAA

GTCAAGTGGGTGAACTGGTGTCCGTTCATGTCATTCCGCGTCCGCACAG

CGAACTGGGTGCACATTTTAGCGTTAGCTCTAAGTAA

YP_884690 (Microcompartments protein family protein)
Protein sequence:
(SEQ ID NO: 17)
MAELRSFIFIDRLQPQTMSYLGTWIKGALPRANMAAQIIEVAPGLDIEG

VTDVALKHAEVKAGILVVERQFGYLEFHGETGAVKAAADAALDYLGGDP

DAAVRPEILASRIISSIDHQHAFLINRNKIGSMVLPGESLFVLEVAPAS

YAILATNEAEKAADVKVVDFRMIGATGRVYLSGTEADVRQAADAARDAL

AVLQGA

DNA sequence:
(SEQ ID NO: 18)
ATGGCCGAACTGCGTAGCTTCATTTTCATTGACCGCCTGCAACCGCAAA

CGATGTCCTATCTGGGCACCTGGATTAAGGGTGCTCTGCCGCGTGCGAA

CATGGCGGCCCAGATTATCGAAGTTGCCCCGGGCCTGGATATTGAAGGT

GTTACCGACGTCGCCCTGAAACATGCAGAAGTCAAGGCTGGCATCCTGG

TGGTTGAACGCCAATTTGGTTATCTGGAATTTCATGGCGAAACGGGTGC

GGTGAAAGCAGCTGCGGATGCCGCACTGGACTACCTGGGTGGTGATCCG

GACGCTGCAGTTCGTCCGGAAATTCTGGCCTCTCGCATTATCAGCTCTA

TCGATCATCAGCACGCATTTCTGATTAACCGTAATAAGATCGGCAGTAT

GGTCCTGCCGGGTGAATCCCTGTTCGTGCTGGAAGTTGCTCCGGCGAGC

TATGCGATTCTGGCGACCAATGAAGCGGAAAAAGCCGCAGATGTTAAGG

TCGTGGACTTTCGTATGATCGGTGCAACCGGTCGTGTCTACCTGTCGGG

CACGGAAGCTGATGTGCGTCAGGCTGCAGATGCAGCACGCGACGCACTG

GCAGTGCTGCAAGGTGCCTAA

YP_884688 (EutN)
Protein sequence:
(SEQ ID NO: 19)
MLRATVTGNVWSTRRIEGIPAGAFLEVEVEGTGSRMIAFDVLGSGVGEH

VLIAQGSVASSWFTGTPPPIDALIIGSIDTRSDSNPAE

DNA Sequence:
(SEQ ID NO: 20)
ATGCTGCGTGCTACCGTTACCGGCAATGTCTGGTCTACCCGTCGTATCG

AAGGCATCCCGGCTGGTGCTTTTCTGGAAGTGGAAGTCGAAGGCACCGG

TTCACGTATGATTGCCTTTGATGTCCTGGGCTCGGGTGTGGGCGAACAT

GTTCTGATCGCGCAGGGTAGCGTTGCCAGCTCTTGGTTCACCGGTACGC

CGCCGCCGATTGACGCACTGATTATCGGTAGTATCGATACGCGCAGTGA

CTCCAACCCGGCTGAATAA

In another example, the sequences of the *T. elongatus* BMC shell proteins are listed below.

CcmK2 Hexamer (BMC-H) carbon dioxide concentrating mechanism protein [*Thermosynechococcus elongatus* BP-1:NP_681737]
(SEQ ID NO: 21)
MPIAVGMIETRGFPAVVEAADAMVKAARVTLVGYEKIGSGRVTVIVRGDV

SEVQASVAAGVDSAKRVNGGEVLSTHIIARPHENLEYVLPIRYTEAVEQF

RN

Carbon dioxide concentrating mechanism protein [*Thermosynechococcus elongatus* BP-1: GI:22298490 (codon optimized)]
(SEQ ID NO: 22)
ATGCCAATTGCCGTGGGTATGATTGAAACCCGTGGTTTTCCAGCCGTGGT

GGAAGCGGCCGATGCCATGGTGAAAGCCGCGCGTGTTACCCTGGTGGGTT

ACGAGAAAATCGGTAGTGGTCGTGTGACCGTGATTGTGCGTGGTGATGTG

AGTGAAGTGCAAGCCAGTGTTGCGGCCGGTGTGGATAGTGCCAAACGTGT

GAATGGTGGCGAAGTGCTGAGTACCCATATCATTGCCCGTCCACATGAAA

ATCTGGAATACGTGCTGCCAATCCGTTACACCGAAGCCGTTGAACAATTT

CGTAAT

-continued

CcmO Tandem Domain (BMC-T)
Hypothetical protein tll1148 [*Thermosynechococcus elongatus* BP-1: NP_681938]
(SEQ ID NO: 23)
MERRDDFTDLALGLVSVQSFPAIVGIADHMLKSSDVLLVGYEKIGGGHCT

AIVRGRIADVRLAVEEGAERAQQFGQELSTLVIPRPDPNLEKILPIGSLL

AQIASKSRGHRLSSHAVGLLETRGFPAMVGAADAMLKAADVMLTAYETIG

AGLCTAIIRGTASNTAIALEAGMAEADRIGELHAVMLVPRPLEDLDQSLP

LAPALQRELQPLRLPLTLKQKETEPLALQGAAQASVAVEAAAERVPVDPP

ANP

Hypothetical protein tll1148 [*Thermosynechococcus elongatus* BP-1: GI:22298691 (codon optimized)]
(SEQ ID NO: 24)
ATGGAACGTCGTGATGATTTTACCGATCTGGCCCTGGGTCTGGTGAGTGT

GCAAAGTTTTCCGGCCATCGTGGGTATCGCCGATCATATGCTGAAGAGTA

GTGATGTGCTGCTGGTTGGTTACGAAAAAATCGGTGGTGGCCATTGCACG

GCGATCGTCGTGGTCGCATTGCGGACGTGCGCCTGGCGGTGGAAGAGGG

TGCCGAACGTGCCCAACAATTTGGTCAAGAACTGAGTACCCTGGTGATTC

CACGTCCAGATCCAAATCTGGAAAAGATTCTGCCGATTGGTAGTCTGCTG

GCGCAAATCGCGAGTAAAAGTCGTGGTCATCGTCTGAGCAGTCATGCCGT

TGGCCTGCTGGAGACCCGTGGTTTCCCAGCCATGGTGGGTGCGGCGGATG

CCATGCTGAAAGCGGCCGATGTGATGCTGACGGCCTACGAGACCATTGGT

GCCGGTCTGTGTACCGCCATCATTCGCGGCACGGCCAGTAATACCGCGAT

TGCCCTGGAAGCCGGTATGGCCGAAGCCGATCGTATTGGTGAACTGCATG

CGGTTATGCTGGTGCCACGCCCGCTGGAAGACCTGGATCAAAGTCTGCCG

CTGGCCCCAGCCCTGCAACGCGAGCTGCAACCACTGCGTCTGCCACTGAC

CCTGAAACAAAAAGAAACCGAGCCACTGGCGCTGCAAGGTGCCGCCCAAG

CCAGTGTGGCCGTTGAAGCCGCCGCCGAGCGTGTTCCAGTTGATCCGCCA

GCCAATCCA

CcmL Pentamer (BMC-P)
Carbon dioxide concentrating mechanism protein [*Thermosynechococcus elongatus* BP-1: NP_681735]
(SEQ ID NO: 25)
MKIARVCGTVTSTQKEDTLTGVKFLVLQYLGEDGEFLPDYEVAADTVGAG

QDEWVLSRGSAARHIINGTDKPIDAAVVAIIDTVSRDNYLLYSKRTQY

Carbon dioxide concentrating mechanism protein [*Thermosynechococcus elongatus* BP-1: GI:22298488 (codon optimized)]
(SEQ ID NO: 26)
ATGAAAATTGCCCGTGTGTGTGGTACCGTGACCAGTACCCAAAAAGAAGA

TACCCTGACCGGTGTGAAGTTTCTGGTGCTGCAATACCTGGGTGAAGATG

GTGAATTTCTGCCAGATTACGAAGTTGCGGCGGACACCGTTGGTGCCGGT

CAAGATGAATGGGTGCTGGTGAGTCGCGGTAGTGCCGCCCGTCACATTAT

CAATGGCACCGATAAACCAATTGATGCCGCCGTGGTGGCCATTATTGATA

CCGTTAGTCGTGATAATTACCTGCTGTATAGTAAACGTACCCAGTACTAA

Referring to FIG. 1A, when the fusion shell protein is in its native state (i.e., free standing and not fused to any other protein), the shell protein subunits assemble into a pentamer, hexamer, or heptamer, depending on the type of BMC shell protein domain. For example, six BMC-H subunits assemble into a hexamer (i.e., high order oligomerization). A number of the shell proteins can oligomerize into high-order structures such as a sheet or a shell. For example, a number of hexameric BMC-H shell proteins can oligomerize into sheets. If there are other types of BMC shell proteins as well as BMC-H, BMC shell proteins may form a complete shell structure.

Figure 1C:
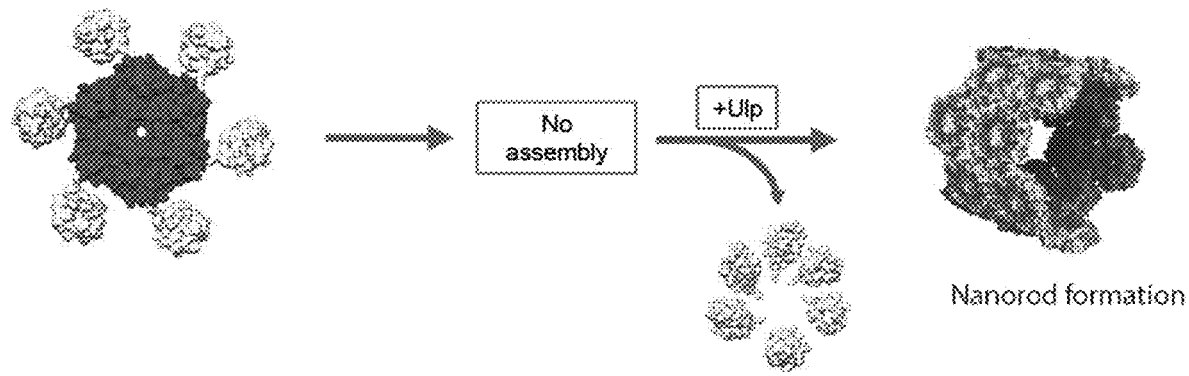
FIG. 1C is a depiction of BMC-H forming a nanorod structure.
Figure 1D:
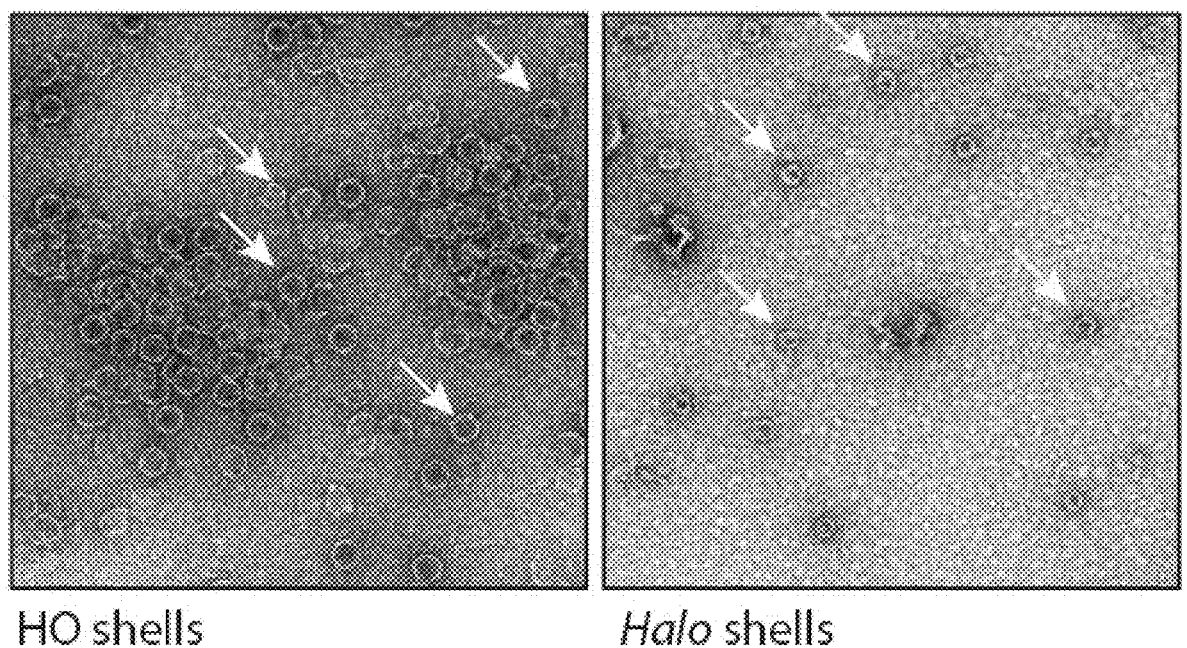
FIG. 1D is an image of two negative stain TEM images of in vitro assembled shells. HO shells are shown in the left panel. Halo shells are shown in the right panel. White arrows point to examples of shells.
Figure 1E:
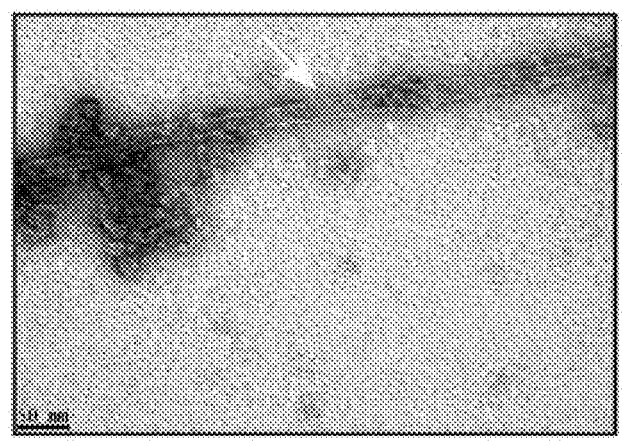
FIG. 1E is a TEM image of a negative stain of an in vitro assembled RmmH nanorod. The white arrow points to the nanorod.

FIGS. 1B-1E show an example of a strategy for in vitro assembly of shells and nanorods and transmission electron microscopy (TEM) of such assemblies. As shown in FIG. 1B, a sterically frustrated BMC-H may undergo assembly into shells in the presence of other shell proteins and with addition of a specific protease Ulp that removes a hindering domain. As shown in FIG. 1C, a sterically frustrated BMC-H domain may undergo assembly into nanorods upon cleavage with a specific protease, in this case Ulp. Images of in vitro assembled shells and nanorods are shown in FIGS. 1D-1E. Thus, according to some embodiments, a BMC protein or BMC fusion protein may assemble into a shell and/or a nanorod.

Referring to FIG. 2, a sterically hindering protein domain includes but is not limited to a Small Ubiquitin-like Modifier (SUMO) protein and its orthologs, and a Maltose Binding Protein (MBP) and its orthologs. The sterically hindering protein domain is removably fused to each subunit of the fusion shell protein. When attached to the fusion shell protein subunit, the sterically hindering protein domain precludes formation of high-order assemblies/oligomerization and shells of the BMC fusion protein. The sterically hindering protein domain may be removed from the fusion shell protein, such as through specific proteolytic cleavage. The sterically hindering protein domain may be removed by a specific protease such as Endoproteinase Trypsin, Chymotrypsin, Endoproteinase Asp-N, Endoproteinase Arg-C, Endoproteinase Glu-C, Endoproteinase Lys-C, Endoproteinase Lys-N, Pepsin, Thermolysin, Elastase, Papain, Proteinase K, Subtilisin, Clostripain, Exopeptidase Carboxypeptidase A, Carboxypeptidase B, Carboxypeptidase P, Carboxypeptidase Y, Cathepsin C, Acylamino-acid-releasing enzyme, Pyroglutamate aminopeptidase, BNPS, NCS/urea, Caspase-1, Caspase-10, Caspase-2, Caspase-3, Caspase-4, Caspase-5, Caspase-6, Caspase-7, Caspase-8, Caspase-9, CNBr, Enterokinase (EK), Factor Xa, Formic acid, Granzyme B, HRV3C protease, Hydroxylamine, Iodosobenzoic acid, NBS, NTCB, Pancreatic elastase, Pepsin A, Prolyl endopeptidase, Proteinase K, TEV protease, Thermolysin, Thrombin, Ulp protease (also called SUMO protease), and fragments thereof.

The BMC fusion protein may have a linker between the fusion shell protein and the sterically hindering protein domain that has an amino-acid sequence targeted by a specific protease. This way, the sterically hindering protein domain may be removed from the fusion shell protein when the specific protease is added to the BMC fusion protein. In some embodiments, inclusion of the sterically hindering domain that is removable allows one to combine BMC fusion proteins at high concentrations, sufficient for self-assembly, and then selectively trigger shell assembly via removal of the hindering domain.

The BMC fusion protein may further have an affinity tag, such as Albumin-binding Protein (ABP), Alkaline Phosphatase (AP), AU1 epitope, AU5 epitope, Bacteriophage T7 epitope (T7-tag), Bacteriophage V5 epitope (V5-tag), Biotin-carboxy carrier protein (BCCP), Bluetongue virus tag (B-tag), Calmodulin binding peptide (CBP), Chloramphenicol Acetyl Transferase (CAT), Cellulose binding domain (CBP), Chitin binding domain (CBD), Choline-binding domain (CBD), Dihydrofolate reductase (DHFR), E2 epitope, FLAG epitope, Galactose-binding protein (GBP), Green fluorescent protein (GFP), Glu-Glu (EE-tag), Glutathione S-transferase (GST), Human influenza hemagglutinin (HA), HaloTag, Histidine Affinity Tag (HAT), Horseradish Peroxidase (HRP), HSV epitope, Ketosteroid isomerase (KSI), KT3 epitope, LacZ, Luciferase, Maltose-binding protein (MBP), Myc epitope, NusA, PDZ domain, PDZ ligand, Polyarginine (Arg-tag), Polyaspartate (Asp-tag), Polycysteine (Cys-tag), Polyhistidine (His-tag), Polyphenylalanine (Phe-tag), Profinity eXact, Protein C, S1-tag, S-tag, Streptavadin-binding peptide (SBP), Staphylococcal protein A (Protein A), Staphylococcal protein G (Protein G), Strep-tag, Streptavadin, Small Ubiquitin-like Modifier (SUMO), Tandem Affinity Purification (TAP), T7 epitope, Thioredoxin (Trx), TrpE, Ubiquitin, Universal, and/or VSV-G. The affinity tag may be attached to either the fusion shell protein or the sterically hindering protein domain. The affinity tag may be used for purification of the BMC fusion protein, for example, when the BMC fusion protein is expressed from host cells. The affinity tag may be used for purification of the fusion shell protein or separation of the sterically hindering protein domain, for example, after the sterically hindering protein domain is removed from the fusion shell protein. The BMC fusion proteins, the fusion shell proteins, and/or the sterically hindering protein domains may be purified with immobilized metal affinity chromatography (IMAC) and ion-exchange chromatography (e.g., AIEX, CIEX), or any combinations thereof.

In one embodiment, BMC fusion proteins are selected to be synthesized and/or engineered in a host cell. A polynucleotide encoding the BMC fusion proteins can be inserted into a host organism and if needed, expressed using an inducible expression system. When referring to the bacterial compartments or microcompartments, it is meant to include any number of proteins, shell proteins or enzymes (e.g., dehydrogenases, aldolases, lyases, etc.) that comprise or are encapsulated in the compartment.

In one embodiment, polynucleotides encoding BMC fusion proteins, are cloned into an appropriate plasmid, inserted into an expression vector, and used to transform cells from any host organism. Suitable host organisms include, but are not limited to, bacteria such as *E. coli*, *B. subtilis*, *S. cerevisiae*, cyanobacteria such as *S. elongatus*, plants such as *Nicotiana tabacum* and *Camelina sativa*, algae, fungi, or other eukaryotic organisms.

In one embodiment, an in vitro transcription/translation system (e.g., Roche RTS 100 *E. coli* HY) can be used to produce cell-free microcompartments or expression products.

Where appropriate, the polynucleotides may be optimized for increased expression in the transformed organism. For example, the polynucleotides can be synthesized using preferred codons for improved expression.

In some embodiments, additional sequence modifications are included that enhance gene expression in a cellular host. For example, these may include elimination of sequences encoding spurious polyadenylation signals, exon-intron splice site signals, transposon-like repeats, and/or other sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In one embodiment, the polynucleotides are in an inducible expression system which maintains the expression of the inserted genes silent unless an inducer molecule (e.g., IPTG) is added to the medium containing the host cell. The expression vector or construct may be a vector for co-expression or in some embodiments, it may be a neutral site vector for insertion into a host genome such as *Synechococcous elongatus*. The construct may include either inducible transcription elements or may be constitutively expressed in the host organism.

In some embodiments, bacterial colonies are allowed to grow after gene expression has begun, or if required, after induction of gene expression. Thus, in some embodiments, expression vectors comprising a promoter operably linked to a heterologous nucleotide sequence or a fragment thereof, that encodes a microcompartment RNA or proteins are further provided. The expression vectors of the invention find use in generating transformed plants, plant cells, microorganisms, algae, fungi, and other eukaryotic organisms as is known in the art and described herein. The expression vector may include 5' and 3' regulatory sequences operably linked to a polynucleotide of the disclosure. "Operably linked" is intended to mean a functional linkage between two or more elements. For example, an operable linkage between a polynucleotide of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The vector may additionally contain at least one additional gene to be co-transformed into the organism. Alternatively, the additional gene(s) can be provided on multiple expression vectors or cassettes. Such an expression vector is provided with a plurality of restriction sites and/or recombination sites for insertion of the polynucleotide that encodes a microcompartment RNA or polypeptide to be under the transcriptional regulation of the regulatory regions.

The expression vector can also comprise a selectable marker gene for the selection of transformed cells. Selectable marker genes are utilized for the selection of transformed cells or tissues. In some embodiments, marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). The above list of selectable marker genes is not meant to be limiting. Any selectable marker gene can be used in the present disclosure.

In one embodiment, the system for in vitro assembly of BMC shells comprises a construct expressing the BMC fusion protein described above. The construct may be derived from an expression vector including but not limited to pALTER, pBAD, pBADM, pBAT, pCal, pET, pET-11, pET-23b, pETM, pDUAL, pGEMEX, pGEX, pHAT, pLEX, pQE, pMal, pCOLA-DUET-1, and pProEx. The construct may have a promoter including but not limited to lac, lacUV5, tac, trc, trp, araBAD, phoA, recA, proU, cst-1, pL, T7, T7-lac operator, T3-lac operator, T5-lac operator, T4 gene 32, nprM-lac operator, VHb, Protein A, tetA, cadA, nar, cspA, pTet, pPro, Sp6, pLlacO1, pLtetO1, CMV, EF1a, SV40, PGK1, Ubc, human beta actin, CAG, TRE, UAS, Ac5, Polyhedrin, CaMKIIa, GAL1, GAL10, TEF1, GDS, ADH1, CaMV35S, Ubi, H1, and/or U6. The promoter may be an inducible promoter.

The expression vector may include in the 5'-3' direction of transcription, a transcriptional initiation region (i.e., a promoter), a cluster of bacterial compartment genes each preceded by a translational initiation site (RBS) specific to the organism and type of shell protein and followed by a translation termination signal (stop codon), and, optionally, a transcriptional termination region functional in the host organism. The regulatory regions (i.e., promoters, transcriptional regulatory regions, ribosomal binding sites and translational termination regions) and/or any targeting sequences may be native or analogous to those found in the host cell or to each other. Alternatively, the regulatory regions and/or the targeting regions may be heterologous to the host cell or to each other. As used herein, "heterologous" in reference to a sequence that originates from a foreign species, or, if from the same species, is modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

In various embodiments, the construct may further comprise a ribosome binding site sequence that is specific for the host cell, wherein the ribosomal binding site sequence is placed in the construct adjacent and precedent to a bacterial compartment gene described above so as to control the translation efficiency of the gene it precedes. The ribosomal binding site sequence may be derived from bacterial cells such as *Escherichia coli* or *Halothiobacillus neapolitanus*.

Ribosomal binding sites (RBS) are sequences that precede the coding region of a gene whereby the RBS allows the ribosome to bind the transcript and initiate translation. Ribosomal binding site sequences have been found in various organisms and control and are used in some embodiments to vary translation start efficiency in organisms. For example in *E. coli* and/or other bacteria, the sequence of TTTAGAGAAAGAGGAGAAATACTAG (SEQ ID NO: 27, high RBS) is a high ribosomal binding site (RBS) sequence which means that any gene directly following this sequence (i.e., directly 3'- to this sequence) is generally translated at a higher rate. This is turn may provide for more or greater expression levels of the protein encoded by the gene which follows a high RBS sequence. Likewise other sequences are known to promote a medium or low translation efficiency in *E. coli* or other bacteria, such as TTTAGAGATTAAAGAGGAGAAATACTAG (SEQ ID NO: 28, medium RBS) and TTTAGAGTCACACAGGAAACCTACTAG (SEQ ID NO: 29, low RBS).

Therefore, in various embodiments, to produce a BMC shell in a new host organism, a synthetic operon is constructed that contains the desired shell proteins. For each individual protein, an RBS is selected depending on the type. For example, hexamers (BMC-H) are given an RBS with the highest level of translation initiation. Tandem domains are given an RBS at a reduced level of translation initiation (for example, 60% of the predicted value for hexamers). In another example, pentamers are given an RBS with the lowest level of translation initiation (for example, 5% of the predicted value for hexamers. Thus, in some embodiments, the expression vector might further comprise high, medium and/or low ribosomal binding site sequences for a host organism that are inserted in the vector adjacent to and preceding various bacterial compartment genes in the cluster.

RBS sequences may be obtained from various sources. They may be designed, for example, by using a calculation to predict translation initiation rates (e.g., Salis, H. M. (2011) The Ribosome Binding Site Calculator, *Methods in Enzymology* 498: 19-42). RBS sequences may be selected from DNA sequences of natural organisms (e.g. the natural RBS site from the *H. neapolitanus* shell protein CsoS1C, GATTTTGAATGAGTCTTTATTGAGGAGAGAAGAA (SEQ ID NO: 30)). RBS sequences may also be used from databases of biological sequences, including the Community RBS Collection of the Registry of Standard Biological Parts (http://partsregistry.org).

Examples of RBS sequences are as follows:

```
                                         (SEQ ID NO: 31)
     TCTAGAAATAATTTTGTTTAGAGAAAGAGGAGAAATACTAG (SEQ ID NO: 32)
     TTTAGAGATTAAAGAGGAGAAATACTAG (SEQ ID NO: 33)
     TTTAGAGTCACACAGGAAACCTACTAG (SEQ ID NO: 34)
     TTTTGTTTAGAGAAAGAGGAGAAATACTAG

B1010 ribosome binding site:
                                         (SEQ ID NO: 35)
     T TTAAGA AGGAGA TATACC B1001 ribosome binding site:
                                         (SEQ ID NO: 36)
     GG CTAACA TAGGGT GGATCT (SEQ ID NO: 37)
     TCTAGAGAAAGAGGAGAAATACTAGATG (SEQ ID NO: 38)
     TCTAGAGATTAAAGAGGAGAAATACTAGATG (SEQ ID NO: 39)
     TCTAGAGTCACACAGGAAACCTACTAGATG
```

U.S. patent application Ser. No. 14/214,172, filed on Mar. 14, 2014, published as U.S. Patent Application Publication No. 2015/0026840 on Jan. 22, 2015 and U.S. patent application Ser. No. 15/367,089, filed Dec. 1, 2016, which are incorporated by reference in their entirety for all purposes, describe ribosome biding sites that may be used in a BMC shell expression construct.

The construct may be inserted and expressed in a host cell, which may be either prokaryotic or eukaryotic. Examples of host cells include *E. coli, B. subtilis, S. cerevisiae*, cyanobacteria, plants, and algae. The BMC fusion proteins may be purified with immobilized metal affinity chromatography and ion-exchange chromatography, or any combinations thereof.

In some embodiments, purified fusion proteins are combined at the appropriate stoichiometric ratio in a buffer which allows for proper function of the protease. In some embodiments, upon addition of and incubation with the protease, the sterically hindering protein domain is proteolytically removed, and the concentrated BMC shell proteins in their native form assemble into shells, stochastically encapsulating any material also present in the bulk solvent.

Where materials are encapsulated by BMCs in a stochastic manner, both biological and non-biological materials may be encapsulated by BMCs.

Finer kinetic and temporal control over BMC assembly is possible when different BMC shell proteins are fused to different sterically hindering protein domains and only liberated when their respective protease is added. When more than one kind of the fusion proteins, each of which is cleavable by a different kind of protease, are used, BMC assembly can be controlled by changing the timing of when each different type of protease is added. For example, composite materials comprising different shell protein layers may be built up from a sequential deposition of discrete shell proteins, each fused to a unique sterically hindering protein domain (e.g., different SUMO variants) and proteolysed at an appropriate time by its respective protease.

In one embodiment, selected microcompartment genes are placed onto the construct using the following general strategy. DNA sequence encoding a sterically hindering domain and one or more single pfam00936 domains ("hexamers") and their RBS sequences are placed first in the synthetic operon. Then, DNA sequence encoding a sterically hindering domain and one or more tandem pfam00936 domains ("tandem domains") and their RBS sequences are placed in the synthetic operon. Finally, DNA sequence encoding a sterically hindering domain and one or more pfam03319 domains ("pentamer domains") and their RBS sequences are placed. Therefore, in various embodiments, an expression vector comprising a transcription start site sequence, one or more nucleic acid sequences for BMC fusion protein genes and with ribosomal binding site sequences that are specific for the host cell, wherein the ribosomal binding site sequence is placed in the vector adjacent and directly 5'- to the BMC fusion protein genes.

Embodiments also include the encapsulation of any water-stable materials that are both biological and non-biological, such as small molecules, engineered nanomaterials, and quantum dots, nucleic acids, and magnetic particles. In one embodiment, proteins or other molecules may be introduced into synthetic microcompartments in vitro by mixing the cargo and the BMC fusion protein and adding to the mixture one or more proteases specific to the BMC fusion protein, which enzymatically cleave a sterically hindering domain from the BMC fusion protein so that the shell proteins re-assemble, thereby trapping the cargo to be encapsulated. Because the fusion proteins can be combined at high concentrations prior to assembly, the encapsulation efficiency (i.e., amount of target material encapsulated divided by the total amount of target material) of a given material according to the present disclosure would be significantly higher than a hypothetical alternative strategy of mixing native shell proteins together in vitro at low concentrations and then concentrating them to trigger assembly/encapsulation.

Furthermore, rather than depending on stochastic encapsulation of co-present materials, association of the materials with an encapsulation peptide may stoichiometrically target a material to the shell, thereby achieving even higher encapsulation efficiency. Genes that are encapsulated by the microcompartment may be targeted to the microcompartment by adding encapsulation tags specific for the microcompartment shell. Such encapsulation tags and the genes encoding the proteins to be encapsulated may be incorporated in the microcompartment expression vector itself or by co-expression of such encapsulation tagged genes which are on a second vector added to the host cell.

In one embodiment, a polynucleotide sequence encoding an encapsulation peptide or a fragment thereof as described can be inserted into the polynucleotide that encodes a protein of interest in the N-terminus or C-terminus or between functional domains of the proteins, thereby permitting the encapsulation of that protein into the BMC upon expression.

In other embodiments, proteins or other molecules may be incorporated into shells without using encapsulation tags by overexpressing proteins of interest, by electrostatic or hydrophobic or other types of protein-protein interactions that allow association of proteins with microcompartment shell protein, or by fusing proteins to other proteins that associate with shells. For example, an enzyme of interest could be fused to a Rubisco that interacts directly with a shell protein or an enzyme of interest could be directly fused to a shell protein.

Encapsulation peptides are primary structure extensions at the N- or C-termini (relative to homologs found in genomes lacking BMC loci), the extension contains a short region (15-20 amino acids) that is predicted to form an alpha helix by typical secondary structure prediction tools (e.g., JPRED; website: compbio.dundee.ac.uk/www-jpred/). This helix is separated from the functional domain of the protein by a poorly conserved and often low complexity linker. The helical conformation of an encapsulation peptide has recently been confirmed by NMR solution structure analysis (Lawrence, A. D., Frank, S., Newnham, S., Lee, M. J., Brown, I. R., Xue, W-F., Rowe, M. L., Mulvihill, D. P., Prentice, M. B., Howard, M. J. and Warren, M. J. Solution structure of a bacterial microcompartment targeting peptide and its application in the construction of an ethanol bioreactor. *ACS Synthetic Biology*). Examples of the encapsulation peptide and its DNA sequence include the following:

Encapsulation protein sequence fused to the N-terminus of an encapsulated protein (e.g., GFP) and derived from the N-terminus of an aldehyde dehydrogenase from *H. ochraceum*: MALREDRIAEIVERVLARL (SEQ ID NO: 40)

Encapsulation tag DNA sequence fused to the 5' end of the DNA sequence encoding the encapsulated protein (e.g., GFP):

```
                                       (SEQ ID NO: 41)
ATGGCACTGCGTGAAGATCGTATCGCTGAAATCGTGGAACGTGTCCTGGC
CCGTCTG
```

Encapsulation protein sequence fused to the C-terminus of an encapsulated protein (e.g., GFP): EPEDNEDVQAIVKAIMAKLNL (SEQ ID NO: 42)

DNA sequence fused to the 3' end of the DNA sequence encoding the encapsulated protein (e.g., GFP):

```
                                       (SEQ ID NO: 43)
GAACCGGAAGACAATGAAGATGTGCAGGCAATCGTGAAAGCAATTATGGC
TAAACTGAACCTG
```

Encapsulation protein sequence fused to the N-terminus of an encapsulated protein (e.g., aldolase) and derived from the *Haliangium ochraceum* targeting peptide found on the N-terminus of the aldolase gene: RDDLVRVIREELVRALA (SEQ ID NO: 44)

Encapsulation protein sequence fused to the N-terminus of an encapsulated protein (e.g., aldehyde dehydrogenase) and derived from the *Haliangium ochraceum* targeting peptide found on the N-terminus of the aldehyde dehydrogenase gene:

(SEQ ID NO: 45)
ALREDRIAEIVERVLARL

DNA sequence fused to the 5' end of the DNA sequence encoding the encapsulated protein (e.g., aldehyde dehydrogenase):

(SEQ ID NO: 46)
GCGCTGCGCGAAGATCGCATTGCGGAAATTGTGGAACGCGTGCTGGCGCG
CCTG

U.S. patent application Ser. No. 14/214,172, filed on Mar. 14, 2014, published as U.S. Patent Application Publication No. 2015/0026840 on Jan. 22, 2015 and U.S. patent application Ser. No. 15/367,089, filed Dec. 1, 2016, which are incorporated by reference in their entirety for all purposes, describe encapsulation peptides that target materials to BMC shells. Methods and compositions describing this in greater detail are described previously by some of the inventors in U.S. patent application Ser. No. 13/367,260 filed on Feb. 6, 2012, published as U.S. Patent Publication No. 2002/02104590 A1 ("Design and Implementation of Novel and/or Enhanced Bacterial Microcompartments for Customizing Metabolism"), and also described in Lassila, J. K., Bernstein, S. L., Axen S. D., Kinney J. N. and Kerfeld, C. A. Assembly of Robust Bacterial Microcompartment Shells using Building Blocks from an Organelle of Unknown Function. *Journal of Molecular Biology*, vol. 426, issue 11, 29 May 2014, pages 2217-2228, both of which are hereby incorporated by reference in their entirety.

In some embodiments, the synthetic BMC fusion proteins and microcompartments described herein can be used for a broad range of applications in biotechnology in addition to those described above, including as a scaffold for engineered vaccine constructs, as a vehicle for delivery of protein or small molecule drug agents, or as a capsule for stabilizing biocatalyst systems.

In other embodiments, the constructs for expressing BMC fusion proteins described herein may be used for delivery of proteins, biomolecules, drugs or other agents in another organism. In other embodiments, the present constructs and methods may be used to synthetically produce large quantities of the microcompartments encapsulating or incorporating the proteins, biomolecules, drugs or other agents, which after extraction are delivered to another organism needing treatment.

In another embodiment, the synthetic BMC fusion proteins and microcompartments described herein may be used to produce a synthetic carboxysome by incorporation of rubisco and carbonic anhydrase, and by engineering the pores for selective permeability for carbon fixation activity. In some embodiments, this expression construct could then be inserted into an organism such as bacteria, yeast or a plant such as Tobacco or Camelina.

In another embodiment, using an encapsulation tag or other approaches as listed above, a mechanism is provided for targeting biological molecules that would benefit from being compartmentalized and/or recombining them with other molecules and biological molecules within a bacterial microcompartment shell. This may enable the engineering of new or enhanced bacterial microcompartments. In yet another embodiment, the present disclosure allows one to engineer new metabolic modules (essentially organelles of specific function) into a host organism such as bacteria or a plant and provides a new approach to designing and optimizing catalysis in solution.

This strategy allows a fully synthetic and modular approach to design of new microcompartments or for production of existing microcompartments. An additional benefit of the present disclosure is that it may allow engineering of new pore selectivities by making amino acid substitutions at the perimeter of the pores. In some embodiments, the ability to alter the pore selectivities enables development of microcompartments as reaction chambers for a desired new or existing metabolic pathway.

In some embodiments, a hallmark feature of BMC that distinguishes them from other nanocompartments (e.g. lipid-bound vesicles and viruses) is a proteinaceous shell that is selectively permeable to small molecules. In some embodiments, the ability to encapsulate a broad range of material in such a shell as well as easily trigger and monitor assembly has diverse research, biomedical and cosmetic applications. Beyond BMCs, the general strategy of proteolytic removal of a hindering fusion domain in some embodiments is used in other self-assembling protein systems, for example, the in vitro assembly of the medically relevant virus-like particles (VLPs).

In some embodiments, facile in vitro shell assembly enables drug screens to identify compounds that prevent shell assembly or change permeability (e.g., via high-throughput, plate based fluorescence polarization assays or encapsulation of ligand-responsive probes). Pharmaceuticals that modulate BMC assembly or function may be used as therapeutic compounds. In some embodiments, BMCs serve as drug delivery devices wherein their cargo is activated/released in response to a specific chemical signal that selectively enters through the shell proteins' pores or even serve as de facto nanoreactors that could perform a specific metabolic function in a host organism.

Virus-like particles (VLPs), in some embodiments may be defined broadly as macromolecular assemblies of viral proteins, have been developed as a platform for vaccine development in recent years. Most VLPs are produced heterologously and are highly purified from contaminating host proteins to avoid undesired biological responses when used clinically. Furthermore, in vivo production of VLPs often leads to populations of heterogeneous size and shape, requiring in vitro disassembly/reassembly steps which negatively impact process development and cost. In some embodiments, production of de novo VLPs in vitro using the present disclosure facilitates economic production of VLPs by, for example, drastically reducing the number of contaminating proteins that in some embodiments are preferred to be removed from VLP preps (from an entire host's proteome to, at a minimum, the protease and undesired proteolytic products) as well as, for example, providing a potentially more efficient route to monodisperse preparations.

The behaviors of some catalysts are sensitive to their local environments and/or solution states. Enzymatic biocatalysis can be improved through scaffolding-based colocalization as well as through immobilization to inert carriers (e.g. solid supports or dispersed polymers) or via cross-linking. In some embodiments, the present disclosure provides a means to produce novel scaffolding topologies for both biological and inorganic catalysts—especially with temporal control of assembly through the use of cognate sterically hindering protein domain/protease pairs. In some embodiments, the selective permeability of shell proteins provides an additional layer of control in the catalytic system by, for example, excluding competing or poisonous reactants from interaction with the catalysts in analogy to the natural function of BMCs. In some embodiments, production of BMC shells and other architectures in vitro enables rapid screening of the proteins' permeability towards one or more libraries of small molecules. In some embodiments, this helps facilitate the elucidation of the likely functions of novel BMCs as well as assist in the bioengineering of these assemblies as nanoreactors.

In some embodiments, the present disclosure allows for sampling precisely controlled stoichiometries between shell proteins (e.g. the hexameric, trimeric, and pentameric species) that may influence shape, size, and architectures of the resultant assemblies. In some embodiments, this influences their behavior as scaffolds and/or affects their optical properties as the size range of BMCs (for example, approximately 40-600 nanometers) allows them to scatter light via the Tyndall effect, for example. In some embodiments, the present disclosure enables robust in vitro assembly and encapsulation of, for example, dyes or other materials with useful optical properties that in some embodiments are of interest in cosmetics.

EXAMPLE 1

Fusion Shell Protein Having Maltose Binding Protein and BMC-H Protein from *H. ochraceum*

Figure 3A:
FIG. 3A is a diagram of the construct used to express in E. coli a BMC fusion protein including Maltose Binding Protein (MBP) and BMC-H protein from H. ochraceum ("Ho-H", "Ho5815", or "Hoch_5815", SEQ ID NO: 1) and configured to be cleavable by TEV protease.
Figure 3B:
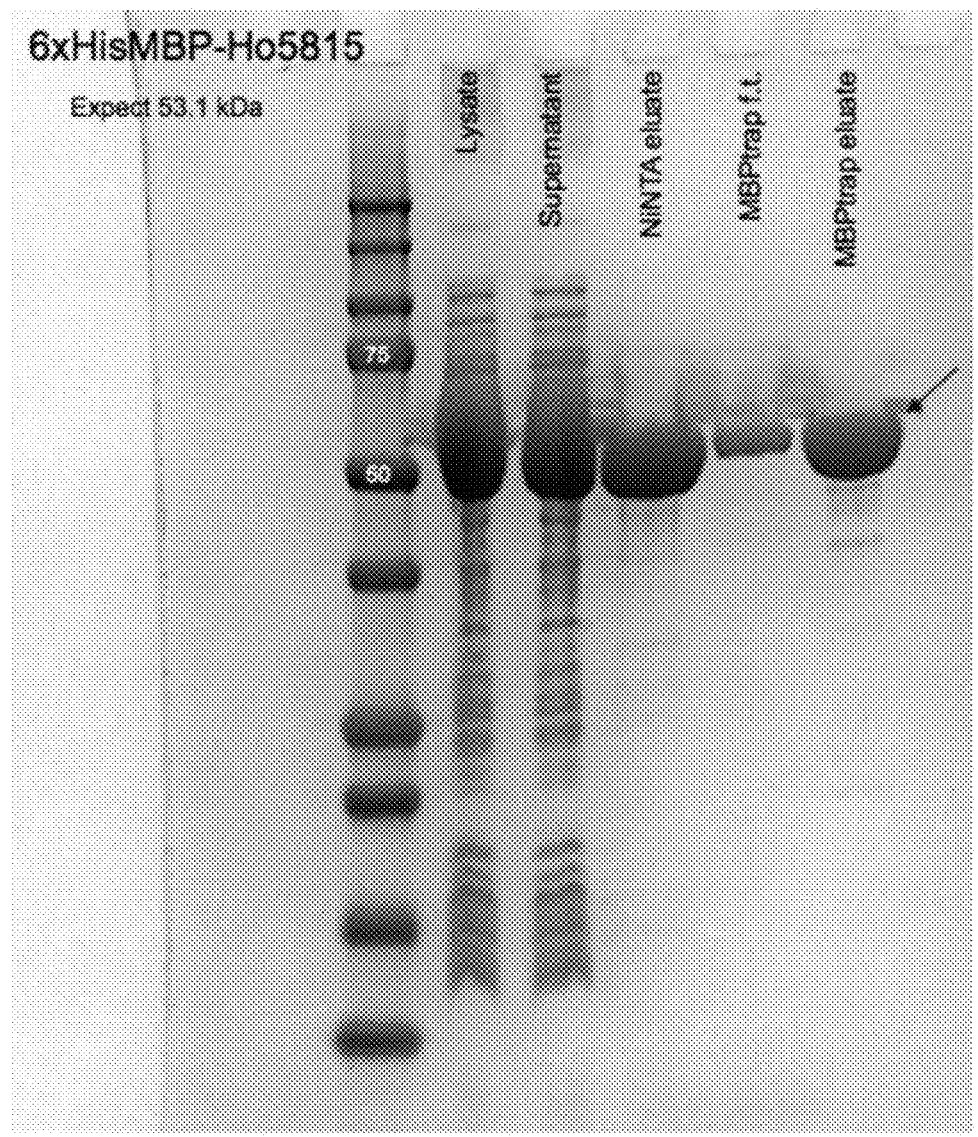
FIG. 3B shows a SDS-PAGE analysis of purification of MBP-Ho5815 fusion protein.
Figure 3C:
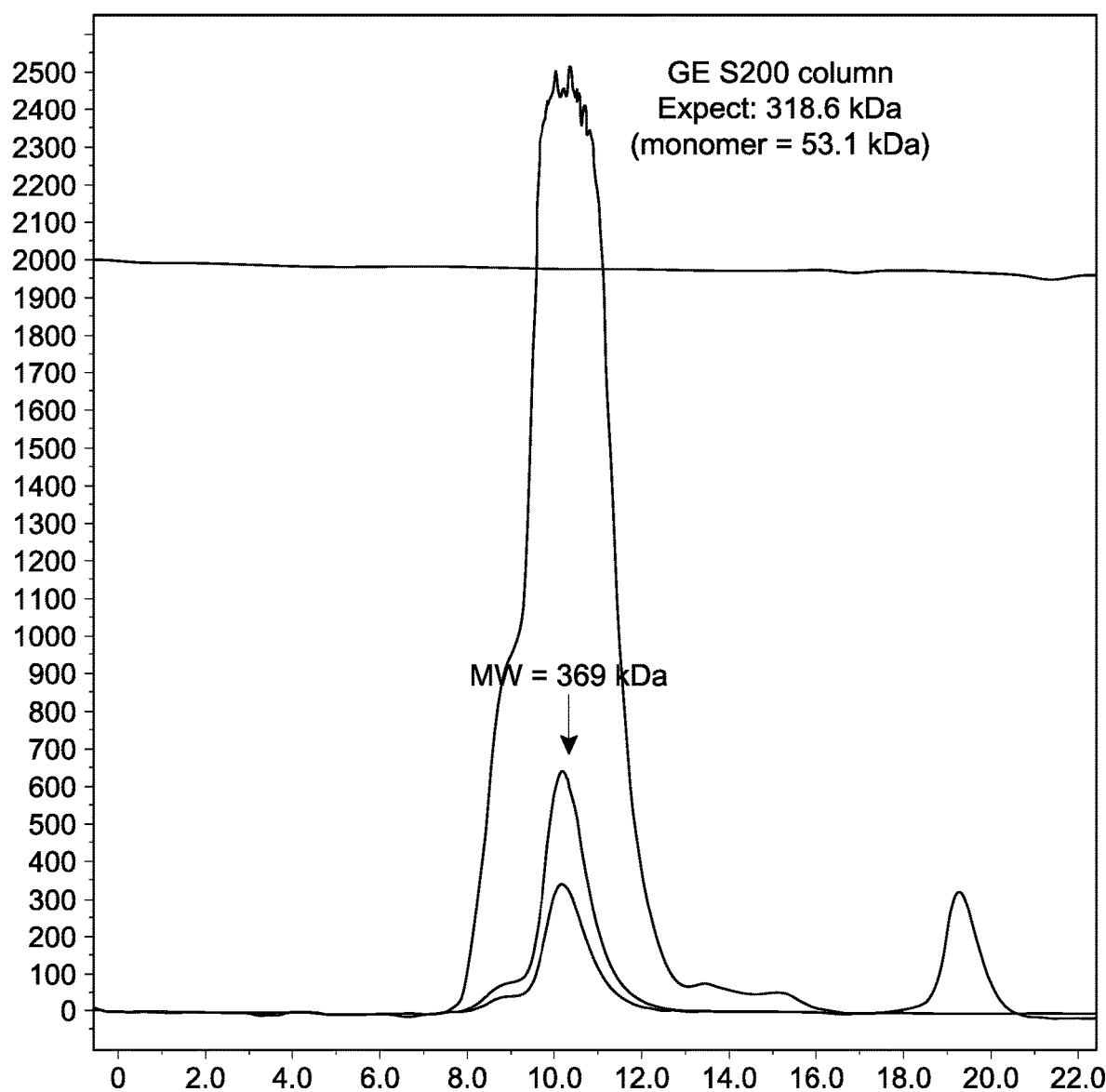
FIG. 3C exhibits an analytical size-exclusion chromatography analysis of MBP-Ho5815 fusion protein.
Figure 3D:
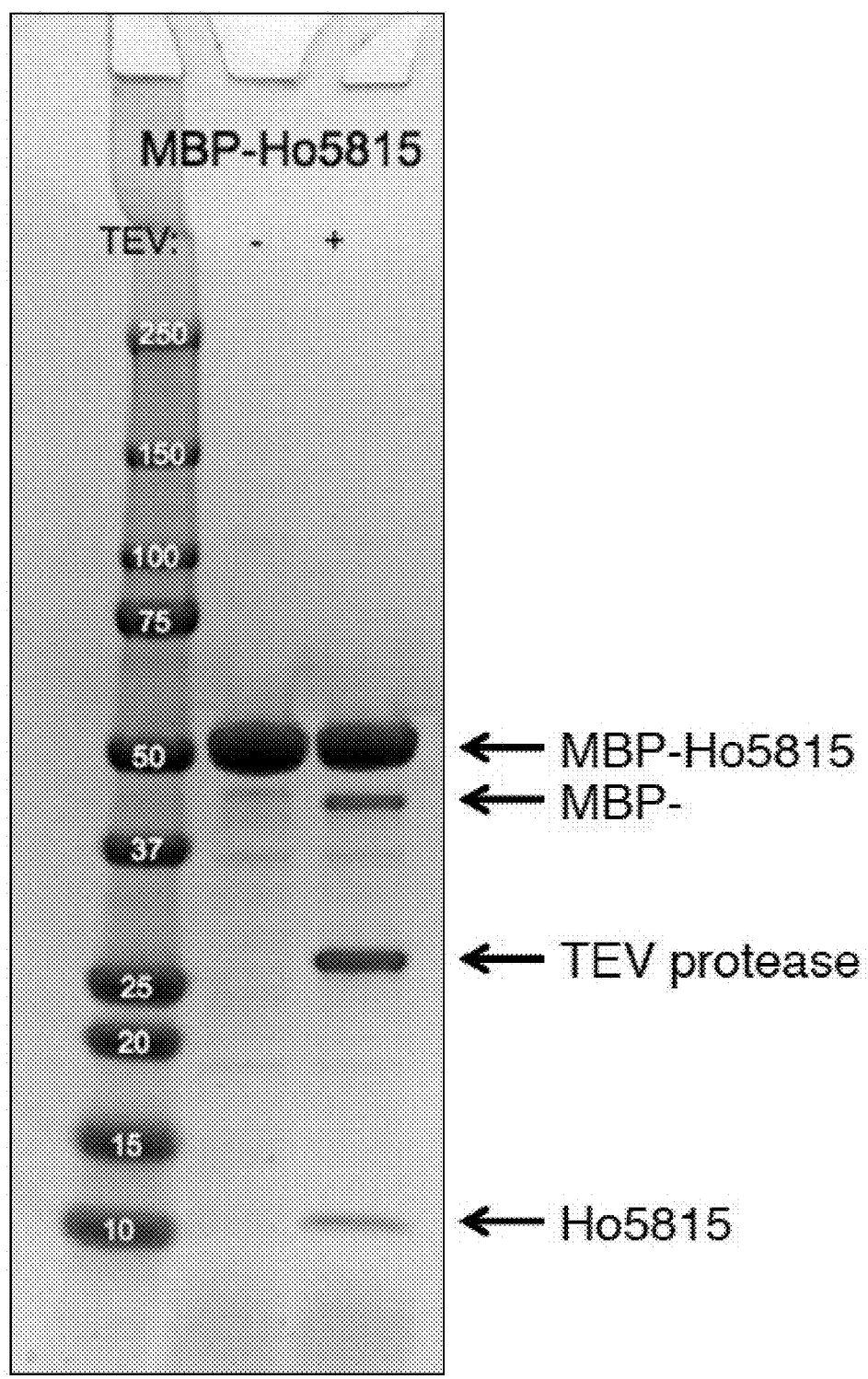
FIG. 3D displays a SDS-PAGE analysis of cleavage of MBP-Ho5815 fusion protein with TEV protease.

The fused protein may comprise a *Haliangium ochraceum* BMC shell protein, a Maltose Binding Protein (MBP), and a hexahistidine tag. FIG. 3A shows a diagram of a construct used to express in *E. coli* (e.g., BL21(DE3)) a BMC fusion protein having MBP as a sterically hindering protein domain and BMC-H protein from *H. ochraceum* ("Ho-H", "Ho5815", or "Hoch_5815", SEQ ID NO: 1) as a fusion shell protein. The MBP-Ho5815 fusion protein is configured to be cleavable by TEV protease. The construct has pTet promoter, RBS, and a hexahistidine tag at the 5' end of the DNA sequence encoding for the BMC fusion protein. Referring to FIG. 3B, SDS-PAGE analysis of purification of MBP-Ho5815 fusion protein indicates robust expression and purification. Referring to FIG. 3C, analytical size-exclusion chromatography indicates that the MBP-Ho5815 fusion protein exists in a hexameric form in solution as expected. Referring to FIG. 3D, SDS-PAGE analysis of MBP-Ho5815 cleavage with TEV protease shows that MBP-Ho5815 fusion protein is cleaved by TEV, but is comparatively recalcitrant to cleavage with TEV, even at relatively high TEV loading (1:10 w/w TEV:fusion protein).

EXAMPLE 2

Fusion Shell Protein Having Short Ubiquitin-Related Modifier and BMC-H Protein from *H. ochraceum*

Figure 4A:
FIG. 4A is a diagram of an example construct used to express in E. coli a BMC fusion protein including Short Ubiquitin-related Modifier (SUMO) and BMC-H protein from H. ochraceum ("Ho-H", "Ho5815", or "Hoch_5815", SEQ ID NO: 1) and configured to be enzymatically cleaved by Ulp protease.
Figure 4B:
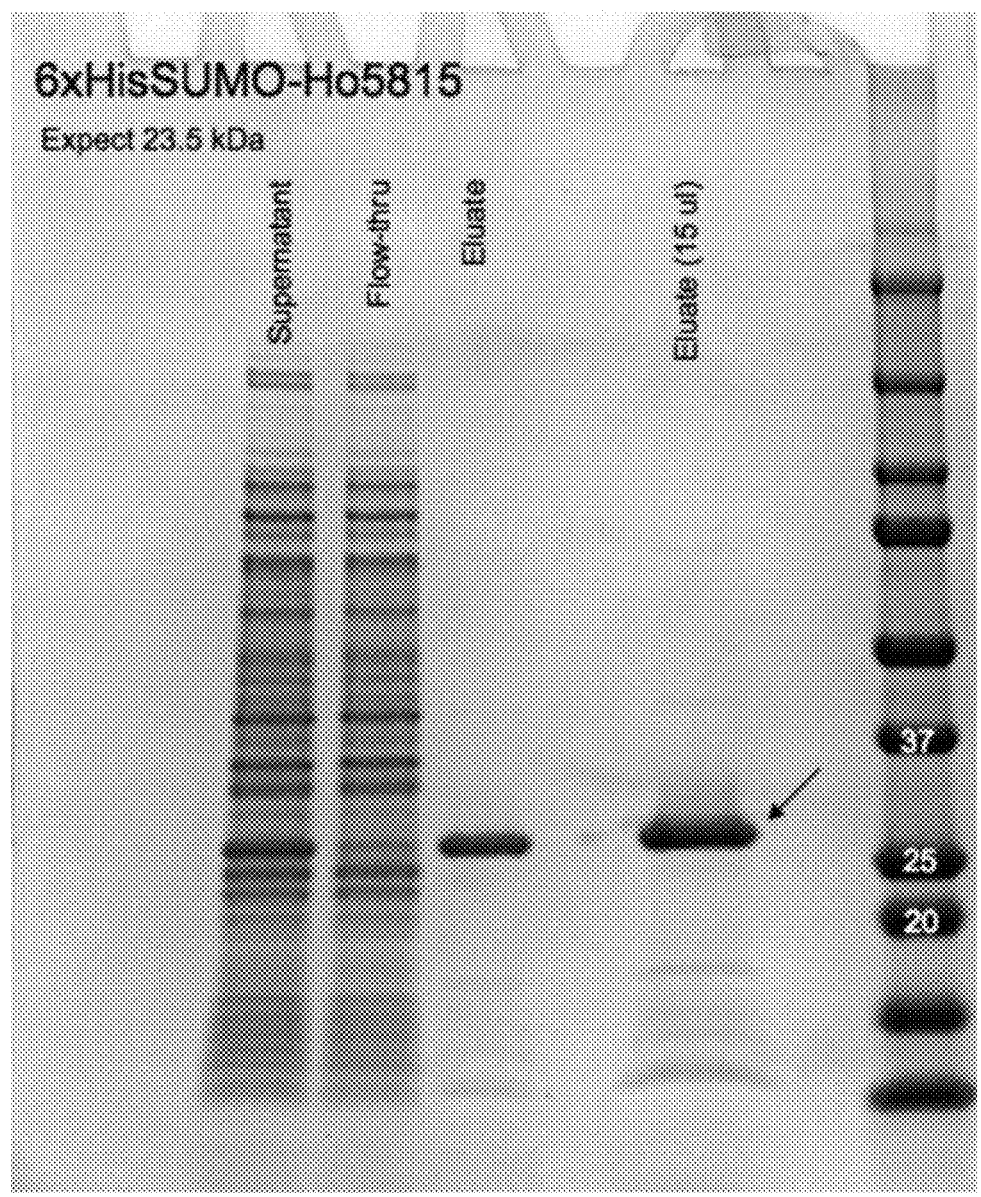
FIG. 4B shows a SDS-PAGE analysis of SUMO-Ho5815 fusion protein.
Figure 4C:
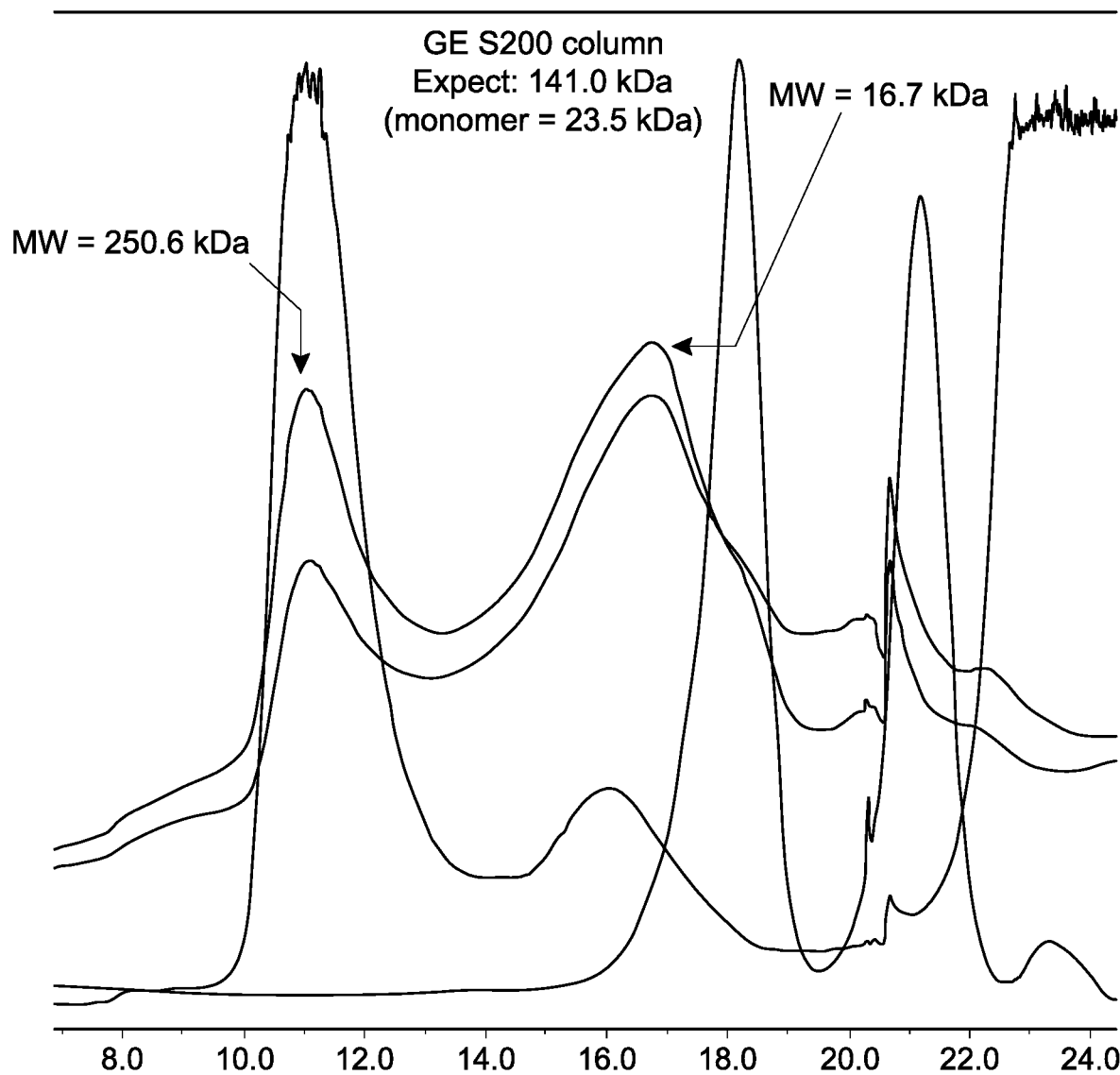
FIG. 4C exhibits an analytical size-exclusion chromatography analysis of SUMO-Ho5815 fusion protein.
Figure 4D:
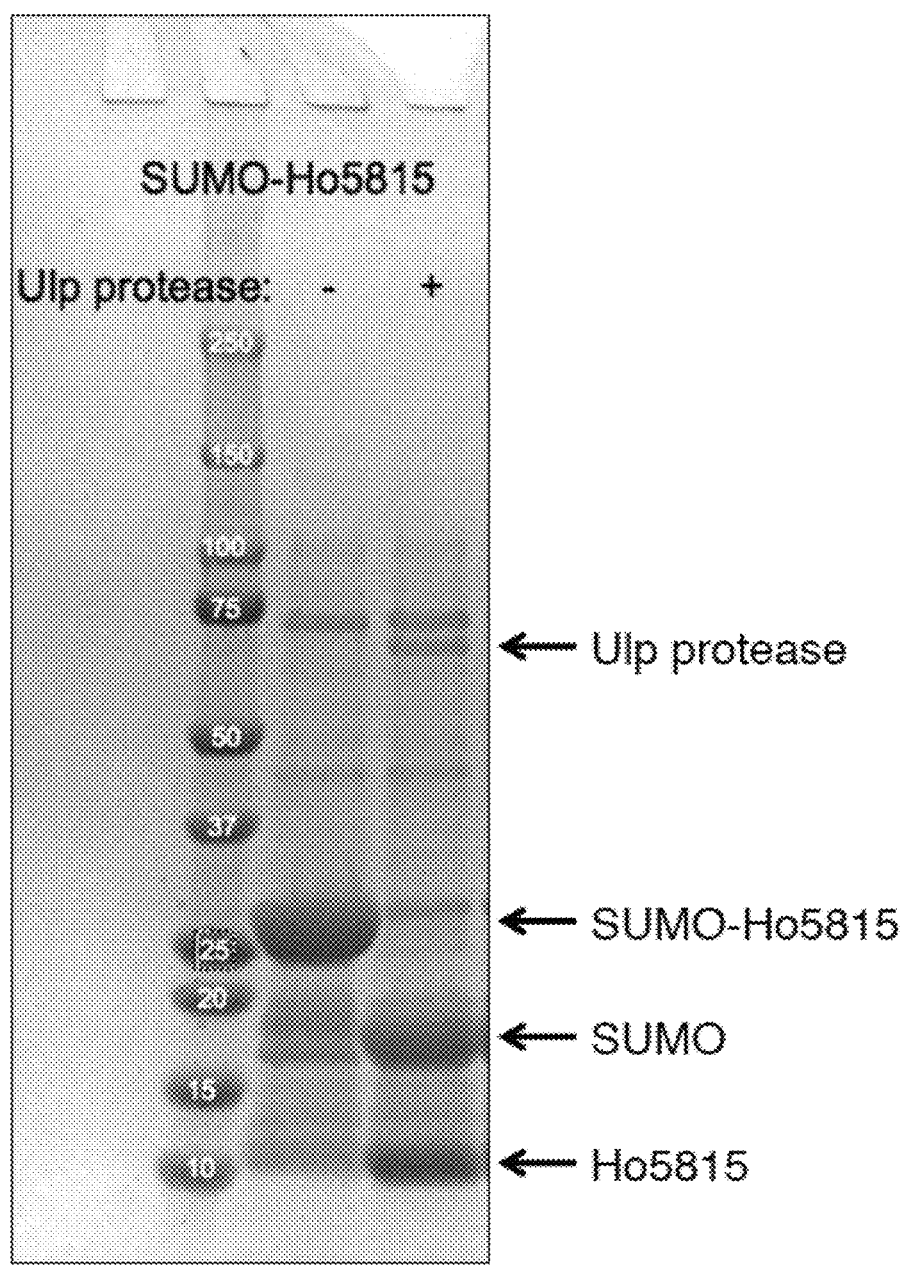
FIG. 4D displays a SDS-PAGE analysis of cleavage of SUMO-Ho5815 fusion protein with Ulp protease.

The fused protein may comprise *Haliangium ochraceum* BMC shell proteins, an N-terminal Short Ubiquitin-related Modifier (SUMO) domain, and a hexahistidine tag. FIG. 4A describes a diagram of the construct used to express in *E. coli* (e.g., BL21(DE3)) a BMC fusion protein having SUMO as a sterically hindering protein domain and BMC-H protein from *H. ochraceum* ("Ho-H", "Ho5815", or "Hoch_5815", SEQ ID NO: 1) as a fusion shell protein. The SUMO-Ho5815 fusion protein is configured to be cleaved by Ulp protease (also called SUMO protease). The construct has pTet promoter, RBS, and a hexahistidine tag at the 5' end of the DNA sequence encoding for the BMC fusion protein. Referring to FIG. 4B, SDS-PAGE analysis of purification of SUMO-Ho5815 fusion protein indicates robust expression and purification. Referring to FIG. 4C, analytical size-exclusion chromatography indicates that unlike the MBP-Ho5815 fusion protein, the SUMO-Ho5815 fusion protein exists in various oligomeric forms in solution. This may be a result of a significantly smaller fusion domain, which allows dynamic assembly/disassembly. Referring to FIG. 4D, SDS-PAGE analysis of SUMO-Ho5815 cleavage with a recombinant fragment of the ULP1 (Ubl-specific protease) from *Saccharomyces cerevisiae* indicates that the Ulp protease efficiently removes the SUMO domain from the SUMO-Ho5815 fusion protein at modest loading (1:25 w/w Ulp:fusion protein). See U.S. Pat. No. 6,872,551 to Lima et al. regarding a fusion protein with SUMO domain in general. The Ulp protease may be purified as a Maltose Binding Protein fusion. See U.S. Pat. No. 5,643,758 to Guan et al. regarding a method to produce and purify a protein by expressing the protein as a MBP fusion protein. Orthologs of the SUMO domain and its cognate protease are widely distributed among eukaryotes. Therefore, some embodiments include orthogonal sets of SUMO/protease pairs.

EXAMPLE 3

Structural Characterization of Pentamers from Noncanonical BMCs Using BMC Fusion Protein In some embodiments, pentamer shell proteins (pfam03319) cap vertices of icosahedral BMCs and are therefore a minor component of the shell (12 vertices*5 pentamer subunits each=60 subunits total per BMC). Despite a seemingly minor structural role in shell formation, the observation that many BMC operons harbor numerous pentamer paralogs (as many as seven (Sutter *Photosynth. Res.* 2013)), indicates the current understanding of pentamer function may be incomplete. To date, multiple pentamers from the same BMC operon, where present, have not been solved.

The recently characterized BMC operon from *Planctomyces limnophilus* contains three pentamers (e.g., PvmH, PvmK, and PvmM), and knockout studies have suggested an essential role for all three of them (Erbilgin *Appl. Environ. Microbiol.* 2014). The present disclosure of BMC fusion protein may be used to structurally characterize all pentamers from this BMC operon to better understand pentamer function as well as diversify the phylogenetic complement of pentamer structures.

Figure 5A:
FIG. 5A is a diagram of an example constructs used to express in E. coli a BMC fusion protein including SUMO and one of pvmH, pvmK, and pvmM. These SUMO-pvmH/pvmK/pvmM fusion proteins are configured to be cleaved by Ulp protease.
Figure 5B:
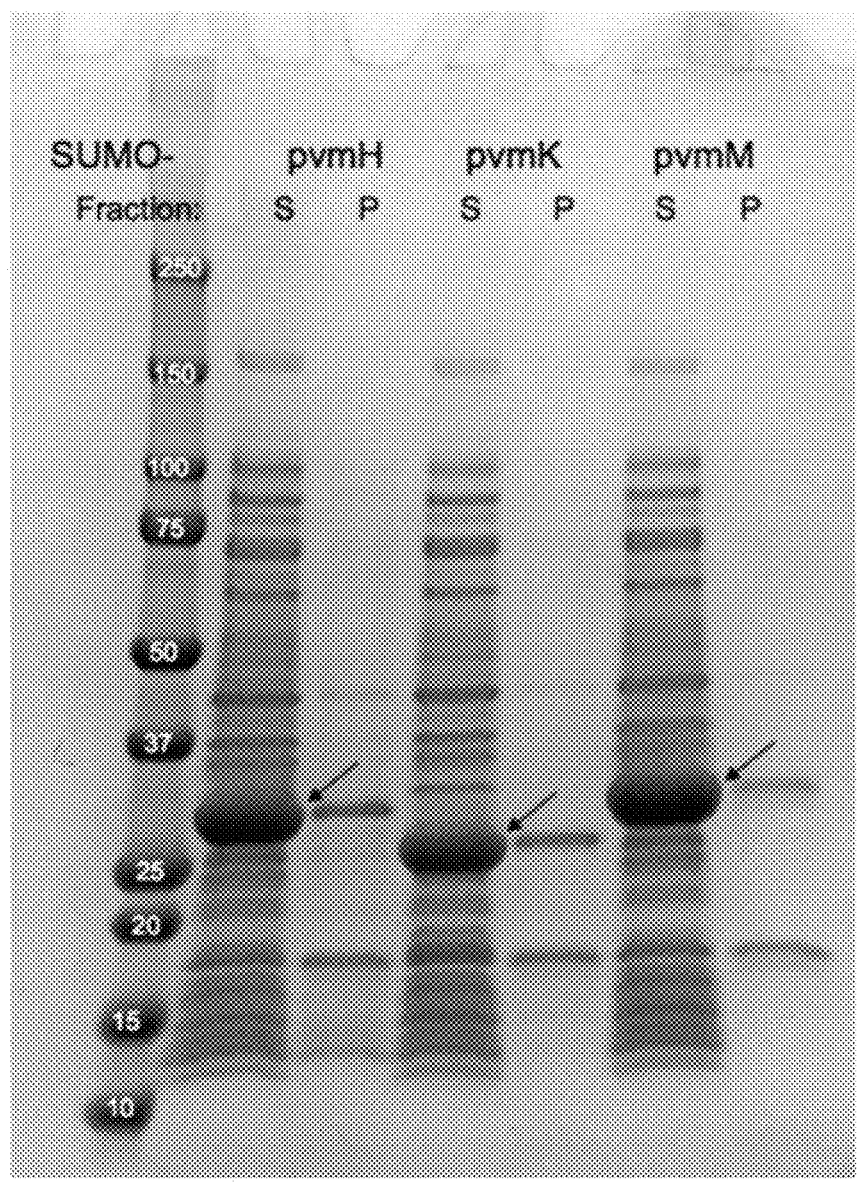
FIG. 5B shows a SDS-PAGE analysis of SUMO-pvmH/pvmK/pvmM fusion proteins.

The fused protein may comprise *Planctomyces limnophilus* BMC shell proteins, an N-terminal SUMO domain, and a hexahistidine tag. FIG. 5A describes a diagram of the construct used to express a BMC fusion protein having SUMO as a sterically hindering protein domain and one of PvmH, PvmK, and PvmM as a fusion shell protein. The SUMO-PvmH/PvmK/PvmM fusion protein is configured to be cleaved by Ulp protease (also called SUMO protease). The construct has pTet promoter, RBS, and a hexahistidine tag at the 5' end of the DNA sequence encoding for the BMC fusion protein. Referring to FIG. 5B, SDS-PAGE analysis of purification of SUMO-PvmH/PvmK/PvmM fusion protein indicates robust, soluble expression as shown by arrows in FIG. 5B. SUMO-PvmH/PvmK/PvmM fusion protein is purified via immobilized metal affinity chromatography (IMAC) and/or anion exchange chromatography (AIEX).

Figure 5C:
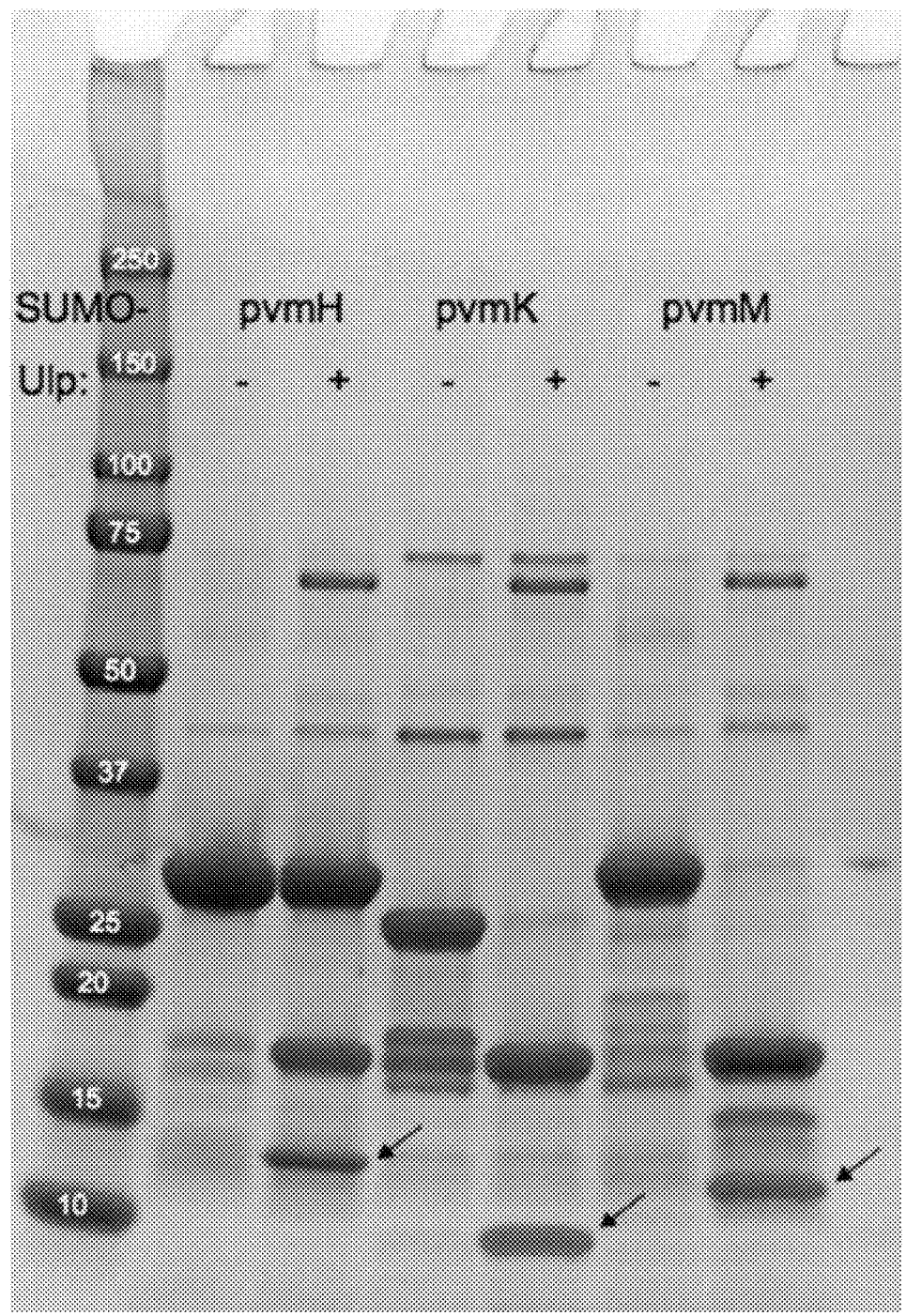
FIG. 5C shows a SDS-PAGE analysis of SUMO-pvmH/pvmK/pvmM fusion proteins before and after being cleaved by Ulp protease.

Referring to FIG. 5C, SDS-PAGE analysis of SUMO-PvmH/PvmK/PvmM fusion protein cleaved by Ulp protease indicates that purified SUMO-PvmH/PvmK/PvmM fusions are readily cleaved by Ulp protease into their native form. Arrows indicate liberated Pvm proteins.

The cleaved PvmH/PvmK/PvmM shell proteins may be used for structural analysis. In some embodiments, when used with other types of shell proteins, the cleaved PvmH/PvmK/PvmM shell proteins form bacterial microcompartments in vitro. In some embodiments, in vitro production of BMCs enables those of skill in the art to finely probe which components are necessary and/or sufficient for BMC shell assembly; follow assembly kinetics with, for example, isothermal titration calorimetry; and encapsulate abiotic probes to assess permeability.

EXAMPLE 4

Assembly Principles and Structure of a 6.5 MDa Bacterial Microcompartment Shell

One embodiment is the crystal structure of an intact shell from *Haliangium ochraceum*, revealing basic principles of bacterial microcompartment shell construction. Given the conservation among shell proteins of all bacterial microcompartments, these principles apply to functionally diverse organelles and can inform the design and engineering of shells with new functionalities.

Figure 6A:
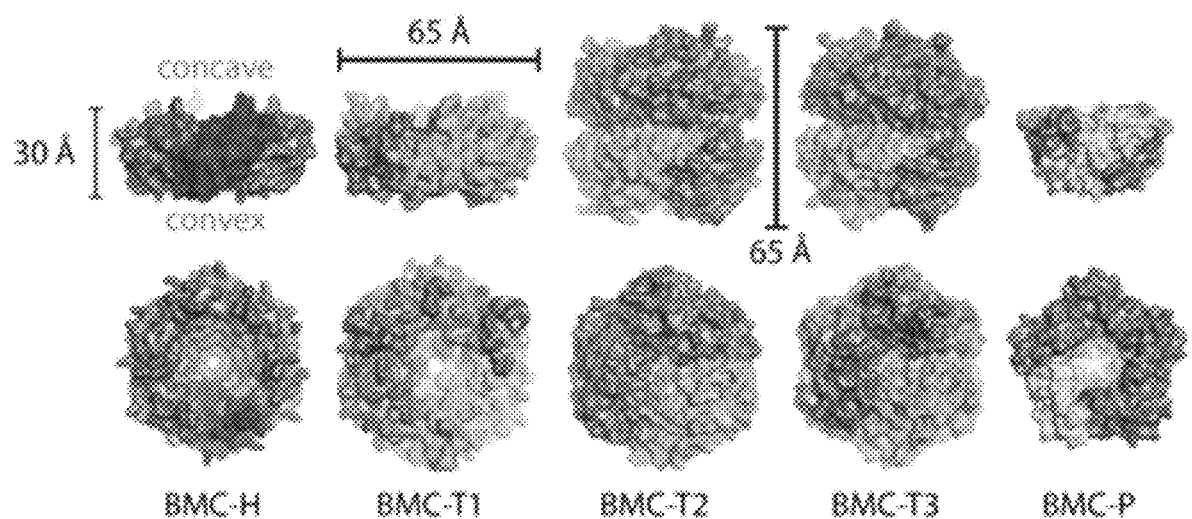
FIGS. 6A-6E include an overview of the components and the overall structure of an example BMC shell.

Bacterial microcompartments (BMCs) are large, proteinaceous shells encapsulating enzymes. The first discovered, carboxysomes, enhance carbon fixation (1). The BMC shell is a singular example of a primitive, conserved yet functionally diverse bioarchitecture. Recent bioinformatic surveys of bacterial genomes have revealed the presence of genes encoding shell proteins in 23 different bacterial phyla, encapsulating segments of functionally diverse metabolic pathways (2). In some embodiments, major components of BMC shells include cyclic hexamers with a pronounced concave-versus-convex sidedness (3). These proteins, referred to as BMC-H, typically contain a single BMC (pfam00936) domain (FIG. 6A). A derivative of BMC-H proteins, BMC-T, includes a fusion of two BMC domains forming trimers or pseudohexamers (FIG. 6A). Some members of the BMC-T family form tightly appressed, stacked dimers of trimers, containing a central cavity (4, 5) (FIG. 6A, BMC-T2 and BMC-T3). BMC-P proteins belong to pfam03319; they tend to be structurally unrelated to the BMC/pfam00936 domain and form pentamers shaped like a truncated pyramid (6) (FIG. 6A). Despite detailed structural knowledge of the individual shell components, the architectural principles governing shell self-assembly have remained unknown.

Figure 6B:
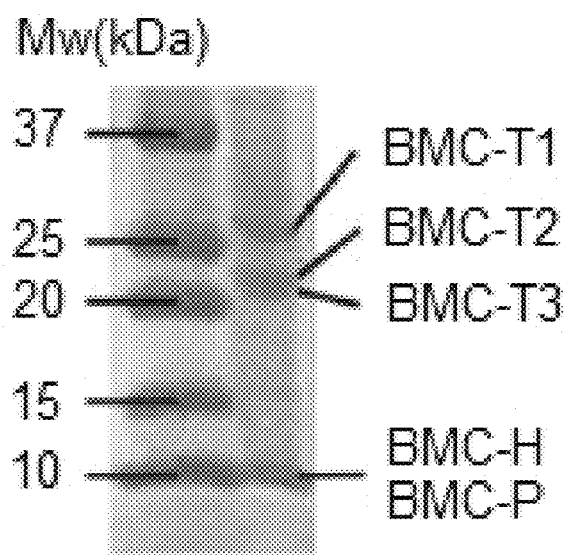
Figure 6C:
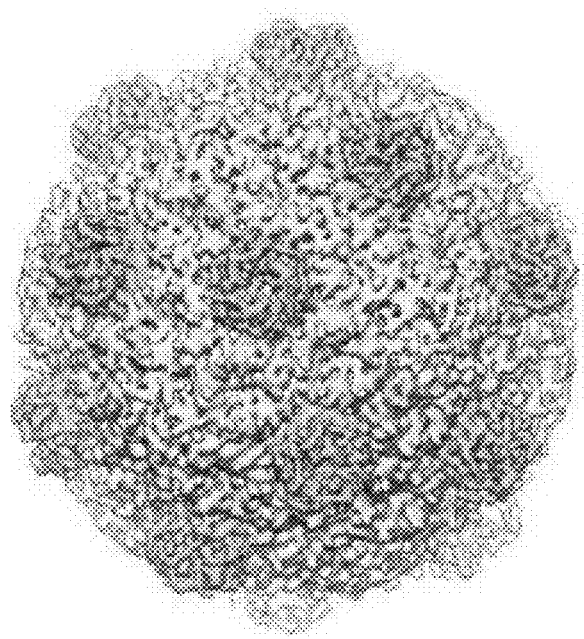

Using a recombinant system containing all of the facet proteins (one BMC-H and three BMC-T paralogs) and one of the three BMC-P proteins of the myxobacterium *Haliangium ochraceum* BMC (FIGS. 6A and 6B) (7), homogeneous 40 nm BMC shells with a molecular mass of 6.5 MDa were produced. A complete closed particle was crystallized, and its structure was determined to a resolution of 3.5 Å (CC1/2 of 26%, Table 1). A cryo-EM map at a resolution of 8.7 Å (FIG. 6C) was used to place individual structures and phase the crystallographic data. To facilitate the interpretation of the data, the crystal structures of the pseudohexameric BMC-T2 and BMC-T3 proteins were also determined (Table 1).

Figure 6D:
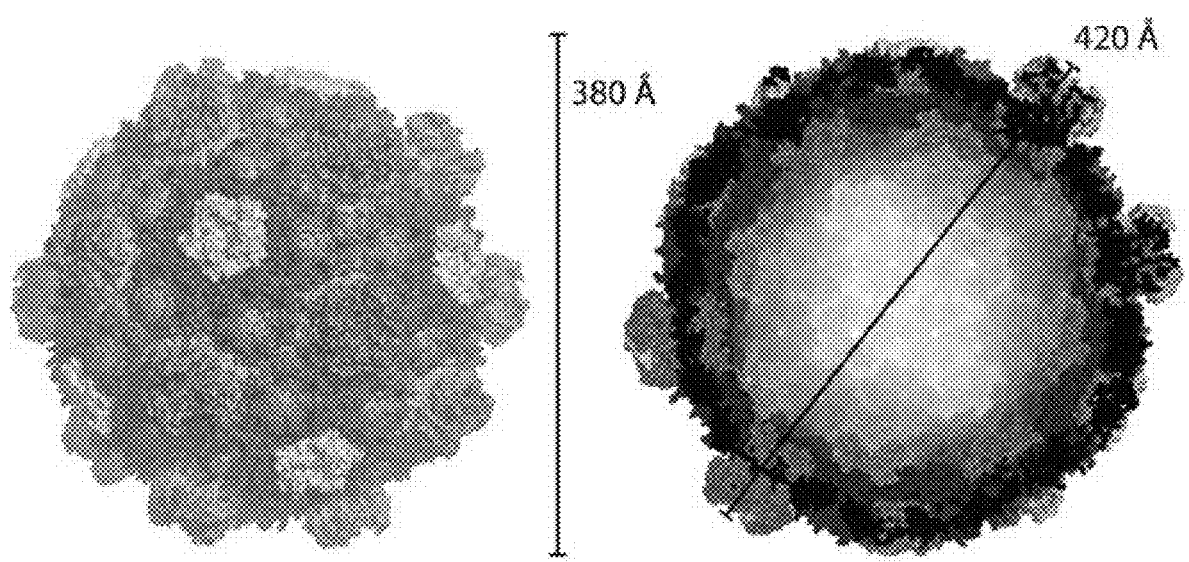

The co-expressed shell proteins self-assembled into a pseudo T=9 icosahedral shell (designated pseudo because not all subunits were identical), with a diameter of about 400 Å (FIG. 6D). The shell included 12 BMC-P pentamers at the vertices; the facets are formed by 60 BMC-H hexamers enclosing 20 BMC-T pseudohexamers of the three different paralogous types (FIG. 6A). This stoichiometry was in agreement with what was observed for purified shells on SDS-PAGE (FIG. 6B) and previous analyses (7).

Figure 6E:
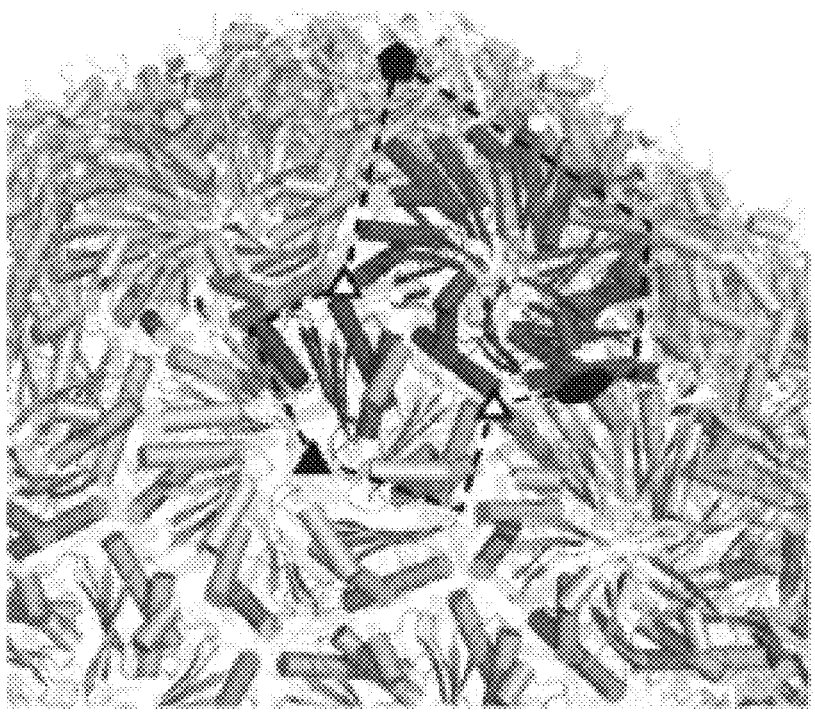
Figure 10A:
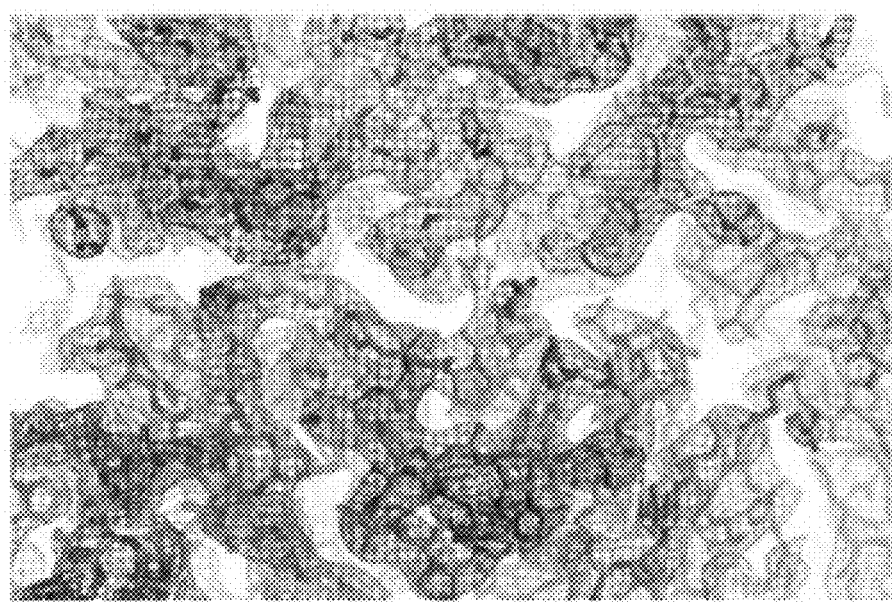
FIGS. 10A and 10B depict electron densities.

The icosahedral asymmetric unit included one BMC-P chain, six BMC-H chains and one BMC-T chain (two chains for the double stacking type) (FIG. 6E). Model building was facilitated by the available high resolution structures of the hexamer (8), the pseudohexamers ((9) and the work described herein) and the 30-fold non-crystallographic symmetry, which collectively resulted in a good model fit and geometry (for sample electron density see FIG. 10A). Because three different proteins can occupy the BMC-T positions, this density is representative of a mixture. Due to the structural similarity between all three BMC-T, we can confidently place a protein model (we chose BMC-T2 based on overall fit). The resulting shell facets included a single layer with a thickness of 20-30 Å with one of the trimers of BMC-T2 and BMC-T3 protruding to the outside (FIG. 6D). The shell structure answers the fundamental questions of the shell being single or double layered, how stacked pseudohexamers are accommodated, as well as the orientations of the individual subunits. For the pentamers, the broader side (the base of the pyramid), faces outward. In the facets, the concave sides of BMC-H and BMC-T1 (pseudo) hexamers (containing the N- and C-termini) face outwards. Likewise, the lower trimers of the double stacking BMC-T2 and BMC-T3 pseudohexamers are in the same (concave out) orientation but due to a circular permutation, their N- and C-termini face the inside. Given that it is the interface with cytosolic metabolism, knowledge of the location of the polypeptide termini and the sidedness of the shell proteins is helpful for understanding and manipulating the function of BMCs in their native context, as well as for engineering synthetic microcompartments.

Figure 7A:
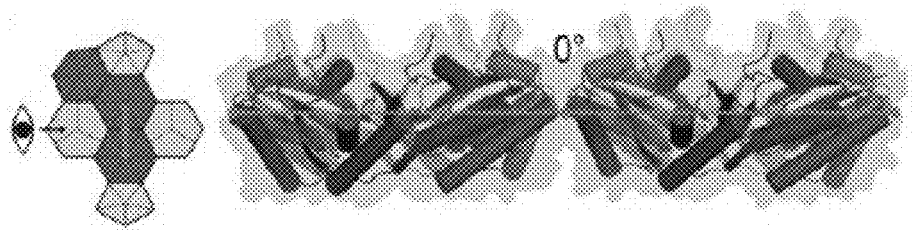
FIGS. 7A-7D include an overview of the four distinct interfaces between the pentamer, hexamers and the pseudohexamers of an example structure. Structures are shown in cartoon view (surface view as light grey background) with a pictogram showing their location on the shell.
Figure 7B:
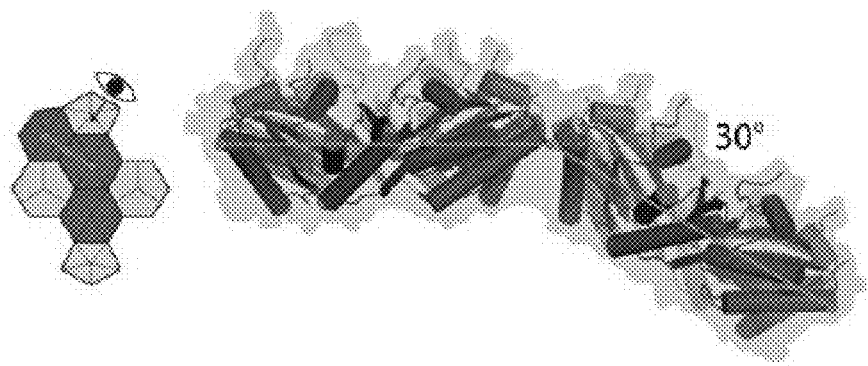
Figure 7C:
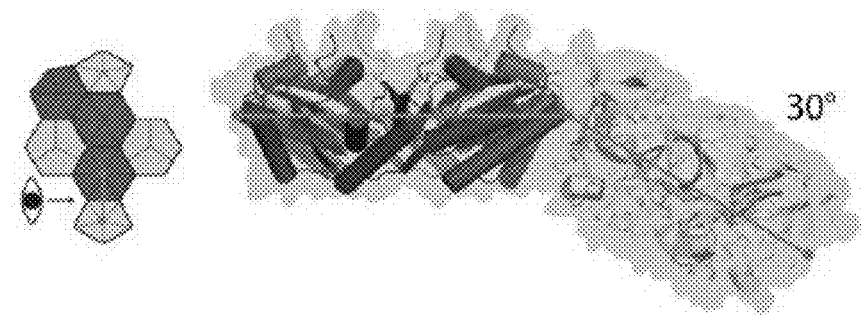
Figure 7D:
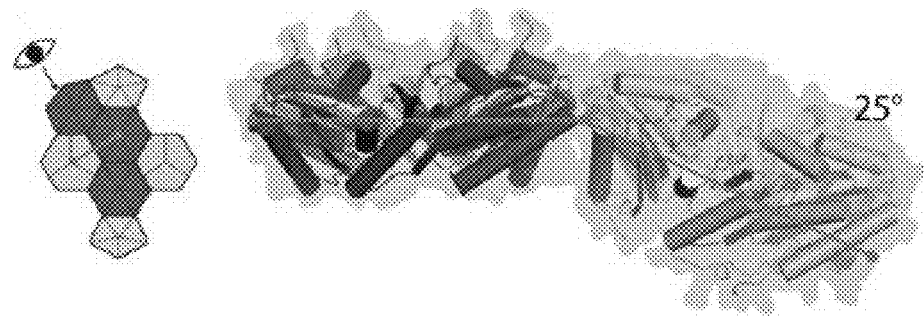
Figure 11A:
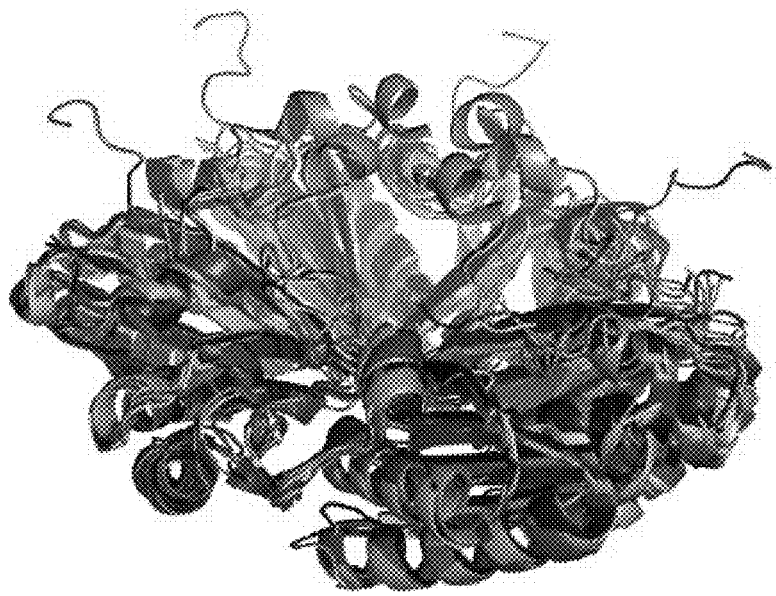
FIGS. 11A-11D are structural alignment images.
Figure 11B:
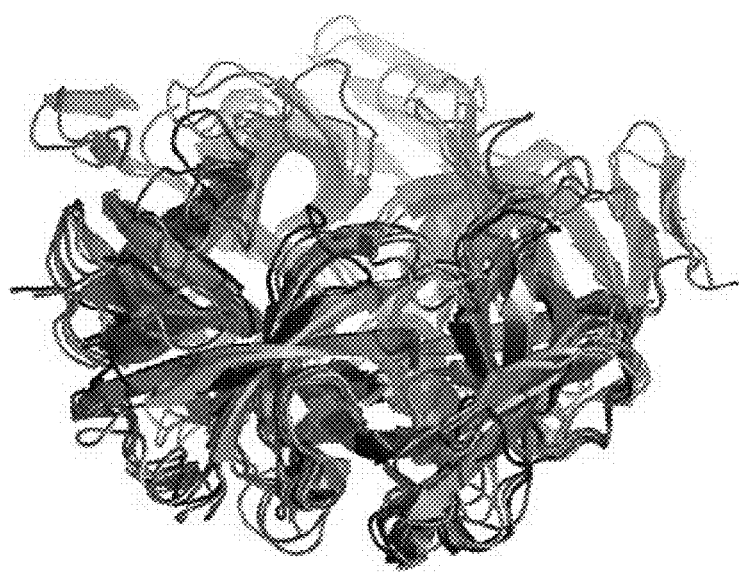
Figure 11C:
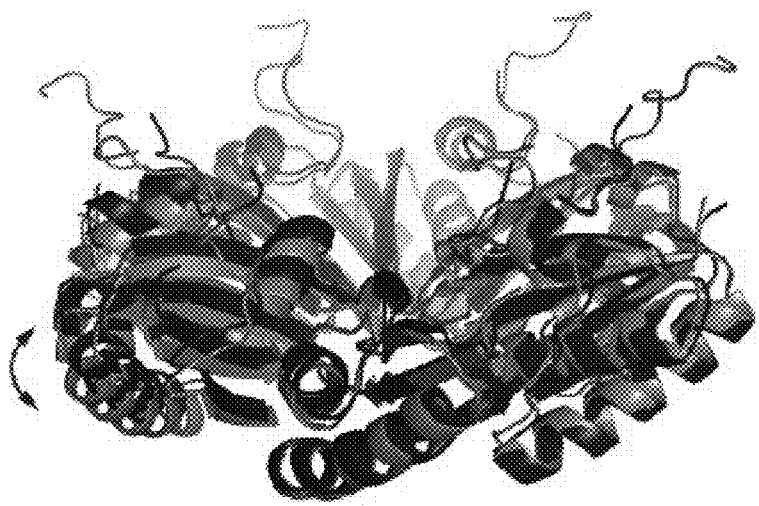

There were four distinct interfaces in the intact shell (FIGS. 7A-7D): two different hexamer-hexamer interactions (FIGS. 7A and 7B), the hexamer-pentamer (FIG. 7C) and the hexamer-pseudohexamer interaction (FIG. 7D). The hexamers connecting pentamers between two vertices of the intact shell (FIG. 7A) were in a side-by-side, planar orientation, while the hexamers surrounding the pentamers (FIG. 7B) were tilted by 30°. Considering the high structural conservation among hexamer and pentamer proteins (FIGS. 11A and 11B) those orientations are likely universal among BMCs. The hexamer in the shell was slightly compressed on the edge adjoining the pentamer, this is apparent by superimposing it on the structure of the hexamer determined in isolation (8) (FIG. 11C and FIG. 6D, where the edge facing the pentamer bulges outwards (darker color)). This distortion illustrates at least one benefit for ensuring accuracy of the approach described herein compared to computationally modelling of large, multi-protein complexes based on individual crystal structures.

Figure 11D:
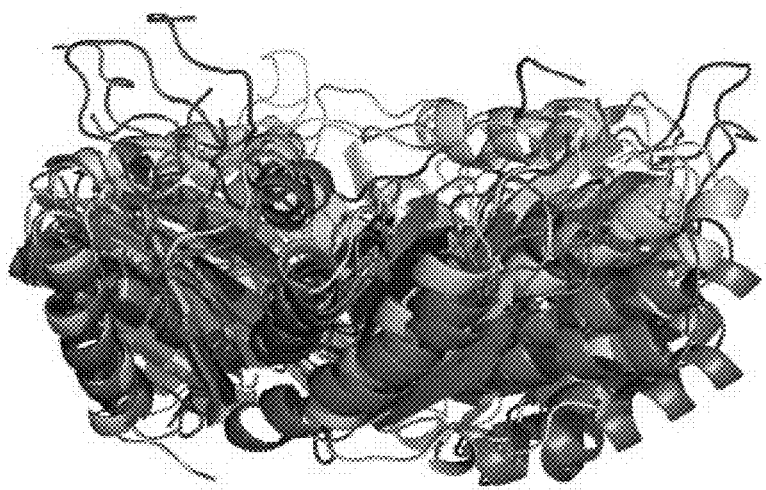

Structurally, the pseudohexameric BMC-T proteins were slightly more compact than the BMC-H hexamers, with the BMC domains folded relatively inward on the concave side (FIG. 11D). Placing hexamers in these positions would require significant deformation to enable them to be accommodated. BMC-T pseudohexamers contain two copies of the BMC domain, and in our structure one domain interacts with the coplanar hexamer-hexamer corner and the other with the corner where the two hexamers join at a 30° angle (FIG. 6E). Because the two domains are decoupled on a genetic level, their primary structures have evolved separately so that each domain can fulfil distinct interface roles. Indeed, all characterized BMCs contain at least one BMC-T type protein; in almost all genomes encoding BMCs, including those of unknown function, a gene for a BMC-T protein is present (2), underscoring, according to some embodiments, their structural importance.

Figure 8A:
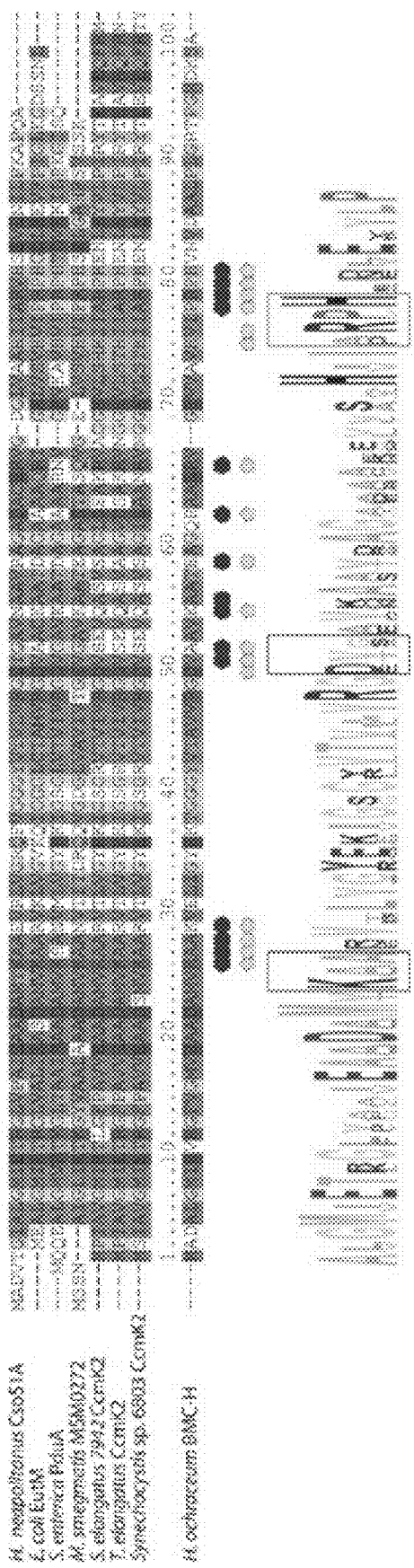
FIGS. 8A and 8B are depictions of sequence alignments of representative BMC-H (FIG. 8A) and BMC-P (FIG. 8B) from representative species. The representative BMC-H and BMC-P were selected to correspond to characterized, functionally diverse BMCs and with available crystal structures for the isolated subunits. The numbering is adjusted to correspond to the H. ochraceum sequences. Interfacing residues are marked by light grey pentagons for pentamer interactions and dark grey hexagons for hexamer interactions. Shading of conserved residues is according to physical properties (from darkest to lightest: negatively charged, positively charged, hydrophobic, polar, proline/glycine). Sequence conservation logos of the combined representative types are shown below the sequence alignments, with each amino acid color-shaded individually. Letter height corresponds with relative frequency at each position. Additional detail for each type shown in FIG. 12 and FIG. 13.
Figure 8B:
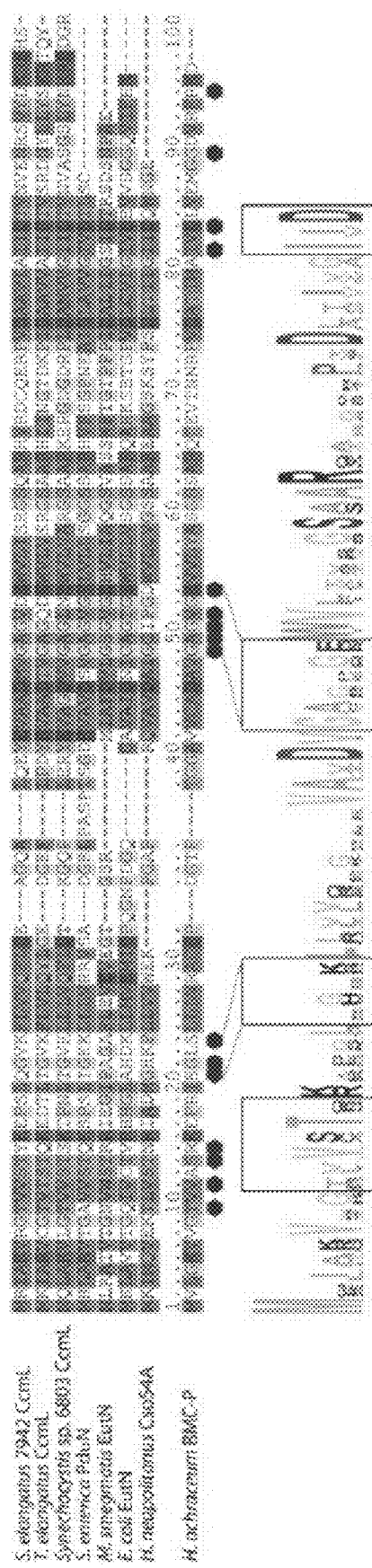
Figure 9A:
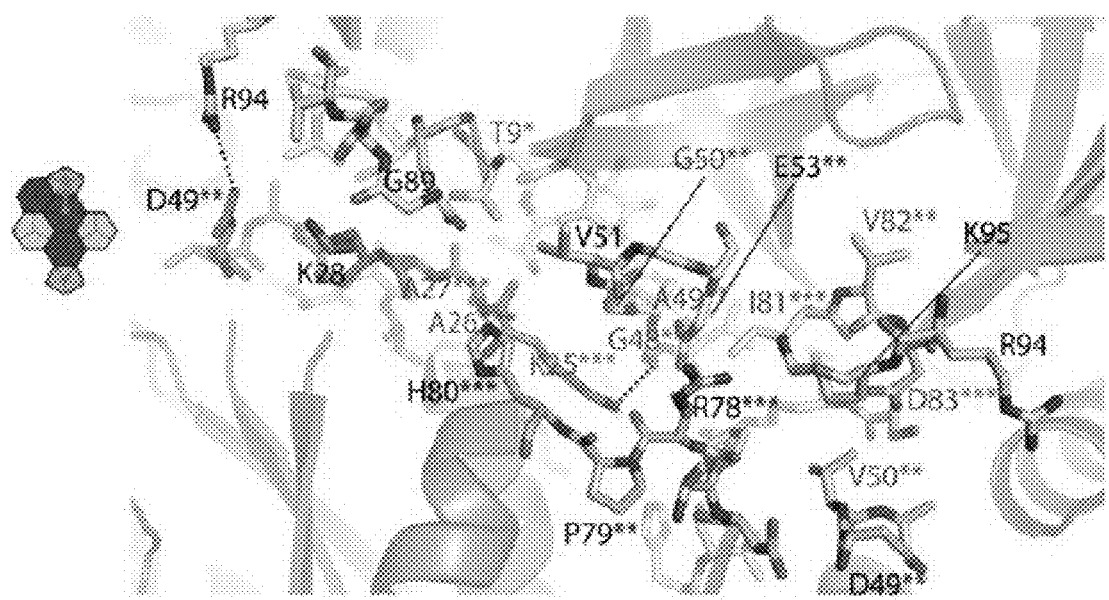
FIGS. 9A-9C are images showing a detailed view of an example BMC-H-BMC-P and two different BMC-H interfaces viewed from the outside.
Figure 12:
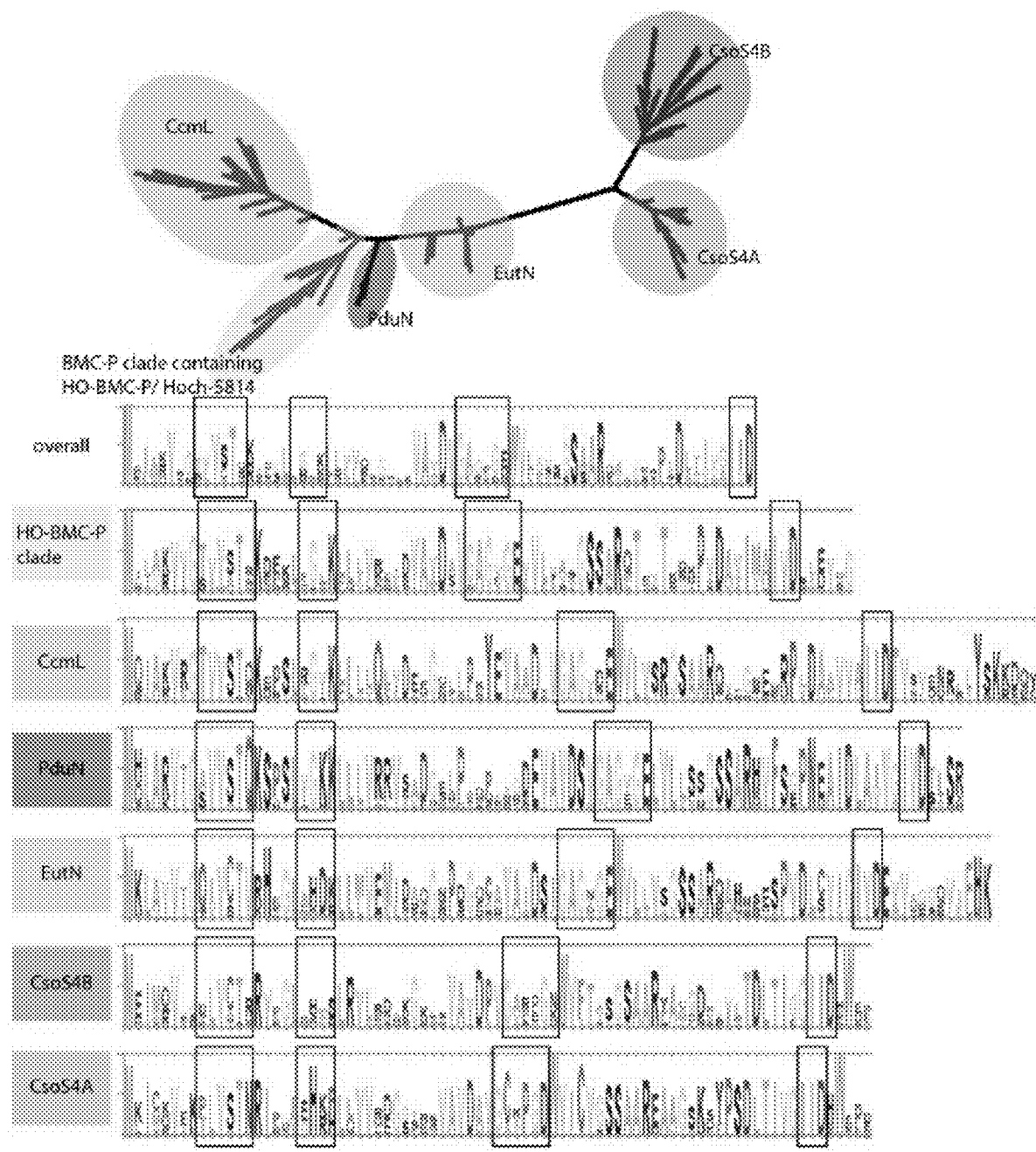
FIG. 12 depicts BMC-P sequence analysis information. A phylogenetic tree of BMC-P proteins (pfam03319) and corresponding sequence logos for overall alignment and the different types are shown. Main regions interacting with the BMC-H are highlighted with boxes.
Figure 13:
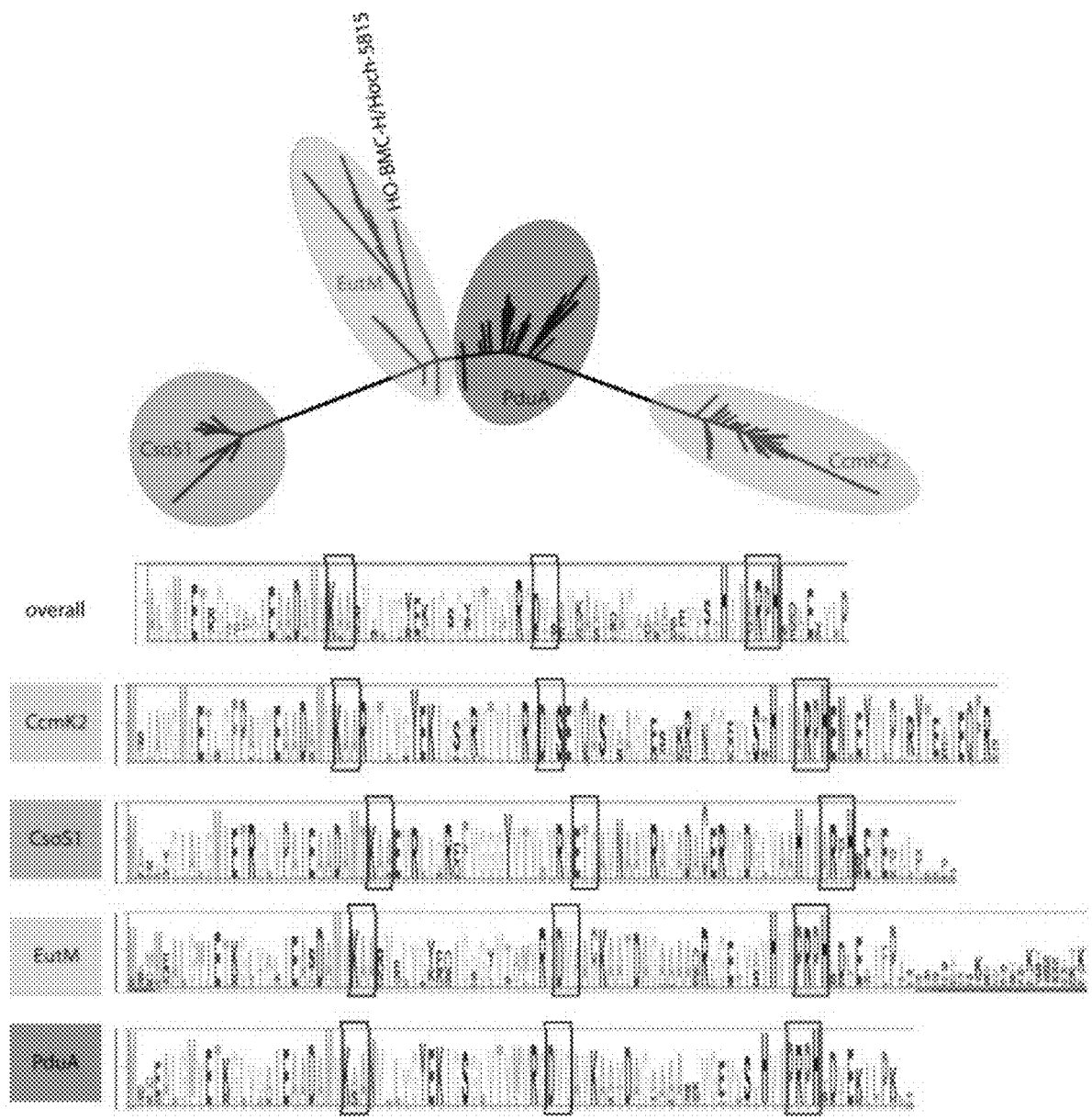
FIG. 13 depicts BMC-H sequence analysis information. A phylogenetic tree of BMC-H proteins from experimentally characterized BMCs and corresponding sequence logos for overall alignment and the different types are shown. Main regions interacting with the BMC-P and other BMC-H are highlighted with boxes including boxes around the KAA motif (boxes on right side) and PRPH (boxes on left side). The *H. ochraceum* BMC-H protein is a member the clade of sequences containing EutM.
Figures 14A, 14B:
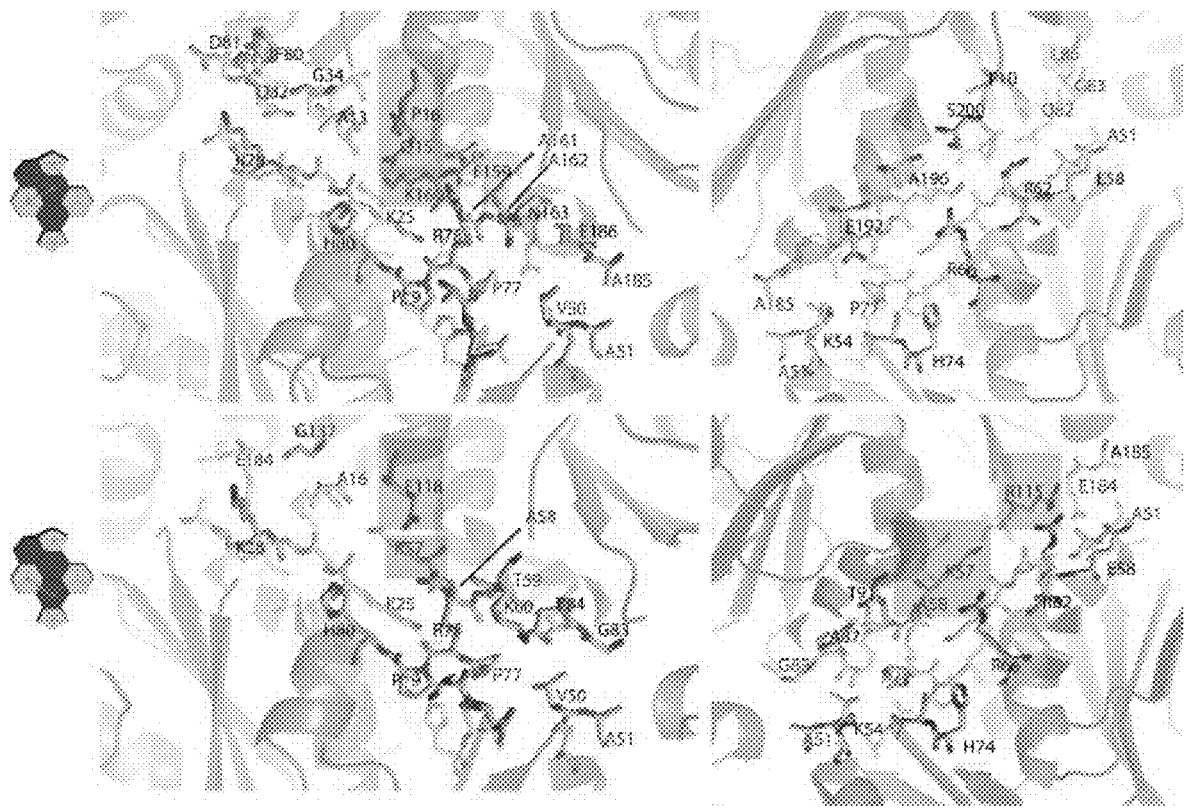
FIGS. 14A and 14B show a detailed view of BMC-T: BMC-H interactions.
Figure 15A:
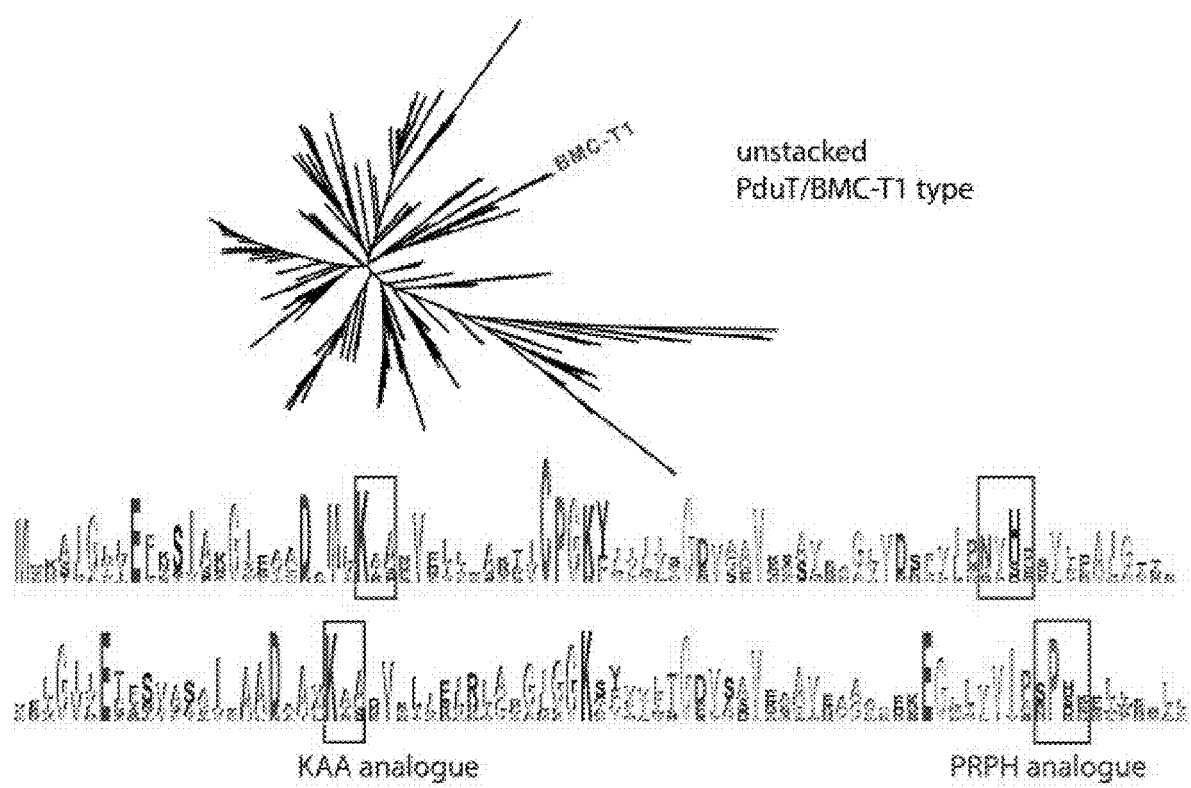
FIGS. 15A and 15B include phylogenetic trees and conservation logos of BMC-T type proteins.
Figure 15B:
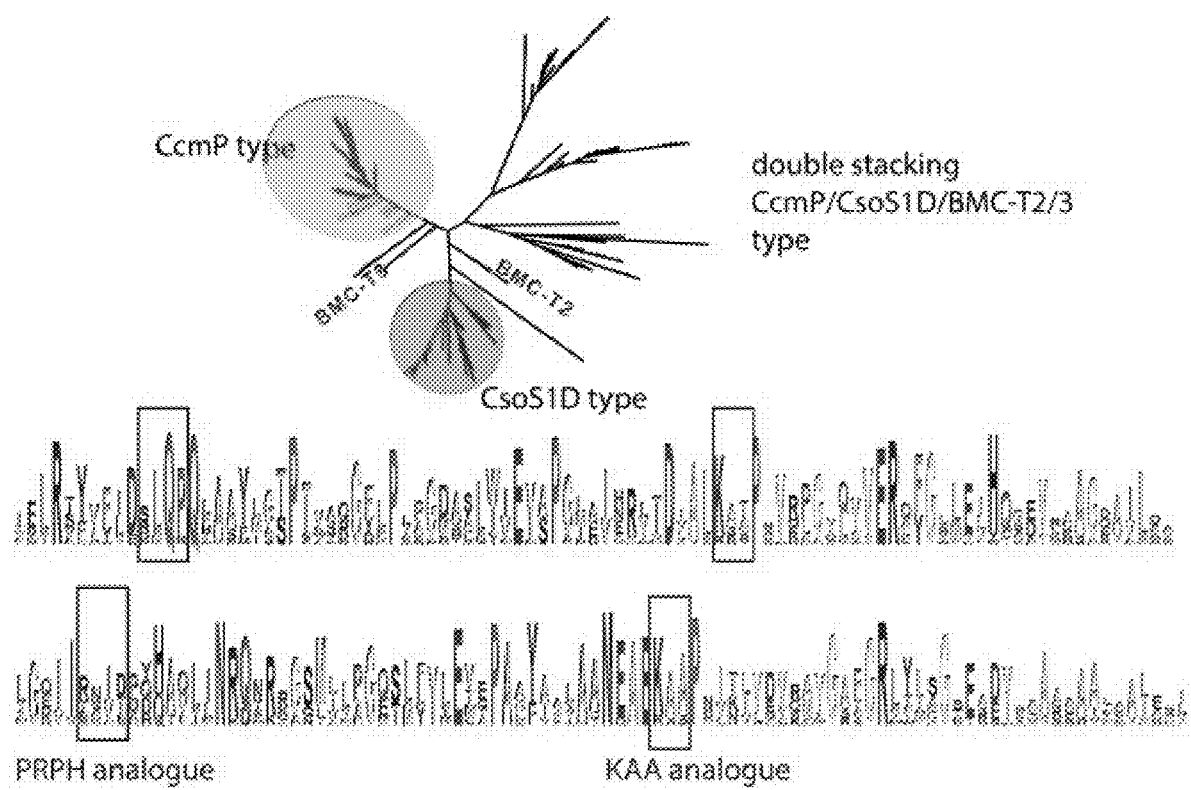

Specific residues involved in the interactions among hexamers and pentamers were located in distinct conserved patches distributed across the primary structure (FIG. 8A). Highly conserved pentamer residues involved in intersubunit interactions (FIGS. 8A, 9A and 12) include S13, the GAGxGE motif (48-53) and the I(V/I)D motif (81-83). On the hexamer, the KAA motif at position 25-27 as well as the PRPH motif at position 77-80 play roles in forming the interface with the pentamer (FIGS. 8B, 9A and 13). Hexamer residues 49-51 (D/E-T/V-A/G/S) are located at the corner between the pentamer and two hexamers, the conservation of a small amino acid at position 51 is beneficial; large residues there would likely preclude shell formation. Overall, shape complementarity governs the hexamer-pentamer interactions there are few salt bridges and hydrogen bonds.

Figure 9B:
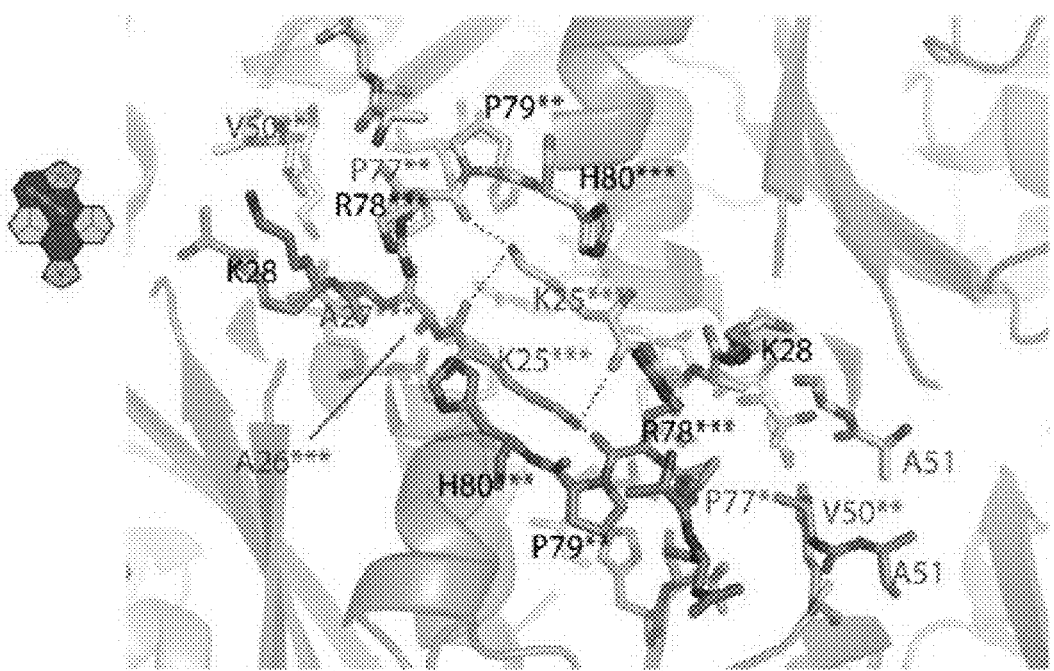
Figure 9C:
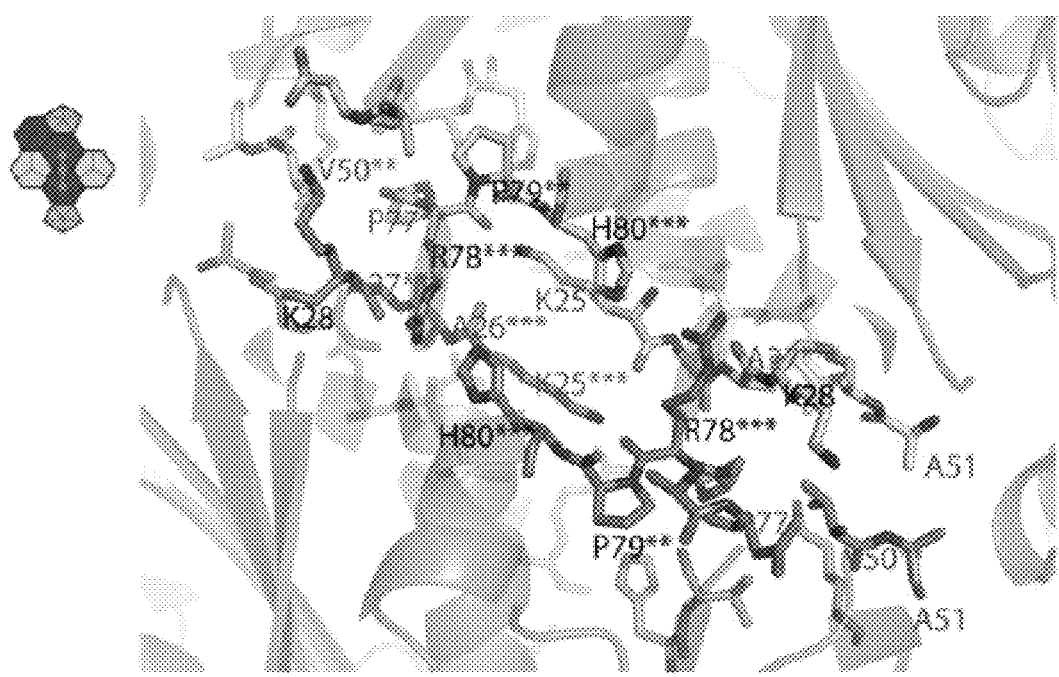
Figure 10B:
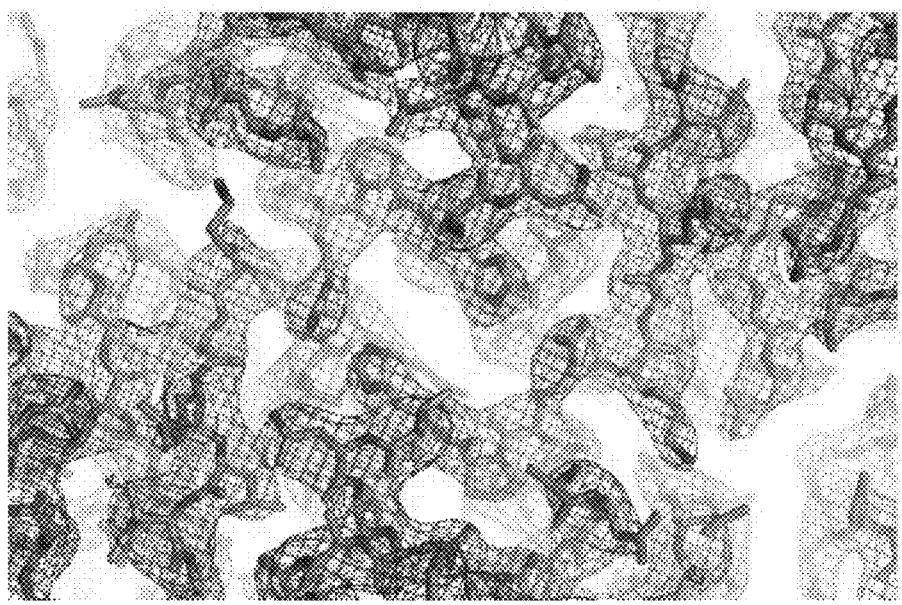

For the hexamer-hexamer interface (FIG. 9B), the KAA and PRPH motifs of complementing chains accounted for most of the interacting surface area. The lysines of the KAA motif were arranged in an antiparallel manner, creating a flat interaction surface with hydrogen bonds between the ε-amino group and the backbone oxygens of the opposite lysine and R78 (FIG. 9B). The coplanar hexamer-hexamer interface maintains the KAA-PRPH motif interactions, but contains an additional structural interdigitation between hexamers: the R78 side chain of the PRPH motif inserts in a pocket between the H80 side chain and backbone oxygens of V24, A27 and V29 of the adjacent hexamer (FIGS. 9C and 10B), creating an interlock. This was previously observed as a crystal packing interaction in the structure of the α-carboxysomal BMC-H protein CsoS1A (10), additional indication of the general structural conservation of the interactions across evolutionarily distant shell proteins (FIG. 13).

The specific sidechains influencing the interaction between the BMC-H hexamer and the BMC-T pseudohexamers are more enigmatic. The ability of three different BMC-T proteins to occupy the same position in the shell indicates a tolerance for a variety of sidechain interactions, according to some embodiments. The only universally conserved residue was the antiparallel lysine corresponding to the KAA motif in hexamers (FIGS. 14A-15B). Notably, all three BMC-Ts are able to occupy equivalent positions in the shell despite significant sequence divergence, suggesting that in the BMC-H:BMC-T interfaces, the specific interactions mediating assembly are based primarily on shape complementarity.

The surface view of the intact shell (FIGS. 6D and 7A-7D) showed it to be tightly packed; the only conduits to the interior of the shell were the pores formed at the cyclic symmetry axes of the hexamers and pseudohexamers. The largest channel to the interior was formed by the BMC-T proteins; the pore across the trimer within the facet is at least 5 Å wide with the potential to be larger due to flexibility of the loops surrounding the pore. The crystal structure of isolated BMC-T3 has both trimer pores closed while in the crystal structure of the isolated BMC-T2, one pore is open and the other closed, as has been observed before for carboxysome proteins (4), reminiscent of the alternate access model of some transmembrane transporters of eukaryotic organelles (e.g. BtuCD type ABC transporters (11)).

Figure 18A:
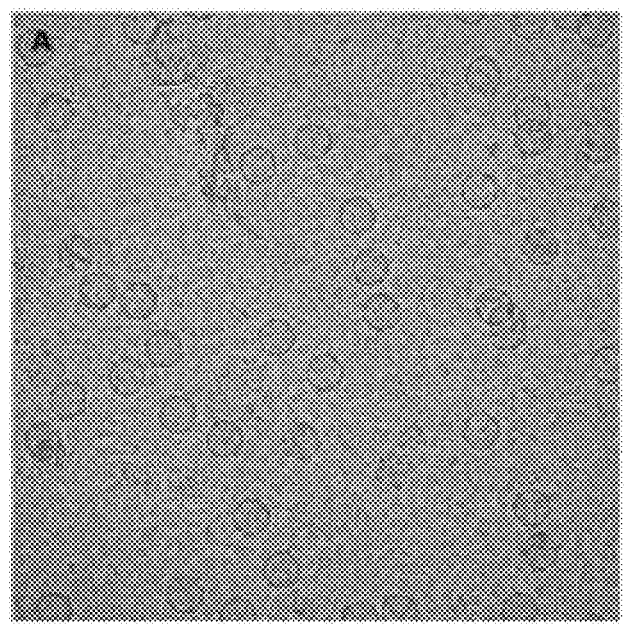
FIGS. 18A-18C depict an EM structure determination overview.

Using the interactions seen in the structure and the same set of hexamers, pseudohexamers and pentamers, larger compartments (T=36, diameter 720 Å) were modeled than had experimentally been observed by only slightly changing the angles between hexamers and pseudohexamers while maintaining the coplanar hexamer-hexamer contacts (FIGS. 16A and 16B). The extent of the facets was likely dictated by the interactions between different combinations of distinct BMC domains (i.e. the two different domains in each BMC-T paralog and the BMC-H) while the pentamer could prime the structure for an overall icosahedral shape. The subunits in the BMC-T positions thereby may influence the curvature and the final size of the compartment. This differs from previous hypothetical models which proposed specific proteins in forming edges (12, 13). Although the particles appear to have edges in some views and in micrographs (FIG. 16B, FIG. 18A), the curvature is distributed over the whole shell; larger BMCs effectively have less curvature per subunit. Accordingly, the structure determined here describes scalable principles for constructing a range of shell sizes, likely corresponding to the variation in shell sizes observed in BMCs in their native hosts, which range from 55-600 nm (14, 15).

The presence of structurally redundant building blocks suggests that the multiplicity is related to function, not structure, for example, to provide a range of conduits (i.e. differing in size and charge at the cyclic symmetry axes) for different metabolites (substrates and products) to cross the same shell. A second function would be to provide distinct patches on the interior surface to anchor and spatially organize the encapsulated enzymes. When the shell was modeled with the different BMC-Ts, an electrostatic (inside) surface view showed different regions that could be involved in specific interactions with the cargo proteins (FIG. 17). The distinct convex binding surfaces of the different shell proteins could serve to position the encapsulated enzymes to channel substrates and products between enzymes as well as across the shell.

Our model of the basic architecture of the bacterial microcompartment shell likely applies to functionally diverse organelles found across the Bacterial Kingdom; it also can inform rational design of engineered microcompartments. For the BMC shell described here, based on an inner diameter of 290 Å and assuming a typical protein density, there is space for approximately 150 copies of a 60 kDa enzyme in the interior, ample volume in which to localize multiple enzymes. Targeting may be achieved by either using specific encapsulation peptides found associated with the native cargo proteins (7, 16) or engineered using the structure of the inner surface as guide. The overall structure of the BMC shell invites comparisons to viral capsids and their engineered functions. BMC shells offer an additional structural and functional feature, selective permeability. Collectively, the atomic resolution model of a BMC shell reveals construction principles of the membranes of these primitive, protein-based organelles that can be applied to understanding and manipulating their native and engineered functions.

EXAMPLE 4

Materials and Methods

Protein Expression, Purification and Crystallization

A plasmid construct co-expressing BMC-H, BMC-T1, BMC-T2 and BMC-T3 (Hoch-5815, Hoch-5812, Hoch-5816 and Hoch-3341, respectively) was cloned into *E. coli* BL21(DE3). Cells were grown at 37° C. until on OD600 nm of 0.8 at which point the temperature was lowered to 22° C. and protein expression was induced by adding 0.05 mM IPTG and the cells were incubated O/N. Cell pellets were resuspended in Buffer A (20 mM Tris pH 7.4, 50 mM NaCl); small amounts of powdered DNase was added and cells were lysed using a French Press at >1000 psi. The lysate was cleared using a 30' 27,000×g SS-34 spin at 4° C. The supernatant was treated with RNAseA (100 µg per 1 ml lysate) and the sample was incubated on a shaker at RT for 1 h. The sample was then applied on top of a 6 ml sucrose cushion (30% sucrose in Buffer A) and centrifuged in a Ti-70 rotor for 16 h at 257,000×g. The supernatant was discarded and the pellet gently resuspended in 2 ml Buffer A. Insolubilized matter was removed with a short (2 min) spin in an Eppendorf minifuge at 16,000×g at 4° C. The supernatant was applied on top of a continuous 10-50% sucrose gradient in Buffer A and centrifuged in a SW-28 swinging bucket rotor for 16 h at 70,000×g at 4° C. Gradient fractions were analyzed on SDS-PAGE and shell containing fractions were pooled and applied on a 5 ml MonoQ column equilibrated in Buffer A. The shells were then eluted by applying a 0-40% gradient of Buffer B (20 mM Tris pH 7.4, 1 M NaCl) over 20 column volumes.

Hoch-5814 BMC-P pentamer was expressed in *E. coli* from a pET vector based on pET21b, no extra sequences or purification tags were added. Expression and lysis were performed the same as for the shells; the cleared lysate was then applied on a column packed with TOYOPEARL SuperQ-650M resin and the pentamer was eluted by applying a 0-40% gradient of Buffer B. Fractions containing pentamer were pooled, concentrated using a Millipore Amicon Ultra-15 concentrator with a 10 kDa molecular weight cut-off and applied on a GE HiLoad 26/60 Superdex 75 size exclusion column.

Purified *H. ochraceum* shells without pentamer were then mixed with a >10× excess (from expected pentamer occupancy) of separately purified pentamer, incubated with slow shaking at room temperature for 1 h and applied on MonoQ which separated the excess pentamer from the complete shells. Shell fractions were then pooled and concentrated/buffer exchanged to Buffer A using a Millipore Amicon Ultra-15 concentrator with a 100 kDa molecular weight cut-off. Shells were concentrated to A280 absorption of 2-4 and used to screen for crystallization using an Art Robbins Crystal Phoenix robot. An initial hit was improved in 24-well trays and gave rhombohedral shaped crystals up to 0.2 mm in length in conditions of 5-7% PEG-20000, 0.1 M Bicine pH 8.7-9.1 with 4 µl of protein mixed with 2 µl of reservoir in a sitting drop plate. Crystals were stabilized by addition of reservoir solution containing 30% ethylene glycol, looped and flash frozen in liquid nitrogen.

The pET11-based plasmids containing a sequence coding for BMC-T2 (Hoch-5816) or BMC-T3 (Hoch-3341) were transformed into *E. coli* BL21 (DE3), and cells were grown in LB broth (Miller) with 100 mg/L ampicillin at 37° C. and 160 rpm until the OD600 nm reached 0.8. IPTG was added to the culture (0.45 mM) and cells were grown for 4 h at the same temperature. Inclusion bodies containing BMC-T2 or BMC-T3 were purified and solubilized, and proteins were refolded using a protocol adapted from Burgess (18). Cells were resuspended in 50 mM Tris pH 7.8, 150 mM NaCl, 10 mM MgCl2 and 5 mM β-mercaptoethanol (buffer C) and lysed in presence of DNase using a French Press at >1000 psi. Triton X-100 was added to a final concentration of 1% (v/v), cell lysate was incubated for 15 min at RT with gentle shaking and centrifuged at 20,000×g for 10 min. The pellets containing the inclusion bodies were repeatedly washed with buffer C containing 1% Triton X-100, and a final wash without Triton X-100 was performed to remove all traces of detergent. BMC-T2 and BMC-T3 inclusion bodies were solubilized in buffer C containing 8 M urea. Protein concentration was adjusted to 1 mg/ml and refolding was performed by adding the protein quickly (60-fold dilution) to 50 mM Tris pH 7.8, 150 mM NaCl, 5% (v/v) glycerol. DTT was added to 0.5 mM in the case of BMC-T3. The diluted proteins were concentrated using a Millipore Amicon stirred cell (30 kDa molecular weight cut-off) and centrifuged to remove aggregates. For protein crystallization, BMC-T2 and BMC-T3 were buffer-exchanged using GE Healthcare PD-10 columns to 10 mM Tris pH 7.8, 50 mM NaCl and 10 mM Tris pH 7.8, respectively. BMC-T2 crystals were obtained in sitting drop trays by mixing 3 µl of protein (1.5 mg/ml) and 1 µl of a reservoir condition containing 0.1 M Na Acetate pH 5.1, 1.6 M MgSO4. Cryoprotection was achieved using 25% ethylene glycol in reservoir solution before crystal looping and flash freezing in liquid nitrogen. BMC-T3 was crystallized using 0.1 M Na cacodylate pH 6.5, 1.25 M Na citrate (protein concentration of 2 mg/ml, protein/reservoir ratio of 3:1) and cryo stabilized by addition of glycerol to 20%.

Data Collection, Analysis and Structure Determination

Data for *H. ochraceum* shells was collected at SSRL beam line 12.2 (100K, wavelength of data collection 1.03317 Å) diffracting to about 3.5 Å. The crystals belong to space group C2221 and the unit cell dimensions are 394×638×642 Å. Diffraction data were integrated with XDS (19) and scaled with SCALA (CCP4) (20). Self-rotation functions calculated from the data confirmed the icosahedral nature and from Matthew's coefficient calculations we expected half of a particle in the asymmetric unit. A low resolution (8.7 Å) cryo-electron microscopy density of the whole particle allowed constructing a model by placing the known structures of the hexameric and pentameric subunits which was of suitable quality for molecular replacement. A single solution had slightly higher Z scores and density averaging using icosahedral symmetry operators confirmed the correctness of this solution and enabled exact placement of the subunits for refinement and model building. Manual rebuilding/refinement cycles using COOT (21) and phenix.refine (22) led to a model with good geometry with regards to the resolution, 91.3% are in the favored, 7.2% allowed and 1.5% in the outlier region of the Ramachandran plot. Data for BMC-T2 and BMC-T3 was collected at the ALS beam line 5.0.2 (100K, wavelength of data collection 1.000 Å). BMC-T2 and BMC-T3 structures were solved using molecular replacement with CcmP (4HT5) as a search model and manually rebuilt/refined with COOT/phenix.refine. 98/97% are in the favored and 2/3% in the allowed region of the Ramachandran plot for BMC-T3 and BMC-T2, respectively with 1% rotamer outliers.

Cryo-EM Specimen Preparation, Data Acquisition and Processing

For cryo-EM specimen preparation, C-flat 1.2/1.3 holey carbon grids (Protochips, Morrisville, N.C., USA) were covered with a continuous carbon film and plasma cleaned using a SOLARUS plasma cleaner (Gatan, Pleasanton, Calif., USA). 4 µl of a 3 mg/ml solution of *H. ochraceum* shells were incubated on the plasma-cleaned grids for 5-7 s in a Vitrobot Mk. IV (FEI Company, Hillsboro, Oreg., USA) before plunge-freezing in liquid ethane at liquid N2 temperature. Cryo-EM data were collected using the LEGINON package (23) on a Tecnai F20 transmission cryo-electron microscope (FEI Company) operated at 120 kV acceleration voltage and equipped with a US4000 CCD camera (Gatan). Image acquisition was performed using a dose of 25 electrons/Å2, defocus values of −1.5 to −3.0 µm, and a magnification of 107,142×, resulting in a pixel size of 1.4 Å on the object scale.

Figure 18B:
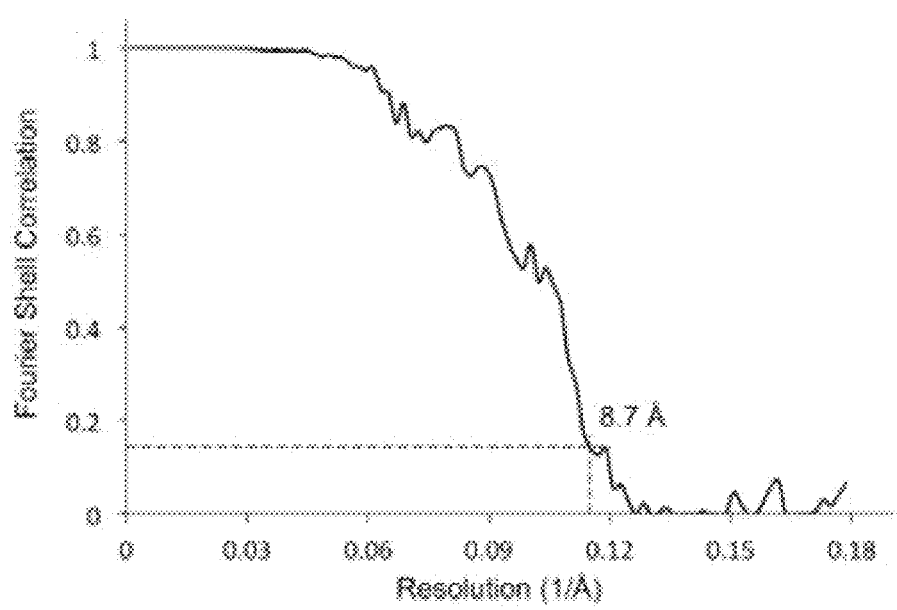
Figure 18C:
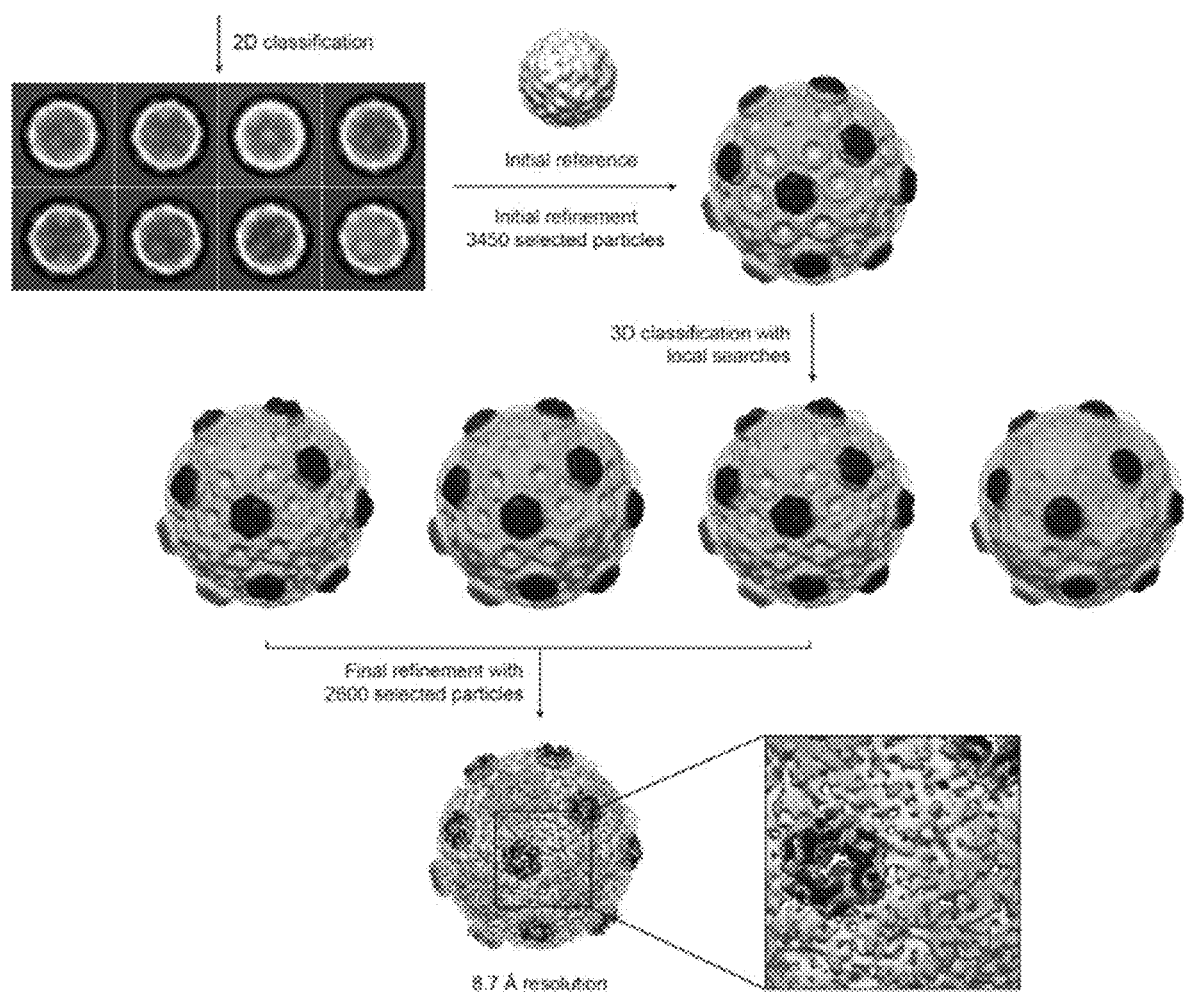

Images and power spectra were inspected using the APPION package (24), and images showing excessive ice contamination or drift were rejected. Defocus values were estimated using CTFFIND4 (25) from within RELION (26). Initially, particles were picked using DOG PICKER (27) in APPION (24) and subjected to 2D classification in RELION (26). These initial 2D classes were used as templates for automated particle selection in RELION 1.4 (26). Subsequent processing steps were performed using RELION 1.4 (26) and are detailed in FIGS. 18A-18C. A total of approximately 3750 particles were extracted from the micrographs, 2× binned (resulting in a pixel size of 2.8 Å on the object scale), and subjected to reference-free 2D classification. 3450 particles contained in the 2D classes showing near-spherical particles were refined imposing icosahedral symmetry, using as an initial reference a low-pass filtered shell of an icosahedral virus (28) (EMD-3351) rescaled to the approximate diameter of the H. ochraceum shell. The resulting cryo-EM map no longer resembles the initial reference, indicating that this reconstruction represents the structure of the H. ochraceum shell and is free from model bias. The angular assignments obtained in this initial refinement were used for 3D classification of the aligned particles using local angular searches. Two of the four classes showed only low-resolution features and the particles assigned to these classes were discarded. The remaining 2600 selected particles were split into fully independent half-sets (Gold-Standard refinement) and refined to 8.7 Å resolution according to the Fourier shell correlation (FSC)=0.143 criterion (29, 30).

Figure Generation and Bioinformatics

Molecular structure figures were prepared with pymol (The PyMOL Molecular Graphics System, Version 1.7 Schrödinger, LLC). The Cryo-EM H. ochraceum shell figure was rendered in UCSF Chimera (31) and Persistence of Vision Ray Tracer (Persistence of Vision Pty. Ltd. (2004), Persistence of Vision Raytracer (Version 3.6), Retrieved from www.povray.org/download). Sequences were aligned with ClustalX (32), phylogenetic trees were generated with PhyML (33) with default parameters and visualized with Archaeopteryx (34).

TABLE 1

X-ray crystallography data collection and refinement statistics.

| | H. ochraceum Shell | H. ochraceum BMC-T2 | H. ochraceum BMC-T3 |
|---|---|---|---|
| Data collection | | | |
| Space group | C 2 2 2$_1$ | P 2$_1$ 2$_1$ 2 | P 2$_1$ 3 |
| Unit cell dimensions | | | |
| a, b, c (Å) | 394.3, 638.1, 642.2 | 68.1, 126.1, 139.8 | 110.6, 110.6, 110.6 |
| Resolution (Å) | 40-3.51 (3.69-3.51) | 39-1.70 (1.79-1.70) | 39-1.55 (1.63-1.55) |
| Unique Reflections | 880,323 (135,274) | 131,926 (18,813) | 65,376 (9,459) |
| Rmerge | 1.32 (11.6) | 0.122 (1.61) | 0.103 (1.80) |
| Rpim | 0.33 (2.9) | 0.033 (0.43) | 0.016 (0.27) |
| Wilson B (Å2) | 85 | 19.8 | 22.3 |
| CC1/2 | 0.94 (0.26) | 0.999 (0.70) | 1.000 (0.87) |
| I/σI | 3.6 (0.4) | 21.0 (2.0) | 26.9 (2.6) |
| Completeness (%) | 98.2 (92.7) | 99.4 (97.9) | 100.0 (100.0) |
| Redundancy | 15.8 (13.9) | 14.8 (14.8) | 42.6 (44.0) |
| Refinement | | | |
| Resolution (Å) | 40-3.51 | 39-1.70 | 39-1.55 |
| Number of reflections | 878,895 | 131,795 | 65,297 |
| $R_{work}/R_{free}$ | 27.9/32.4 | 22.5/26.2 | 15.7/17.1 |
| Number of atoms | | | |
| Protein | 215,283 | 9,164 | 3,504 |
| Ligand/ion | n/a | n/a | 6 |
| Water | n/a | n/a | 386 |
| B-factors | | | |
| Protein | 102 | 26.3 | 23.5 |
| Ligand/ion | n/a | n/a | 34.4 |
| Water | n/a | 29.9 | 38.4 |
| R.m.s. deviations | | | |
| Bond lengths (Å) | 0.005 | 0.003 | 0.009 |
| Bond angles (°) | 0.86 | 0.57 | 1.09 |

Table 1 shows X-ray crystallography data collection and refinement statistics for the H. ochraceum shell, BMC-T2 and BMC-T3 structures. Statistics for the highest-resolution shell are shown in parentheses.

EXAMPLE 4

References

1. Shively J M, Ball F, Brown D H, Saunders R E. Science. 1973; 182:584-586. [PubMed: 4355679]

2. Axen S D, Erbilgin O, Kerfeld C A. PLoS Comput Biol. 2014; 10:e1003898. [PubMed: 25340524]

3. Kerfeld C A, et al. Science. 2005; 309:936-938. [PubMed: 16081736]

4. Klein M G, et al. J Mol Biol. 2009; 392:319-333. [PubMed: 19328811]

5. Cai F, et al. J Biol Chem. 2013; 288:16055-16063. [PubMed: 23572529]

6. Tanaka S, et al. Science. 2008; 319:1083-1086. [PubMed: 18292340]

7. Lassila J K, et al. J Mol Biol. 2014

8. Sutter M, et al. Nano Letters. 2016; 16:1590-1595. [PubMed: 26617073]

9. Aussignargues C, et al. J Am Chem Soc. 2016; 138: 5262-5270. [PubMed: 26704697]

10. Tsai Y, et al. PLoS Biol. 2007; 5:e144. [PubMed: 17518518]

11. Locher K P, Lee A T, Rees D C. Science. 2002; 296:1091-1098. [PubMed: 12004122]

12. Tanaka S, Sawaya M R, Yeates T O. Science. 2010; 327:81-84. [PubMed: 20044574]

13. Mallette E, Kimber M S. J Biol Chem. 2017; 292: 1197-1210. [PubMed: 27927988]

14. Erbilgin O, McDonald K L, Kerfeld C A. Appl Environ Microbiol. 2014; 80:2193-2205. [PubMed: 24487526]

15. Liberton M, Austin J R 2nd, Berg R H, Pakrasi H B. Plant Physiol. 2011; 155:1656-1666. [PubMed: 21173021]

16. Aussignargues C, et al. Commun Integr Biol. 2015; 8:e1039755. [PubMed: 26478774]

17. Burgess R R. Methods Enzymol. 2009; 463:259-282. [PubMed: 19892177]

18. Kabsch W. Acta Cryst D. 2010; 66:125-132. [PubMed: 20124692]

19. Winn M D, et al. Acta Cryst D. 2011; 67:235-242. [PubMed: 21460441]

20. Emsley P, Cowtan K. Acta Cryst D. 2004; 60:2126-2132. [PubMed: 15572765]

21. Afonine P V, et al. Acta Cryst D. 2012; 68:352-367. [PubMed: 22505256]

22. Suloway C, et al. J Struct Biol. 2005; 151:41-60. [PubMed: 15890530]

23. Lander G C, et al. J Struct Biol. 2009; 166:95-102. [PubMed: 19263523]

24. Rohou A, Grigorieff N. J Struct Biol. 2015; 192:216-221. [PubMed: 26278980]

25. Scheres S H W. J Struct Biol. 2012; 180:519-530. [PubMed: 23000701]

26. Voss N R, et al. J Struct Biol. 2009; 166:205-213. [PubMed: 19374019]

27. Okamoto K, et al. Sci Rep. 2016; 6:33170. [PubMed: 27616740]

28. Scheres S H W, Chen S. Nat Meth. 2012; 9:853-854.

29. Rosenthal P B, Henderson R. J Mol Biol. 2003; 333:721-745. [PubMed: 14568533]

30. Pettersen E F, et al. J Comput Chem. 2004; 25:1605-1612. [PubMed: 15264254]

31. Larkin M A, et al. Bioinformatics. 2007; 23:2947-2948. [PubMed: 17846036]

32. Guindon S, et al. Syst Biol. 2010; 59:307-321. [PubMed: 20525638]

33. Han M V, Zmasek C M. BMC Bioinformatics. 2009; 10:356. [PubMed: 19860910]

EXAMPLE 5

Electrostatic Encapsulation

Figure 19A:
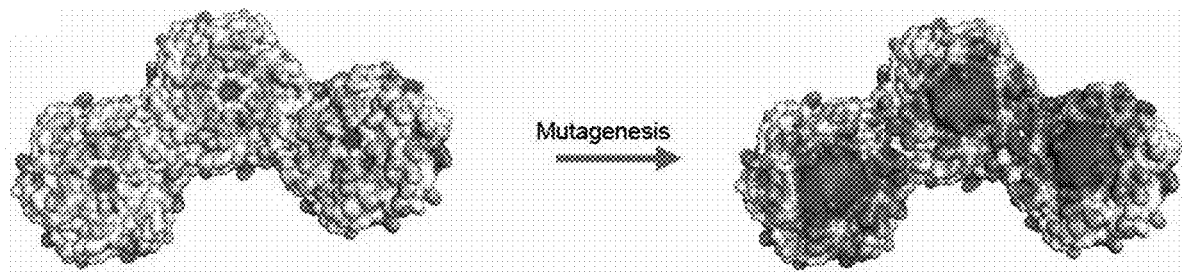
FIG. 19A is a depiction of a molecular model of a BMC-H protein mutagenized to change its electrostatic potential.

One embodiment was a method aimed to create a positively charged HO shell lumen to facilitate encapsulation of negatively charged cargo through electrostatic interactions. To do so, the strategy involved modifying the charge of the major shell component, BMC-H, to be more positive, thus increasing the net positive charge of the BMC lumen. The convex side of HO BMC-H, which faces the lumen, had an overall negative charge (FIG. 19A). Three Glu residues (E58, E65, and E69) were identified on the convex side, and two were mutated to Arg residues. Thereby, three double Arg variants were constructed. Each variant was heterologously expressed in E. coli with T1 and P1, and the co-expressed shell proteins were purified using affinity chromatography. A DLS analysis was performed. Based on that analysis, BMC-H_E65R, E69R was the only variant, of the three variants, that assembled into minimal shells (mHO) with the other shell proteins. A SUMO domain was then added to the N-terminus of BMC-H_E65R, E69R (SUMO-H$^+$), and the formation of mHO positive (mHO$^+$) shells was tested for in vitro. The DLS and an SDS-Page analysis of purified mHO$^+$ shells showed species with a diameter of 69 nm and the presence of all three shell components, respectively. Moreover, the TEM analysis revealed shells with an average diameter comparable to the diameter of minimal WT HO shells.

Figure 19B:
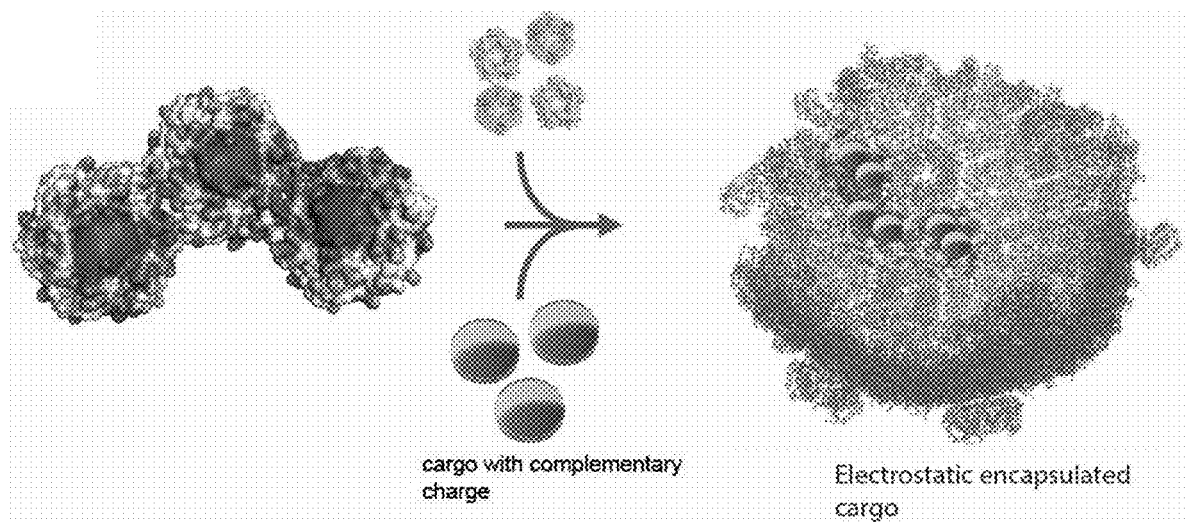
FIG. 19B is a depiction of cargo being encapsulated electrostatically by mutagenized BMC-H proteins.
Figure 19C:
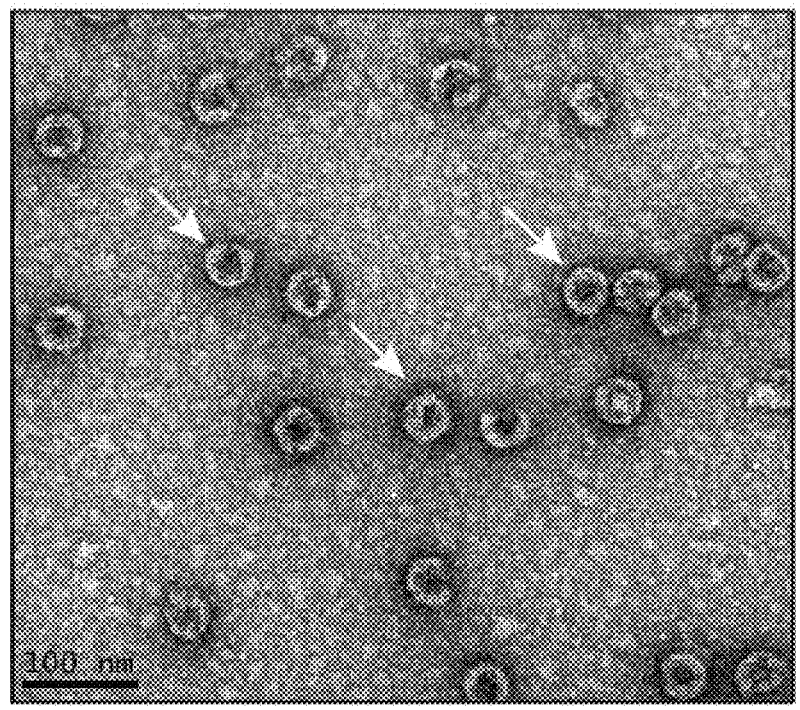
FIG. 19C is a TEM micrograph of shells assembled in vivo and containing material encapsulated electrostatically.

FIGS. 19A-19C depict a strategy for electrostatic-based encapsulation into shells and TEM of electrostatics-mediated cargo encapsulation. FIG. 19A shows a molecular model shaded by electrostatic potential of wildtype BMC-H proteins and mutagenized variants indicating change in electrostatic potential resulting from mutations. FIG. 19B is an illustration of encapsulation of cargo with complementary electrostatic charge. Only part of the shell is rendered for clarity. FIG. 19C shows a negative stain TEM image of in vitro assembled shells harboring electrostatics-encapsulated cargo. White arrows point to examples of shells. A thicker, stippled appearance of shells indicating encapsulated cargo was seen.

Thus, according to some embodiments, an electrostatic encapsulation strategy may be used to encapsulate a material within a BMC protein or BMC fusion protein. In some embodiments, the BMC protein or the BMC fusion protein is charged. The charge may be positive or negative. In some embodiments, the BMC protein or the BMC fusion protein is mutated from its original unmutated form, and has a different electrostatic potential than its unmutated form. In some embodiments, the material to be encapsulated has an opposite charge from the BMC fusion protein.

The above examples are provided to illustrate the present disclosure but not to limit its scope. Other variants of the present disclosure will be readily apparent to one of ordinary skill in the art and are encompassed by the appended claims. All publications, databases, and patents cited herein are hereby incorporated by reference for all purposes.

What is claimed is:

1. A fusion protein, comprising:

a Bacterial Microcompartment (BMC) shell protein comprising one or more subunits and capable of assembling in vitro selected from the group consisting of: Hoch 5815 (SEQ ID NO: 1), Hoch 5812 (SEQ ID NO: 3), Hoch 3341 (SEQ ID NO: 5), Hoch 5816 (SEQ ID NO: 7), Hoch 4425 (SEQ ID NO: 9), Hoch 4426 (SEQ ID NO: 11) and Hoch 5814 (SEQ ID NO: 13); and one or more sterically hindering protein domains comprising a Maltose Binding Protein (MBP) or a Short Ubiquitin-related Modifier (SUMO) protein operably linked to the one or more subunits of the BMC shell protein and capable of preventing assembly of the one or more subunits into bacterial microcompartment in vitro, wherein enzymatic removal of the one or more sterically hindering protein domains allow the one or more subunits of the BMC shell protein to form into bacterial micro compartments in vitro.

2. The fusion protein of claim 1, wherein the sterically hindering protein is enzymatically removable from the BMC shell protein by a protease.

3. The fusion protein of claim 1, wherein the protease is one of TEV protease, or Ulp protease.

4. The fusion protein of claim 1, further comprising a linker polypeptide operably linking the BMC shell proteins to the one or more sterically hindering protein domains.

5. The fusion protein of claim 4, wherein the linker polypeptide is specifically cleavable by a protease.

6. A method of producing a bacterial microcompartment, comprising:

Providing a fusion protein of claim 1 comprising a BMC shell protein having one or more subunits and one or more sterically hindering protein domains operably linked to the BMC shell protein;

cleaving the fusion proteins to remove the sterically hindering protein domains; and allowing bacterial micro compartments to form from the BMC shell proteins.

* * * * *

SEQUENCE LISTING

<160> NUMBER OF SEQ ID NOS: 46

<210> SEQ ID NO 1
<211> LENGTH: 99
<212> TYPE: PRT

<213> ORGANISM: Haliangium ochraceum

<400> SEQUENCE: 1

```
Met Ala Asp Ala Leu Gly Met Ile Glu Val Arg Gly Phe Val Gly Met
1               5                   10                  15

Val Glu Ala Ala Asp Ala Met Val Lys Ala Ala Lys Val Glu Leu Ile
            20                  25                  30

Gly Tyr Glu Lys Thr Gly Gly Tyr Val Thr Ala Val Val Arg Gly
        35                  40                  45

Asp Val Ala Ala Val Lys Ala Ala Thr Glu Ala Gly Gln Arg Ala Ala
    50                  55                  60

Glu Arg Val Gly Glu Val Val Ala Val His Val Ile Pro Arg Pro His
65                  70                  75                  80

Val Asn Val Asp Ala Ala Leu Pro Leu Gly Arg Thr Pro Gly Met Asp
                85                  90                  95

Lys Ser Ala
```

<210> SEQ ID NO 2
<211> LENGTH: 300
<212> TYPE: DNA
<213> ORGANISM: Artificial Sequence
<220> FEATURE:
<223> OTHER INFORMATION: Synthetic DNA sequence

<400> SEQUENCE: 2

```
atggcggacg cactgggtat gattgaagtt cgtggttttg ttggtatggt ggaagcggcg    60
gatgctatgg tgaaagcggc taaagttgaa ctgattggtt atgaaaaaac cggcggtggc   120
tacgtgacgg cagtggttcg tggtgatgtc gcagcagtta aggcagctac cgaagccggt   180
cagcgtgcag cagaacgtgt tggtgaagtc gtggcagttc atgtcatccc gcgtccgcac   240
gtgaacgttg atgcagctct gccgctgggt cgtacgccgg gtatggacaa aagcgcgtaa   300
```

<210> SEQ ID NO 3
<211> LENGTH: 205
<212> TYPE: PRT
<213> ORGANISM: Haliangium ochraceum

<400> SEQUENCE: 3

```
Met Asp His Ala Pro Glu Arg Phe Asp Ala Thr Pro Pro Ala Gly Glu
1               5                   10                  15

Pro Asp Arg Pro Ala Leu Gly Val Leu Glu Leu Thr Ser Ile Ala Arg
            20                  25                  30

Gly Ile Thr Val Ala Asp Ala Ala Leu Lys Arg Ala Pro Ser Leu Leu
        35                  40                  45

Leu Met Ser Arg Pro Val Ser Ser Gly Lys His Leu Leu Met Met Arg
    50                  55                  60

Gly Gln Val Ala Glu Val Glu Glu Ser Met Ile Ala Ala Arg Glu Ile
65                  70                  75                  80

Ala Gly Ala Gly Ser Gly Ala Leu Leu Asp Glu Leu Glu Leu Pro Tyr
                85                  90                  95

Ala His Glu Gln Leu Trp Arg Phe Leu Asp Ala Pro Val Val Ala Asp
                100                 105                 110

Ala Trp Glu Glu Asp Thr Glu Ser Val Ile Ile Val Glu Thr Ala Thr
            115                 120                 125

Val Cys Ala Ala Ile Asp Ser Ala Asp Ala Ala Leu Lys Thr Ala Pro
        130                 135                 140
```

Val Val Leu Arg Asp Met Arg Leu Ala Ile Gly Ile Ala Gly Lys Ala
145                 150                 155                 160

Phe Phe Thr Leu Thr Gly Glu Leu Ala Asp Val Glu Ala Ala Ala Glu
                165                 170                 175

Val Val Arg Glu Arg Cys Gly Ala Arg Leu Leu Glu Leu Ala Cys Ile
            180                 185                 190

Ala Arg Pro Val Asp Glu Leu Arg Gly Arg Leu Phe Phe
        195                 200                 205

<210> SEQ ID NO 4
<211> LENGTH: 618
<212> TYPE: DNA
<213> ORGANISM: Artificial Sequence
<220> FEATURE:
<223> OTHER INFORMATION: Synthetic DNA sequence

<400> SEQUENCE: 4
atggaccacg ctccggaacg ctttgatgcg accccgccgg caggtgaacc ggaccgcccg      60
gcactgggtg tgctggaact gacctcaatt gctcgtggta tcaccgttgc ggatgcggcc     120
ctgaaacgtg caccgagtct gctgctgatg tcccgcccgg tcagctctgg caagcatctg     180
ctgatgatgc gtggccaggt ggcagaagtt gaagaatcaa tgattgcagc tcgcgaaatc     240
gctggtgcag ttcgggtgc tctgctggat gaactggaac tgccgtatgc gacgaacaa      300 ctgtggcgct ttctggacgc accggtggtt gcagatgcat gggaagaaga caccgaaagc     360
gtcattatcg tggaaaccgc gacggtgtgc gcggccattg atagtgccga cgcagctctg     420
aaaacggcac cggtcgtgct gcgtgatatg cgcctggcca ttggtatcgc tggcaaggcg     480 ttttcaccc tgacgggtga actggcagac gtggaagcgg ccgcagaagt tgtccgtgaa      540
cgttgcggtg cacgtctgct ggaactggca tgtatcgcac gccgggttga tgaactgcgt     600
ggccgcctgt ttttctaa                                                   618

<210> SEQ ID NO 5
<211> LENGTH: 206
<212> TYPE: PRT
<213> ORGANISM: Haliangium ochraceum

<400> SEQUENCE: 5

Met Glu Leu Arg Ala Tyr Thr Val Leu Asp Ala Leu Gln Pro Gln Leu
1               5                   10                  15

Val Ala Phe Leu Gln Thr Val Ser Thr Gly Phe Met Pro Met Glu Gln
                20                  25                  30

Gln Ala Ser Val Leu Val Glu Ile Ala Pro Gly Ile Ala Val Asn Gln
            35                  40                  45

Leu Thr Asp Ala Ala Leu Lys Ala Thr Arg Cys Gln Pro Gly Leu Gln
        50                  55                  60

Ile Val Glu Arg Ala Tyr Gly Leu Ile Glu Met His Asp Asp Asp Gln
65                  70                  75                  80

Gly Gln Val Arg Ala Ala Gly Asp Ala Met Leu Ala His Leu Gly Ala
                85                  90                  95

Arg Glu Ala Asp Arg Leu Ala Pro Arg Val Val Ser Ser Gln Ile Ile
            100                 105                 110

Thr Gly Ile Asp Gly His Gln Ser Gln Leu Ile Asn Arg Met Arg His
        115                 120                 125

Gly Asp Met Ile Gln Ala Gly Gln Thr Leu Tyr Ile Leu Glu Val His
    130                 135                 140

Pro Ala Gly Tyr Ala Ala Leu Ala Ala Asn Glu Ala Glu Lys Ala Ala
145                 150                 155                 160

Pro Ile Lys Leu Leu Glu Val Val Thr Phe Gly Ala Phe Gly Arg Leu
            165                 170                 175

Trp Leu Gly Gly Gly Glu Ala Glu Ile Ala Glu Ala Ala Arg Ala Ala
            180                 185                 190

Glu Gly Ala Leu Ala Gly Leu Ser Gly Arg Asp Asn Arg Gly
            195                 200                 205

<210> SEQ ID NO 6
<211> LENGTH: 621
<212> TYPE: DNA
<213> ORGANISM: Artificial Sequence
<220> FEATURE:
<223> OTHER INFORMATION: Synthetic DNA sequence

<400> SEQUENCE: 6
atggaactgc gtgcttatac ggtcctggat gccctgcagc cgcaactggt cgcctttctg        60
caaacggtgt caacgggttt catgccgatg aacagcaag cgagcgttct ggtcgaaatt       120
gcaccgggta tcgctgtcaa ccagctgacc gacgcagcac tgaaagcaac gcgttgccag      180
ccgggtctgc aaattgtgga acgtgcgtat ggcctgatcg aaatgcatga tgacgatcag      240
ggtcaagttc gtgcagctgg tgacgcaatg ctggcacacc tgggtgcacg tgaagctgat      300
cgtctggcac gcgtgtggt tagctctcag attatcaccg gtattgacgg ccatcagagt       360
caactgatca accgtatgcg ccacggtgat atgattcagg caggccaaac gctgtatatc      420
ctggaagttc atccggcagg ttacgcagca ctggcagcta tgaagccga aaaagcggcc       480 ccgattaagc tgctggaagt cgtgaccttt ggtgcattcg gtcgtctgtg gctgggtggt      540
ggtgaagcag aaatcgcaga agcagctcgt gcggcagaag gtgcactggc tggtctgtcc     600
ggccgtgata tcgcggcta a                                                621

<210> SEQ ID NO 7
<211> LENGTH: 212
<212> TYPE: PRT
<213> ORGANISM: Haliangium ochraceum

<400> SEQUENCE: 7

Met Ser Ile Thr Leu Arg Thr Tyr Ile Phe Leu Asp Ala Leu Gln Pro
1               5                   10                  15

Gln Leu Ala Thr Phe Ile Gly Lys Thr Ala Arg Gly Phe Leu Pro Val
            20                  25                  30

Pro Gly Gln Ala Ser Leu Trp Val Glu Ile Ala Pro Gly Ile Ala Ile
        35                  40                  45

Asn Arg Val Thr Asp Ala Ala Leu Lys Ala Thr Lys Val Gln Pro Ala
50                  55                  60

Val Gln Val Val Glu Arg Ala Tyr Gly Leu Leu Glu Val His His Phe
65                  70                  75                  80

Asp Gln Gly Glu Val Leu Ala Ala Gly Ser Thr Ile Leu Asp Lys Leu
                85                  90                  95

Glu Val Arg Glu Glu Gly Arg Leu Lys Pro Gln Val Met Thr His Gln
            100                 105                 110

Ile Ile Arg Ala Val Glu Ala Tyr Gln Thr Gln Ile Ile Asn Arg Asn
        115                 120                 125

Ser Gln Gly Met Met Ile Leu Pro Gly Glu Ser Leu Phe Ile Leu Glu
    130                 135                 140

```
Thr Gln Pro Ala Gly Tyr Ala Val Leu Ala Ala Asn Glu Ala Glu Lys
145                 150                 155                 160

Ala Ala Asn Val His Leu Val Asn Val Thr Pro Tyr Gly Ala Phe Gly
                165                 170                 175

Arg Leu Tyr Leu Ala Gly Ser Glu Ala Glu Ile Asp Ala Ala Ala Glu
            180                 185                 190

Ala Ala Glu Ala Ala Ile Arg Ser Val Ser Gly Val Ala Gln Glu Ser
        195                 200                 205

Phe Arg Asp Arg
    210

<210> SEQ ID NO 8
<211> LENGTH: 639
<212> TYPE: DNA
<213> ORGANISM: Artificial Sequence
<220> FEATURE:
<223> OTHER INFORMATION: Synthetic DNA sequence

<400> SEQUENCE: 8
atgtcaatca ccctgcgcac ctatatcttt ctggacgccc tgcaaccgca actggcaacc      60
ttcatcggca aaacggctcg tggcttcctg ccggtcccgg tcaggcaag cctgtgggtg     120 gaaattgctc cgggtattgc gatcaaccgt gtgaccgatg cggccctgaa agctacgaag     180
gtgcagccgg cggttcaagt ggttgaacgc gcgtatggcc tgctggaagt tcatcacttc     240
gatcagggcg aagtcctggc agctggtagt accatcctgg acaaactgga agttcgtgaa     300
gaaggtcgcc tgaagccgca ggtgatgacc atcaaattac cgtgctgt gaagcgtat      360 cagacgcaaa ttatcaaccg caatagtcag ggcatgatga ttctgccggg tgaatccctg     420
tttatcctgg aaacccaacc ggcaggttac gcagtcctgg cagccaatga agccgaaaaa     480
gcagctaacg ttcacctggt caatgtgacg ccgtatggcg cattcggtcg tctgtacctg     540
gccggctcag aagcagaaat tgatgcggcc gcagaagctg cggaagccgc aatccgcagc     600
gtttctggtg tcgcgcagga atcgtttcgt gaccgctaa                            639

<210> SEQ ID NO 9
<211> LENGTH: 92
<212> TYPE: PRT
<213> ORGANISM: Haliangium ochraceum

<400> SEQUENCE: 9

Met Tyr Leu Gly Arg Val Ile Gly Thr Val Val Ala Glu Arg Lys Val
1               5                   10                  15

Ala Gly Leu Glu Gly Ala Lys Leu Leu Val Gln Pro Leu Asp Asp
            20                  25                  30

Ala Leu Ser Pro Val Gly Gly Val Gln Ala Ala Val Asp Thr Val Gln
        35                  40                  45

Ala Gly Pro Asp Asp Leu Val Tyr Leu Val Gly Ser Arg Glu Ala Ala
    50                  55                  60

Leu Ala Leu Thr Pro Ser Phe Val Pro Val Asp Ala Ala Ile Val Gly
65                  70                  75                  80

Ile Val Asp Asp Val His Ala Pro Glu Arg Ala Ser
                85                  90

<210> SEQ ID NO 10
<211> LENGTH: 279
<212> TYPE: DNA
<213> ORGANISM: Artificial Sequence
<220> FEATURE:
```

<223> OTHER INFORMATION: Synthetic DNA sequence

<400> SEQUENCE: 10

```
atgtatctgg gtcgtgtgat tggtaccgtg gtggctgaac gcaaagtggc gggtctggaa      60
ggcgcaaaac tgctgctggt gcaaccgctg gatgacgcac tgagtccggt cggtggtgtg     120
caggcagcag ttgataccgt ccaagcaggt ccggatgacc tggtgtatct ggttggtagc     180
cgtgaagcag ctctggcgct gacgccgtct tttgtgccgg ttgatgcggc cattgtcggc     240
atcgttgatg acgtgcatgc accggaacgc gctagctaa                            279
```

<210> SEQ ID NO 11
<211> LENGTH: 127
<212> TYPE: PRT
<213> ORGANISM: Haliangium ochraceum

<400> SEQUENCE: 11

```
Met Arg Leu Cys Arg Val Leu Gly Ser Val Val Ala Thr Val Lys His
1               5                   10                  15
Pro Val Tyr Asn Gly Leu Pro Leu Met Ile Val Gln Pro Leu Asp Asp
            20                  25                  30
Ala Gly Arg Asp Ala Gly Ala Ser Phe Leu Ala Val Asp Asn Val Gln
        35                  40                  45
Ser Gly Pro Gly Asp Arg Val Leu Val Leu Thr Glu Gly Gly Gly Val
    50                  55                  60
Arg Gln Ile Leu Ala Leu Gly Asp Gln Val Pro Ile Arg Ser Leu Ile
65                  70                  75                  80
Val Gly Val Val Asp Ala Val Asp Gly Val Ala Ala Thr Gly Val Asp
                85                  90                  95
Asp Ala Gly Gly Ala Ala Asp Ser Ala Ala Ala Lys Ser Val Arg
            100                 105                 110
Ala Asp Glu Leu Pro Ala Asp Ala Ser Ala Ala Gly Arg Gly Glu
        115                 120                 125
```

<210> SEQ ID NO 12
<211> LENGTH: 384
<212> TYPE: DNA
<213> ORGANISM: Artificial Sequence
<220> FEATURE:
<223> OTHER INFORMATION: Synthetic DNA sequence

<400> SEQUENCE: 12

```
atgcgtctgt gtcgtgttct gggctccgtc gtcgccaccg tcaagcaccc ggtctacaat      60
ggtctgccgc tgatgatcgt tcaaccgctg gatgacgcag gtcgtgatgc aggcgctagt     120
tttctggctg ttgataacgt ccagtccggt ccgggtgacc gtgtcctggt gctgaccgaa     180
ggtggtggtg tgcgtcagat tctggcactg ggtgatcaag tcccgattcg cagcctgatc     240
gtgggcgtgg ttgatgcagt ggacggtgtt gcagcaacgg tgttgatga cgcaggtggt     300
gcagctgata gcgcagcagc agctaaatct gtccgtgcag atgaactgcc ggcagacgca     360
agcgcggccg gtcgcggcga ataa                                            384
```

<210> SEQ ID NO 13
<211> LENGTH: 96
<212> TYPE: PRT
<213> ORGANISM: Haliangium ochraceum

<400> SEQUENCE: 13

```
Met Val Leu Gly Lys Val Val Gly Thr Val Val Ala Ser Arg Lys Glu
```

```
            1               5                  10                 15
Pro Arg Ile Glu Gly Leu Ser Leu Leu Leu Val Arg Ala Cys Asp Pro
                20                  25                  30

Asp Gly Thr Pro Thr Gly Gly Ala Val Val Cys Ala Asp Ala Val Gly
            35                  40                  45

Ala Gly Val Gly Glu Val Val Leu Tyr Ala Ser Gly Ser Ser Ala Arg
        50                  55                  60

Gln Thr Glu Val Thr Asn Asn Arg Pro Val Asp Ala Thr Ile Met Ala
 65                 70                  75                  80

Ile Val Asp Leu Val Glu Met Gly Gly Asp Val Arg Phe Arg Lys Asp
                85                  90                  95
```

<210> SEQ ID NO 14
<211> LENGTH: 291
<212> TYPE: DNA
<213> ORGANISM: Artificial Sequence
<220> FEATURE:
<223> OTHER INFORMATION: Synthetic DNA sequence

<400> SEQUENCE: 14

```
atggtcctgg gtaaagtcgt gggtacggtg gtggcgagcc gcaaagaacc gcgcattgaa     60
ggtctgagcc tgctgctggt ccgtgcctgc gatccggacg gtaccccgac gggtggtgca    120
gtggtttgtg cagatgcagt gggtgcaggt gttggtgaag tcgtgctgta tgcgagtggc    180
agctctgccc gtcagaccga agtcacgaac aatcgcccgg ttgatgcaac cattatggct    240
atcgttgacc tggtcgaaat gggcggtgat gtgcgttttc gcaaagacta a             291
```

<210> SEQ ID NO 15
<211> LENGTH: 93
<212> TYPE: PRT
<213> ORGANISM: Mycobacterium smegmatis

<400> SEQUENCE: 15

```
Met Ser Ser Asn Ala Ile Gly Leu Ile Glu Thr Lys Gly Tyr Val Ala
 1               5                  10                  15

Ala Leu Ala Ala Ala Asp Ala Met Val Lys Ala Ala Asn Val Thr Ile
                20                  25                  30

Thr Asp Arg Gln Gln Val Gly Asp Gly Leu Val Ala Val Ile Val Thr
            35                  40                  45

Gly Glu Val Gly Ala Val Lys Ala Ala Thr Glu Ala Gly Ala Glu Thr
        50                  55                  60

Ala Ser Gln Val Gly Glu Leu Val Ser Val His Val Ile Pro Arg Pro
 65                 70                  75                  80

His Ser Glu Leu Gly Ala His Phe Ser Val Ser Ser Lys
                85                  90
```

<210> SEQ ID NO 16
<211> LENGTH: 282
<212> TYPE: DNA
<213> ORGANISM: Mycobacterium smegmatis

<400> SEQUENCE: 16

```
atgagcagca atgcaatcgg tctgatcgaa acgaaaggct atgtggcggc actggcagcg     60
gcggatgcaa tggtgaaggc agcaaatgtc accattacgg atcgtcagca agttggcgac    120
ggtctggtgg cggttatcgt caccggcgaa gtgggtgccg ttaaagcggc caccgaagca    180
ggcgctgaaa cggcaagtca agtgggtgaa ctggtgtccg ttcatgtcat tccgcgtccg    240
```
cacagcgaac tgggtgcaca ttttagcgtt agctctaagt aa                            282

<210> SEQ ID NO 17
<211> LENGTH: 202
<212> TYPE: PRT
<213> ORGANISM: Mycobacterium smegmatis

<400> SEQUENCE: 17

Met Ala Glu Leu Arg Ser Phe Ile Phe Ile Asp Arg Leu Gln Pro Gln
1               5                   10                  15

Thr Met Ser Tyr Leu Gly Thr Trp Ile Lys Gly Ala Leu Pro Arg Ala
            20                  25                  30

Asn Met Ala Ala Gln Ile Ile Glu Val Ala Pro Gly Leu Asp Ile Glu
        35                  40                  45

Gly Val Thr Asp Val Ala Leu Lys His Ala Glu Val Lys Ala Gly Ile
    50                  55                  60

Leu Val Val Glu Arg Gln Phe Gly Tyr Leu Glu Phe His Gly Glu Thr
65                  70                  75                  80

Gly Ala Val Lys Ala Ala Ala Asp Ala Ala Leu Asp Tyr Leu Gly Gly
                85                  90                  95

Asp Pro Asp Ala Ala Val Arg Pro Glu Ile Leu Ala Ser Arg Ile Ile
            100                 105                 110

Ser Ser Ile Asp His Gln His Ala Phe Leu Ile Asn Arg Asn Lys Ile
        115                 120                 125

Gly Ser Met Val Leu Pro Gly Glu Ser Leu Phe Val Leu Glu Val Ala
    130                 135                 140

Pro Ala Ser Tyr Ala Ile Leu Ala Thr Asn Glu Ala Glu Lys Ala Ala
145                 150                 155                 160

Asp Val Lys Val Val Asp Phe Arg Met Ile Gly Ala Thr Gly Arg Val
                165                 170                 175

Tyr Leu Ser Gly Thr Glu Ala Asp Val Arg Gln Ala Ala Asp Ala Ala
            180                 185                 190

Arg Asp Ala Leu Ala Val Leu Gln Gly Ala
        195                 200

<210> SEQ ID NO 18
<211> LENGTH: 609
<212> TYPE: DNA
<213> ORGANISM: Mycobacterium smegmatis

<400> SEQUENCE: 18
atggccgaac tgcgtagctt cattttcatt gaccgcctgc aaccgcaaac gatgtcctat    60
ctgggcacct ggattaaggg tgctctgccg cgtgcgaaca tggcggccca gattatcgaa   120
gttgccccgg gcctggatat tgaaggtgtt accgacgtcg ccctgaaaca tgcagaagtc   180
aaggctggca tcctggtggt tgaacgccaa tttggttatc tggaatttca tggcgaaacg   240
ggtgcggtga agcagctgc ggatgccgca ctggactacc tggtggtga tccggacgct   300 gcagttcgtc cggaaattct ggcctctcgc attatcagct ctatcgatca tcagcacgca   360
tttctgatta accgtaataa gatcggcagt atggtcctgc cgggtgaatc cctgttcgtg   420
ctggaagttg ctccggcgag ctatgcgatt ctggcgacca tgaagcgga aaaagccgca   480 gatgttaagg tcgtggactt cgtatgatc ggtgcaaccg gtcgtgtcta cctgtcgggc   540
acggaagctg atgtgcgtca ggctgcagat gcagcacgcg acgcactggc agtgctgcaa   600
ggtgcctaa                                                            609

<210> SEQ ID NO 19
<211> LENGTH: 87
<212> TYPE: PRT
<213> ORGANISM: Mycobacterium smegmatis

<400> SEQUENCE: 19

Met Leu Arg Ala Thr Val Thr Gly Asn Val Trp Ser Thr Arg Arg Ile
1               5                   10                  15

Glu Gly Ile Pro Ala Gly Ala Phe Leu Glu Val Glu Val Glu Gly Thr
            20                  25                  30

Gly Ser Arg Met Ile Ala Phe Asp Val Leu Gly Ser Gly Val Gly Glu
        35                  40                  45

His Val Leu Ile Ala Gln Gly Ser Val Ala Ser Ser Trp Phe Thr Gly
    50                  55                  60

Thr Pro Pro Ile Asp Ala Leu Ile Ile Gly Ser Ile Asp Thr Arg
65                  70                  75                  80

Ser Asp Ser Asn Pro Ala Glu
                85

<210> SEQ ID NO 20
<211> LENGTH: 264
<212> TYPE: DNA
<213> ORGANISM: Mycobacterium smegmatis

<400> SEQUENCE: 20
atgctgcgtg ctaccgttac cggcaatgtc tggtctaccc gtcgtatcga aggcatcccg        60
gctggtgctt ttctggaagt ggaagtcgaa ggcaccggtt cacgtatgat tgcctttgat       120
gtcctgggct cgggtgtggg cgaacatgtt ctgatcgcgc agggtagcgt tgccagctct       180
tggttcaccg gtacgccgcc gccgattgac gcactgatta tcggtagtat cgatacgcgc       240
agtgactcca acccggctga ataa                                              264

<210> SEQ ID NO 21
<211> LENGTH: 102
<212> TYPE: PRT
<213> ORGANISM: Thermosynechococcus elongatus

<400> SEQUENCE: 21

Met Pro Ile Ala Val Gly Met Ile Glu Thr Arg Gly Phe Pro Ala Val
1               5                   10                  15

Val Glu Ala Ala Asp Ala Met Val Lys Ala Ala Arg Val Thr Leu Val
            20                  25                  30

Gly Tyr Glu Lys Ile Gly Ser Gly Arg Val Thr Val Ile Val Arg Gly
        35                  40                  45

Asp Val Ser Glu Val Gln Ala Ser Val Ala Ala Gly Val Asp Ser Ala
    50                  55                  60

Lys Arg Val Asn Gly Gly Glu Val Leu Ser Thr His Ile Ile Ala Arg
65                  70                  75                  80

Pro His Glu Asn Leu Glu Tyr Val Leu Pro Ile Arg Tyr Thr Glu Ala
                85                  90                  95

Val Glu Gln Phe Arg Asn
            100

<210> SEQ ID NO 22
<211> LENGTH: 306
<212> TYPE: DNA
<213> ORGANISM: Artificial Sequence
<220> FEATURE:

<223> OTHER INFORMATION: Synthetic hexamer DNA sequence

<400> SEQUENCE: 22

```
atgccaattg ccgtgggtat gattgaaacc cgtggttttc cagccgtggt ggaagcggcc      60
gatgccatgg tgaaagccgc gcgtgttacc ctggtgggtt acgagaaaat cggtagtggt     120
cgtgtgaccg tgattgtgcg tggtgatgtg agtgaagtgc aagccagtgt tgcggccggt     180
gtggatagtg ccaaacgtgt gaatggtggc gaagtgctga gtacccatat cattgcccgt     240
ccacatgaaa atctggaata cgtgctgcca atccgttaca ccgaagccgt tgaacaattt     300
cgtaat                                                                306
```

<210> SEQ ID NO 23
<211> LENGTH: 253
<212> TYPE: PRT
<213> ORGANISM: Thermosynechococcus elongatus

<400> SEQUENCE: 23

```
Met Glu Arg Arg Asp Asp Phe Thr Asp Leu Ala Leu Gly Leu Val Ser
1               5                   10                  15
Val Gln Ser Phe Pro Ala Ile Val Gly Ile Ala Asp His Met Leu Lys
            20                  25                  30
Ser Ser Asp Val Leu Leu Val Gly Tyr Glu Lys Ile Gly Gly Gly His
        35                  40                  45
Cys Thr Ala Ile Val Arg Gly Arg Ile Ala Asp Val Arg Leu Ala Val
    50                  55                  60
Glu Glu Gly Ala Glu Arg Ala Gln Gln Phe Gly Gln Glu Leu Ser Thr
65                  70                  75                  80
Leu Val Ile Pro Arg Pro Asp Pro Asn Leu Glu Lys Ile Leu Pro Ile
                85                  90                  95
Gly Ser Leu Leu Ala Gln Ile Ala Ser Lys Ser Arg Gly His Arg Leu
            100                 105                 110
Ser Ser His Ala Val Gly Leu Leu Glu Thr Arg Gly Phe Pro Ala Met
        115                 120                 125
Val Gly Ala Ala Asp Ala Met Leu Lys Ala Ala Asp Val Met Leu Thr
    130                 135                 140
Ala Tyr Glu Thr Ile Gly Ala Gly Leu Cys Thr Ala Ile Ile Arg Gly
145                 150                 155                 160
Thr Ala Ser Asn Thr Ala Ile Ala Leu Glu Ala Gly Met Ala Glu Ala
                165                 170                 175
Asp Arg Ile Gly Glu Leu His Ala Val Met Leu Val Pro Arg Pro Leu
            180                 185                 190
Glu Asp Leu Asp Gln Ser Leu Pro Leu Ala Pro Ala Leu Gln Arg Glu
        195                 200                 205
Leu Gln Pro Leu Arg Leu Pro Leu Thr Leu Lys Gln Lys Glu Thr Glu
    210                 215                 220
Pro Leu Ala Leu Gln Gly Ala Gln Ala Ser Val Ala Val Glu Ala
225                 230                 235                 240
Ala Ala Glu Arg Val Pro Val Asp Pro Pro Ala Asn Pro
                245                 250
```

<210> SEQ ID NO 24
<211> LENGTH: 759
<212> TYPE: DNA
<213> ORGANISM: Artificial Sequence
<220> FEATURE:
<223> OTHER INFORMATION: Synthetic tandem domain DNA sequence

<400> SEQUENCE: 24

```
atggaacgtc gtgatgattt taccgatctg gccctgggtc tggtgagtgt gcaaagtttt      60
ccggccatcg tgggtatcgc cgatcatatg ctgaagagta gtgatgtgct gctggttggt     120
tacgaaaaaa tcgtggtgg ccattgcacg gcgatcgtgc gtggtcgcat tgcggacgtg     180
cgcctggcgg tggaagaggg tgccgaacgt gcccaacaat ttggtcaaga actgagtacc     240
ctggtgattc cacgtccaga tccaaatctg gaaaagattc tgccgattgg tagtctgctg     300
gcgcaaatcg cgagtaaaag tcgtggtcat cgtctgagca gtcatgccgt tggcctgctg     360
gagacccgtg gtttcccagc catggtgggt gcggcggatg ccatgctgaa agcggccgat     420
gtgatgctga cggcctacga gaccattggt gccggtctgt gtaccgccat cattcgcggc     480
acggccagta ataccgcgat tgccctggaa gccggtatgg ccgaagccga tcgtattggt     540
gaactgcatg cggttatgct ggtgccacgc ccgctggaag acctggatca aagtctgccg     600
ctggccccag ccctgcaacg cgagctgcaa ccactgcgtc tgccactgac cctgaaacaa     660
aaagaaaccg agccactggc gctgcaaggt gccgcccaag ccagtgtggc cgttgaagcc     720
gccgccgagc gtgttccagt tgatccgcca gccaatcca                           759
```

<210> SEQ ID NO 25
<211> LENGTH: 99
<212> TYPE: PRT
<213> ORGANISM: Thermosynechococcus elongatus

<400> SEQUENCE: 25

```
Met Lys Ile Ala Arg Val Cys Gly Thr Val Thr Ser Thr Gln Lys Glu
1               5                   10                  15
Asp Thr Leu Thr Gly Val Lys Phe Leu Val Leu Gln Tyr Leu Gly Glu
                20                  25                  30
Asp Gly Glu Phe Leu Pro Asp Tyr Glu Val Ala Ala Asp Thr Val Gly
            35                  40                  45
Ala Gly Gln Asp Glu Trp Val Leu Val Ser Arg Gly Ser Ala Ala Arg
        50                  55                  60
His Ile Ile Asn Gly Thr Asp Lys Pro Ile Asp Ala Ala Val Val Ala
65                  70                  75                  80
Ile Ile Asp Thr Val Ser Arg Asp Asn Tyr Leu Leu Tyr Ser Lys Arg
                85                  90                  95
Thr Gln Tyr
```

<210> SEQ ID NO 26
<211> LENGTH: 300
<212> TYPE: DNA
<213> ORGANISM: Artificial Sequence
<220> FEATURE:
<223> OTHER INFORMATION: Synthetic pentamer DNA sequence

<400> SEQUENCE: 26

```
atgaaaattg cccgtgtgtg tggtaccgtg accagtaccc aaaaagaaga taccctgacc      60
ggtgtgaagt ttctggtgct gcaatacctg ggtgaagatg gtgaatttct gccagattac     120
gaagttgcgg cggacaccgt tggtgccggt caagatgaat gggtgctggt gagtcgcggt     180
agtgccgccc gtcacattat caatggcacc gataaaccaa ttgatgccgc cgtggtggcc     240
attattgata ccgttagtcg tgataattac ctgctgtata gtaaacgtac ccagtactaa     300
```

<210> SEQ ID NO 27

```
<211> LENGTH: 25
<212> TYPE: DNA
<213> ORGANISM: Escherichia coli

<400> SEQUENCE: 27
tttagagaaa gaggagaaat actag                                           25

<210> SEQ ID NO 28
<211> LENGTH: 28
<212> TYPE: DNA
<213> ORGANISM: Escherichia coli

<400> SEQUENCE: 28
tttagagatt aaagaggaga aatactag                                        28

<210> SEQ ID NO 29
<211> LENGTH: 27
<212> TYPE: DNA
<213> ORGANISM: Escherichia coli

<400> SEQUENCE: 29
tttagagtca cacaggaaac ctactag                                         27

<210> SEQ ID NO 30
<211> LENGTH: 34
<212> TYPE: DNA
<213> ORGANISM: Halothiobacillus neapolitanus

<400> SEQUENCE: 30
gattttgaat gagtctttat tgaggagaga agaa                                 34

<210> SEQ ID NO 31
<211> LENGTH: 41
<212> TYPE: DNA
<213> ORGANISM: Escherichia coli

<400> SEQUENCE: 31
tctagaaata attttgttta gagaaagagg agaaatacta g                         41

<210> SEQ ID NO 32
<211> LENGTH: 28
<212> TYPE: DNA
<213> ORGANISM: Escherichia coli

<400> SEQUENCE: 32
tttagagatt aaagaggaga aatactag                                        28

<210> SEQ ID NO 33
<211> LENGTH: 27
<212> TYPE: DNA
<213> ORGANISM: Escherichia coli

<400> SEQUENCE: 33
tttagagtca cacaggaaac ctactag                                         27

<210> SEQ ID NO 34
<211> LENGTH: 30
<212> TYPE: DNA
<213> ORGANISM: Artificial Sequence
<220> FEATURE:
<223> OTHER INFORMATION: Synthetic RBS sequence derived from E.coli

<400> SEQUENCE: 34
ttttgtttag agaaagagga gaaatactag                                      30
```

<210> SEQ ID NO 35
<211> LENGTH: 19
<212> TYPE: DNA
<213> ORGANISM: Artificial Sequence
<220> FEATURE:
<223> OTHER INFORMATION: Synthetic B1001 ribosome binding site

<400> SEQUENCE: 35
tttaagaagg agatatacc                                                19

<210> SEQ ID NO 36
<211> LENGTH: 20
<212> TYPE: DNA
<213> ORGANISM: Artificial Sequence
<220> FEATURE:
<223> OTHER INFORMATION: Synthetic B1001 ribosome binding site

<400> SEQUENCE: 36
ggctaacata gggtggatct                                               20

<210> SEQ ID NO 37
<211> LENGTH: 28
<212> TYPE: DNA
<213> ORGANISM: Artificial Sequence
<220> FEATURE:
<223> OTHER INFORMATION: Synthetic Ribosomal binding site

<400> SEQUENCE: 37
tctagagaaa gaggagaaat actagatg                                      28

<210> SEQ ID NO 38
<211> LENGTH: 31
<212> TYPE: DNA
<213> ORGANISM: Artificial Sequence
<220> FEATURE:
<223> OTHER INFORMATION: Synthetic Ribosomal binding site

<400> SEQUENCE: 38
tctagagatt aaagaggaga aatactagat g                                  31

<210> SEQ ID NO 39
<211> LENGTH: 30
<212> TYPE: DNA
<213> ORGANISM: Artificial Sequence
<220> FEATURE:
<223> OTHER INFORMATION: Synthetic Ribosomal binding site

<400> SEQUENCE: 39
tctagagtca cacaggaaac ctactagatg                                    30

<210> SEQ ID NO 40
<211> LENGTH: 19
<212> TYPE: PRT
<213> ORGANISM: Artificial Sequence
<220> FEATURE:
<223> OTHER INFORMATION: Encapsulation protein sequence fused to the
      N-terminus of an encapsulated protein.  The
      encapsulation protein sequence is derived from the
      N-terminus of an aldehyde dehydrogenase from H.
      ochraceum

<400> SEQUENCE: 40

Met Ala Leu Arg Glu Asp Arg Ile Ala Glu Ile Val Glu Arg Val Leu
1               5                   10                  15

Ala Arg Leu

<210> SEQ ID NO 41
<211> LENGTH: 57
<212> TYPE: DNA
<213> ORGANISM: Artificial Sequence
<220> FEATURE:
<223> OTHER INFORMATION: Synthetic DNA sequence selected to encode the
      protein sequence of SEQ ID NO:40 derived from the
      N-terminus of an aldehyde dehydrogenase from H.
      ochraceum

<400> SEQUENCE: 41
atggcactgc gtgaagatcg tatcgctgaa atcgtggaac gtgtcctggc ccgtctg          57

<210> SEQ ID NO 42
<211> LENGTH: 21
<212> TYPE: PRT
<213> ORGANISM: Artificial Sequence
<220> FEATURE:
<223> OTHER INFORMATION: Synthetic protein sequence fused to C-terminus
      of an encapsulated protein

<400> SEQUENCE: 42

Glu Pro Glu Asp Asn Glu Asp Val Gln Ala Ile Val Lys Ala Ile Met
1               5                   10                  15

Ala Lys Leu Asn Leu
            20

<210> SEQ ID NO 43
<211> LENGTH: 63
<212> TYPE: DNA
<213> ORGANISM: Artificial Sequence
<220> FEATURE:
<223> OTHER INFORMATION: Synthetic DNA sequence fused to the 3' end of
      the DNA encoding an encapsulated protein.  The synthetic DNA
      sequence is selected to encode the protein sequence of SEQ ID
      NO:42.

<400> SEQUENCE: 43
gaaccggaag acaatgaaga tgtgcaggca atcgtgaaag caattatggc taaactgaac       60
ctg                                                                    63

<210> SEQ ID NO 44
<211> LENGTH: 17
<212> TYPE: PRT
<213> ORGANISM: Haliangium ochraceum

<400> SEQUENCE: 44

Arg Asp Asp Leu Val Arg Val Ile Arg Glu Glu Leu Val Arg Ala Leu
1               5                   10                  15

Ala

<210> SEQ ID NO 45
<211> LENGTH: 18
<212> TYPE: PRT
<213> ORGANISM: Haliangium ochraceum

<400> SEQUENCE: 45

Ala Leu Arg Glu Asp Arg Ile Ala Glu Ile Val Glu Arg Val Leu Ala
1               5                   10                  15

Arg Leu

<210> SEQ ID NO 46
<211> LENGTH: 54

```
<212> TYPE: DNA
<213> ORGANISM: Haliangium ochraceum

<400> SEQUENCE: 46
gcgctgcgcg aagatcgcat tgcggaaatt gtggaacgcg tgctggcgcg cctg        54
```